(12) United States Patent
Huck et al.

(10) Patent No.: US 10,233,160 B2
(45) Date of Patent: Mar. 19, 2019

(54) SUBSTITUTED PYRIDO[3,4-D]PYRIMIDINES AND PYRIDO[4,3-D]PYRIMIDINES AS P70S6K INHIBITORS

(71) Applicant: Merck Patent GmbH, Darmstadt (DE)

(72) Inventors: Bayard R. Huck, Sudbury, MA (US); Ruoxi Lan, Waltham, MA (US); Justin Potnick, Acton, MA (US); Lizbeth Celeste DeSelm, Melrose, MA (US); Mark W. Cronin, Jr., Arlington, MA (US); Constantin Neagu, Belmont, MA (US); Xiaoling Chen, Chestnut Hill, MA (US); Roch Boivin, North Chelmsford, MA (US); Theresa L. Johnson, Salem, MA (US); Andreas Goutopoulos, Boston, MA (US)

(73) Assignee: Merck Patent GmbH, Darmstadt (DE)

( * ) Notice: Subject to any disclaimer, the term of this patent is extended or adjusted under 35 U.S.C. 154(b) by 0 days.

(21) Appl. No.: 15/960,759

(22) Filed: Apr. 24, 2018

(65) Prior Publication Data

US 2018/0237402 A1 Aug. 23, 2018

Related U.S. Application Data

(60) Continuation of application No. 15/227,638, filed on Aug. 3, 2016, now Pat. No. 9,981,925, which is a division of application No. 14/432,618, filed as application No. PCT/US2013/072141 on Nov. 27, 2013, now Pat. No. 9,440,968.

(60) Provisional application No. 61/731,075, filed on Nov. 29, 2012.

(51) Int. Cl.
| | |
|---|---|
| A61K 31/519 | (2006.01) |
| C07D 487/04 | (2006.01) |
| C07D 253/08 | (2006.01) |
| C07D 403/12 | (2006.01) |
| C07D 401/12 | (2006.01) |
| C07D 471/04 | (2006.01) |
| A61K 45/06 | (2006.01) |
| A61K 31/53 | (2006.01) |

(52) U.S. Cl.
CPC .......... *C07D 253/08* (2013.01); *A61K 31/519* (2013.01); *A61K 31/53* (2013.01); *A61K 45/06* (2013.01); *C07D 401/12* (2013.01); *C07D 403/12* (2013.01); *C07D 471/04* (2013.01)

(58) Field of Classification Search
CPC .............. A61K 31/519; C07D 487/04
USPC ................... 514/264.11; 544/279
See application file for complete search history.

(56) References Cited

U.S. PATENT DOCUMENTS

| | | | |
|---|---|---|---|
| 6,084,095 | A | 7/2000 | Bridges et al. |
| 6,413,971 | B1 | 7/2002 | Arnold et al. |
| 7,928,106 | B2 | 4/2011 | Conte et al. |
| 8,637,532 | B2 | 1/2014 | Sutton et al. |
| 2008/0194546 | A1 | 8/2008 | Hummersone et al. |
| 2011/0183972 | A1 | 7/2011 | Zhao et al. |

FOREIGN PATENT DOCUMENTS

| | | |
|---|---|---|
| CA | 2887539 | * 6/2014 |
| CA | 2887539 A1 | 6/2014 |
| WO | 03/064397 A1 | 8/2003 |
| WO | 04/014873 A1 | 2/2004 |
| WO | 04/092154 A1 | 10/2004 |
| WO | 05/033086 A1 | 4/2005 |
| WO | 05/039506 A2 | 5/2005 |
| WO | 05/054237 A1 | 6/2005 |
| WO | 05/056014 A1 | 6/2005 |
| WO | 05/117909 A1 | 12/2005 |
| WO | 06/071819 A1 | 7/2006 |
| WO | 06/120573 A2 | 11/2006 |
| WO | 06/131835 A2 | 12/2006 |

(Continued)

OTHER PUBLICATIONS

Barlund et al., Multiple Genes at 17q23 Undergo Amplification and Overexpression in Breast Cancer, Cancer Res., 2000, 60:5340-5344.
Bundgaard H. ed., Design and Application of Prodrugs, 1985, Harwood Academic Publishers Gmfh.
Choo et al., Rapamycin differentially inhibits S6Ks and 4E-BP1 to mediate cell-type-specific repression of mRNA translation, PNAS, 2008, 105(45): 17414-17419.
Couch et al., Localization of PS6K to Chromosomal Region 17q23 and Determination of Its Amplification in Breast Cancer, Cancer Res., 1999, 59:1408-11.

(Continued)

*Primary Examiner* — Douglas M Willis
(74) *Attorney, Agent, or Firm* — Pascal A. Stein; EMD Serono Research & Development Institute

(57) ABSTRACT

Novel azaquinazoline carboxamide derivatives of formula (I)

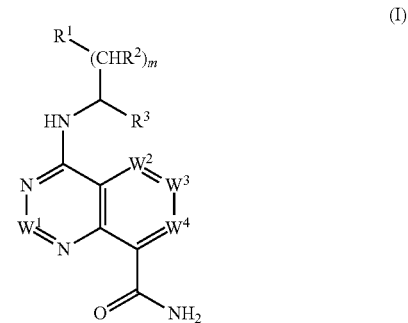

wherein $W^1$, $W^2$, $W^3$, $W^4$, $R^1$, $R^2$, $R^3$ and m which are defined above, are p70S6K inhibitor, and can be employed, inter alia, for the treatment of hyperproliferative disorders.

12 Claims, No Drawings

(56) References Cited

FOREIGN PATENT DOCUMENTS

| WO | 06/136821 A1 | 12/2006 |
|---|---|---|
| WO | 08/140947 A1 | 11/2008 |
| WO | 10/093419 A1 | 8/2010 |
| WO | 2011025938 A2 | 3/2011 |
| WO | 12/013282 A1 | 2/2012 |
| WO | 12/016001 A1 | 2/2012 |
| WO | 12/069146 A1 | 5/2012 |
| WO | 13/082345 A1 | 6/2013 |

OTHER PUBLICATIONS

Dar et al., Aurora Kinase Inhibitors—Rising Stars in Cancer Therapeutics? Mol. Cancer Ther, 2010, 9(2): 268-278.
Garcia-Bustos et al., PIK1, an essential phosphatidylinositol 4-kinase associated with the yeast nucleus, EMBO J., 1994, 13(10):2352-2361.
Hanks, S.K. and Hunter T., The eukaryotic protein kinase superfamily: Kinase (catalytic) domain structure and classification, FASEB J., 1995, 9:576-596.
Hardie and Hanks, The Protein Kinase Facts Book. I and II, 1995, Academic Press, San Diego, CA.
Hiles et al., Phosphatidylinositol 3-Kinase: Structure and Expression of the 110 kd Catalytic Subunit, Cell, 1992, 70:419-429.
Houben-Weyl, Methoden der organischen Chemie [Methods of Organic Chemistry], Georg-Thieme-Verlag, Stuttgart.
Knighton et al., Crystal Structure of the Catalytic Subunit of Cyclic Adenosine Monophosphate-Dependent Protein Kinase, Science, 1991, 253:407-414.
Kunz J. et al., Target of Rapamycin in Yeast, TOR2, Is an Essential Phosphatidylinositol Kinase Homolog Required for G1 Progression, Cell, 1993, 73:585-596.
Tamburini et al., Mammalian Target of rapamycin (mTOR) inhibition activates phosphatidylinositol 3-kinase/Akt by up-regulating insulin-like growth factor-1 receptor signaling in acute myeloid leukemia: rationale for therapeutic inhibition of both pathways, Blood, 2008, 111(1): 379-382.
Wermuth et al., Designing Prodrugs and Bioprecursors I: Carrier Prodrugs, The Practice of Medicinal Chemistry, Academic Press, 1996, Chapter 31: 671-696.
Wu et al., 17q23 Amplifications in Breast Cancer Involve the PAT1, RAD51C, PS6K, and SIGMA1B Genes, Cancer Res. (2000): 60:5371-5375.
Yoshida et al., Study of biodegradable copoly(L-lactic acid/glycolic acid) formulations with controlled release of Z-100 for application in radiation therapy, International Journal of Pharmaceutics, 1995, 115: 61-67.
Hackam et al., JAMA, 296(14), 2006, 1831-1732.
Jordan, V.C., Nature Reviews: Drug Discovery, 2, 2003, 205.
Smaill et al., J. Med. Chem., 1999, 42: 1803-1815.
Smaill et al., J. Med. Chem., 2000, 43: 1380-1397.

\* cited by examiner

SUBSTITUTED PYRIDO[3,4-D]PYRIMIDINES AND PYRIDO[4,3-D]PYRIMIDINES AS P70S6K INHIBITORS

RELATED APPLICATION

This application is a continuation of U.S. application Ser. No. 15/227,638, which is a divisional application of U.S. application Ser. No. 14/432,618, which is a U.S. national stage application of international application PCT/US2013/072141, filed on Nov. 27, 2013, which claims the benefit of U.S. Provisional application 61/731,075, filed on Nov. 29, 2012. The contents of the aforementioned applications are incorporated herein in their entireties by reference.

FIELD OF THE INVENTION

The present invention relates to compounds of formula (I)

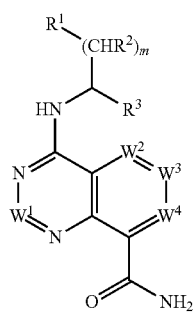

wherein $W^1$, $W^2$, $W^3$, $W^4$, $R^1$, $R^2$, $R^3$ and m have the meaning as described below, and/or physiologically acceptable salts thereof. The compounds of formula (I) can be used as p70S6K inhibitors. Other aspects of the invention include pharmaceutical compositions comprising the compounds of formula (I), and the use of the compounds of formula (I) for the treatment of hyperproliferative disorders.

BACKGROUND

Protein kinases constitute a large family of structurally related enzymes that are responsible for the control of a wide variety of signal transduction processes within the cell (Hardie, G. and Hanks, S. (1995) The Protein Kinase Facts Book. I and II, Academic Press, San Diego, Calif.). The kinases may be categorized into families by the substrates they phosphorylate (e.g., protein-tyrosine, protein-serine/threonine, lipids, etc.). Sequence motifs have been identified that generally correspond to each of these kinase families (e.g., Hanks & Hunter, FASEB J. 9: 576-596 (1995); Knighton et al., Science 253: 407-414 (1991); Hiles et al., Cell 70: 419-429 (1992); Kunz et al., Cell 73:585-596 (1993); Garcia-Bustos et al., EMBO J. 13:2352-2361 (1994)).

Protein kinases may be characterized by their regulation mechanisms. These mechanisms include, for example, autophosphorylation, transphosphorylation by other kinases, protein-protein interactions, protein-lipid interactions, and protein-polynucleotide interactions. An individual protein kinase may be regulated by more than one mechanism.

Kinases regulate many different cell processes including, but not limited to, proliferation, differentiation, apoptosis, motility, transcription, translation and other signaling processes, by adding phosphate groups to target proteins. These phosphorylation events act as molecular on/off switches that can modulate or regulate the target protein biological function.

Phosphorylation of target proteins occurs in response to a variety of extracellular signals (hormones, neurotransmitters, growth and differentiation factors, etc.), cell cycle events, environmental or nutritional stresses, etc. The appropriate protein kinase are involved in signaling pathways to activate or inactivate (either directly or indirectly), for example, a metabolic enzyme, regulatory protein, receptor, cytoskeletal protein, ion channel or pump, or transcription factor. Uncontrolled signaling due to defective control of protein phosphorylation has been implicated in a number of diseases, including, for example, inflammation, cancer, allergy/asthma, diseases and conditions of the immune system, diseases and conditions of the central nervous system, and angiogenesis.

Protein kinase 70S6K, the 70 kDa ribosomal protein kinase p70S6K (also known as SK6, p70/p85 S6 kinase, p70/p85 ribosomal S6 kinase and pp70S6K), is a member of the AGC subfamily of protein kinases. p70S6K is a serine-threonine kinase that is a component of the phosphatidylinositol 3 kinase (PI3K)/AKT pathway. p70S6K is downstream of PI3K, and activation occurs through phosphorylation at a number of sites in response to numerous mitogens, hormones and growth factors. p70S6K activity is also under the control of a mTOR-containing complex (TORC1) since rapamycin acts to inhibit p70S6K activity. p70S6K is regulated by PI3K downstream targets AKT and PKCζ. Akt directly phosphorylates and inactivates TSC2, thereby activating mTOR. In addition, studies with mutant alleles of p70S6K that are inhibited by Wortmannin but not by rapamycin suggest that the PI3K pathway can exhibit effects on p70S6K independent of the regulation of mTOR activity.

The enzyme p70S6K modulates protein synthesis by phosphorylation of the S6 ribosomal protein. S6 phosphorylation correlates with increased translation of mRNAs encoding components of the translational apparatus, including ribosomal proteins and translational elongation factors whose increased expression is essential for cell growth and proliferation. These mRNAs contain an oligopyrimidime tract at their 5' transcriptional start (termed 5'TOP), which has been shown to be essential for their regulation at the translational level.

In addition to its involvement in translation, p70S6K activation has also been implicated in cell cycle control, neuronal cell differentiation, regulation of cell motility and a cellular response that is important in tumor metastases, the immune response and tissue repair. Antibodies to p70S6K abolish the mitogenic response driven entry of rat fibroblasts into S phase, indicating that p70S6K function is essential for the progression from G1 to S phase in the cell cycle. Furthermore, inhibition of cell cycle proliferation at the G1 to S phase of the cell cycle by rapamycin has been identified as a consequence of inhibition of the production of the hyperphosphorylated, activated form of p70S6K.

A role for p70S6K in tumor cell proliferation and protection of cells from apoptosis is supported based on its participation in growth factor receptor signal transduction, overexpression and activation in tumor tissues. For example, Northern and Western analyses revealed that amplification of the PS6K gene was accompanied by corresponding increases in mRNA and protein expression, respectively (Cancer Res. (1999) 59: 1408-11-Localization of PS6K to Chromosomal Region 17q23 and Determination of Its Amplification in Breast Cancer).

Chromosome 17q23 is amplified in up to 20% of primary breast tumors, in 87% of breast tumors containing BRCA2 mutations and in 50% of tumors containing BRCA1 mutations, as well as other cancer types such as pancreatic, bladder and neuroblastoma (cf. Barlund et al., Cancer Res. 60: 5340-5346 (2000)). It has been shown that 17q23 amplifications in breast cancer involve the PAT1, RAD51C, PS6K, and SIGMA1B genes (Cancer Res. (2000): 60, pp. 5371-5375). The p70S6K gene has been identified as a target of amplification and overexpression in this region, and statistically significant association between amplification and poor prognosis has been observed.

Clinical inhibition of p70S6K activation was observed in renal carcinoma patients treated with CCl-779 (rapamycin ester), an inhibitor of the upstream kinase mTOR. A significant linear association between disease progression and inhibition of p70S6K activity was reported.

In response to energy stress, the tumor suppressor LKB1 activates AMPK which phosphorylates the TSC1/2 complex and enables it to inactivate the mTOR/p70S6K pathway. Mutations in LKB1 cause Peutz-Jeghers syndrome (PJS), where patients with PJS are 15 times more likely to develop cancer than the general population. In addition, ⅓ of lung adenocarcinomas harbor inactivating LKB1 mutations. p70S6K has been implicated in metabolic diseases and disorders. It was reported that the absence of p70S6K protects against age- and diet-induced obesity while enhancing insulin sensitivity. A role for p70S6K in metabolic diseases and disorders such as obesity, diabetes, metabolic syndrome, insulin resistance, hyperglycemia, hyperaminoacidemia, and hyperlipidmia is supported based upon the findings.

Compounds described as suitable for p70S6K inhibition are disclosed in WO 03/064397, WO 04/092154, WO 05/054237, WO 05/056014, WO 05/033086, WO 05/117909, WO 05/039506, WO 06/120573, WO 06/136821, WO 06/071819, WO 06/131835, WO 08/140947, WO 10/093419, and WO 12/069146.

In part, aurora kinases modulate a cell's progression through the cell cycle and mitosis. Hallmarks of cancer cell physiology are pathological changes to the normal progression through the cell cycle and mitosis. It has been documented that some compounds which inhibit aurora kinases are also associated with impaired chromosome alignment, weakening of the mitotic checkpoint, polyploidy, and subsequent cell death. More specifically, inhibition of Aurora B kinase has been shown to cause neutropenia as dose limiting toxicity in several clinical trials (Dar et al., Mol Cancer Ther 9: 268-278 (2010)). In addition, inhibition of Aurora B kinase can be an off target effect in ATP competitive kinase inhibitors. These Aurora B kinase inhibitors would also be expected to show neutropenia as dose limiting toxicity caused by aurora inhibition and, therefore, have a limited therapeutic window. Moreover, some aurora kinase inhibitors can also induce polyploidy in normal mammary epithelial cell cultures, thereby, raising the issue of adverse long-term clinical.

Therefore, it is expected that p70S6K inhibitors, which substantially spare or significantly reduce the inhibition of Aurora B kinase, hold special promise in the treatment of hyperproliferative diseases, such as cancer, by reducing neutropenia as dose limiting toxicity and, thereby, improving the therapeutic window for these compounds. Furthermore, it is expected that p70S6K inhibitors, which also inhibit kinase Akt (upstream of p70S6K in the PI3K pathway), provide more efficient PI3K pathway shutdown (Choo et al., PNAS USA 105(45): 17414-9 (2008)), and allow for capture of any Akt feedback loop activation (Tamburini et al., Blood 111: 379-82 (2008)).

SUMMARY OF THE INVENTION

The invention had the object of finding novel compounds having valuable properties, in particular those which can be used for the preparation of medicaments. It has been surprisingly found that the compounds according to the invention and salts thereof have very valuable pharmacological properties while being well tolerated. In particular, they act as p70S6K inhibitors and optionally, as Akt inhibitors.

In one aspect, the invention provides compounds of formula (I)

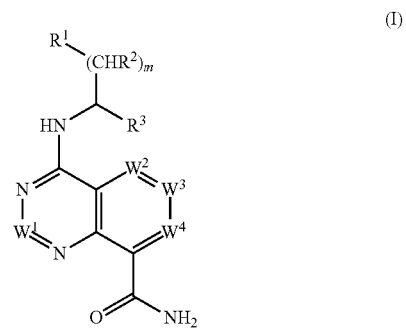

wherein each $W^1$, $W^2$, $W^3$, $W^4$ is independently N or CH, wherein at least one of $W^1$, $W^2$, $W^3$ or $W^4$ is N;

$R^1$ is Ar or $Het^1$;

each $R^2$, $R^4$, $R^5$ is independently Y;

$R^3$ is Y or $-(CH_2)_p-NR^4R^5$;

$R^2$ and $R^3$ together with the atoms to which each is attached, may form $-(CH_2)_n-NY-(CH_2)_p$;

$R^4$ and $R^5$ together with the atoms to which each is attached, may form $-(CY_2)_q-$;

Y is H or A;

A is unbranched or branched alkyl having 1-10 C atoms, in which 1-7 H atoms can be replaced independently from one another by Hal;

Ar is an unsaturated or aromatic mono- or bicyclic carbocycle having 3-10 C atoms, which can be substituted by at least one substituent selected from the group of Hal, A, OY, CN, COY, COOY, CONYY, NYCOY, NYCONYY, SO$_2$Y, SO$_2$NYY, NYSO$_2$Y, NYY, NO$_2$, OCN, SCN, SH, optionally substituted phenyl and $Het^1$;

$Het^1$ is an unsaturated or aromatic mono- or bicyclic heterocycle having 2-10 C atoms and 1-4 N, O and/or S atoms, which can be substituted by at least one substituent selected from the group of Hal, A, OY, CN, COY, COOY, CONYY, NYCOY, NYCONYY, SO$_2$Y, SO$_2$NYY, NYSO$_2$Y, NYY, NO$_2$, OCN, SCN, SH, optionally substituted phenyl and $Het^2$;

$Het^2$ is an optionally substituted, saturated, unsaturated or aromatic monocyclic 5-6-membered heterocycle having 2-5 C atoms and 1-3 N, O and/or S atoms;

Hal is F, Cl, Br or I;

m is 0 or 1;

each n or p is independently 0, 1, 2 or 3; and
q is 2, 3, 4, 5 or 6;
and/or a physiologically acceptable salt thereof.

DETAILED DESCRIPTION OF THE INVENTION

In the meaning of the present invention, the compound is defined to include pharmaceutically usable derivatives, solvates, prodrugs, tautomers, enantiomers, racemates and stereoisomers thereof, including mixtures thereof in all ratios.

The term "pharmaceutically usable derivatives" is taken to mean, for example, the salts of the compounds according to the invention and also so-called prodrug compounds. The term "solvates" of the compounds is taken to mean adductions of inert solvent molecules onto the compounds, which are formed owing to their mutual attractive force. Solvates are, for example, mono- or dihydrates or alkoxides. The invention also comprises solvates of salts of the compounds according to the invention. The term "prodrug" is taken to mean compounds according to the invention which have been modified by means of, for example, alkyl or acyl groups, sugars or oligopeptides and which are rapidly cleaved in the organism to form the effective compounds according to the invention. These also include biodegradable polymer derivatives of the compounds according to the invention, as described, for example, in Int. J. Pharm. 115, 61-67 (1995). It is likewise possible for the compounds of the invention to be in the form of any desired prodrugs such as, for example, esters, carbonates, carbamates, ureas, amides or phosphates, in which cases the actually biologically active form is released only through metabolism. Any compound that can be converted in-vivo to provide the bioactive agent (i.e. compounds of the invention) is a prodrug within the scope and spirit of the invention. Various forms of prodrugs are well known in the art and are described (e.g. Wermuth C G et al., Chapter 31: 671-696, The Practice of Medicinal Chemistry, Academic Press 1996; Bundgaard H, Design of Prodrugs, Elsevier 1985; Bundgaard H, Chapter 5: 131-191, A Textbook of Drug Design and Development, Harwood Academic Publishers 1991). Said references are incorporated herein by reference. It is further known that chemical substances are converted in the body into metabolites which may where appropriate likewise elicit the desired biological effect—in some circumstances even in more pronounced form. Any biologically active compound that was converted in-vivo by metabolism from any of the compounds of the invention is a metabolite within the scope and spirit of the invention.

The compounds of the invention may be present in the form of their double bond isomers as pure E or Z isomers, or in the form of mixtures of these double bond isomers. Where possible, the compounds of the invention may be in the form of the tautomers, such as keto-enol tautomers. All stereoisomers of the compounds of the invention are contemplated, either in a mixture or in pure or substantially pure form. The compounds of the invention can have asymmetric centers at any of the carbon atoms. Consequently, they can exist in the form of their racemates, in the form of the pure enantiomers and/or diastereomers or in the form of mixtures of these enantiomers and/or diastereomers. The mixtures may have any desired mixing ratio of the stereoisomers. Thus, for example, the compounds of the invention which have one or more centers of chirality and which occur as racemates or as diastereomer mixtures can be fractionated by methods known per se into their optical pure isomers, i.e. enantiomers or diastereomers. The separation of the compounds of the invention can take place by column separation on chiral or nonchiral phases or by recrystallization from an optionally optically active solvent or with use of an optically active acid or base or by derivatization with an optically active reagent such as, for example, an optically active alcohol, and subsequent elimination of the radical.

The invention also relates to the use of mixtures of the compounds according to the invention, for example mixtures of two diastereomers, for example in the ratio 1:1, 1:2, 1:3, 1:4, 1:5, 1:10, 1:100 or 1:1000. These are particularly preferably mixtures of stereoisomeric compounds.

The nomenclature as used herein for defining compounds, especially the compounds according to the invention, is in general based on the rules of the IUPAC-organization for chemical compounds and especially organic compounds. The terms indicated for explanation of the above compounds of the invention always, unless indicated otherwise in the description or in the claims, have the following meanings:

The term "unsubstituted" means that the corresponding radical, group or moiety has no substituents. The term "substituted" means that the corresponding radical, group or moiety has one or more substituents. Where a radical has a plurality of substituents, and a selection of various substituents is specified, the substituents are selected independently of one another and do not need to be identical. Even though a radical has a plurality of a specific-designated substituent (e.g. $Y_2$ or YY) the expression of such substituent may differ from each other (e.g. methyl and ethyl). It shall be understood accordingly that a multiple substitution by any radical of the invention may involve identical or different radicals. Hence, if individual radicals occur several times within a compound, the radicals adopt the meanings indicated, independently of one another. In case of a multiple substitution, the radical could be alternatively designated with R', R", R"', R"" etc.

The terms "alkyl" or "A" refer to acyclic saturated or unsaturated hydrocarbon radicals, which may be branched or straight-chain and preferably have 1, 2, 3, 4, 5, 6, 7, 8, 9 or 10 carbon atoms, i.e. $C_1$-$C_{10}$-alkyls. Examples of suitable alkyl radicals are methyl, ethyl, n-propyl, isopropyl, 1,1-, 1,2- or 2,2-dimethylpropyl, 1-ethylpropyl, 1-ethyl-1-methylpropyl, 1-ethyl-2-methylpropyl, 1,1,2- or 1,2,2-trimethylpropyl, n-butyl, isobutyl, sec-butyl, tert-butyl, 1-, 2- or 3-methylbutyl, 1,1-, 1,2-, 1,3-, 2,2-, 2,3- or 3,3-dimethylbutyl, 1- or 2-ethylbutyl, n-pentyl, iso-pentyl, neo-pentyl, tert-pentyl, 1-, 2-, 3- or -methyl-pentyl, n-hexyl, 2-hexyl, isohexyl, n-heptyl, n-octyl, n-nonyl, n-decyl, n-undecyl, n-dodecyl, n-tetradecyl, n-hexadecyl, n-octadecyl, n-icosanyl, n-docosanyl.

In a preferred embodiment of the invention, A denotes unbranched or branched alkyl having 1-10 C atoms, in which 1-7 H atoms may be replaced independently from one another by Hal. A more preferred A denotes unbranched or branched alkyl having 1-6 C atoms, in which 1-4 atoms may be replaced independently from one another by Hal. In a most preferred embodiment of the invention, A denotes unbranched or branched alkyl having 1-4 C atoms, in which 1-3 H atoms can be replaced independently from one another by Hal. It is highly preferred that A denotes unbranched or branched alkyl having 1-4 C atoms, in which 1-3 H atoms can be replaced independently from one another by F and/or Cl. Particularly preferred is $C_{1-4}$-alkyl. A $C_{1-4}$-alkyl radical is for example a methyl, ethyl, propyl, isopropyl, butyl, isobutyl, tert-butyl, sec-butyl, tert-butyl, fluoromethyl, difluoromethyl, trifluoromethyl, pentafluoroethyl, 1,1,1-trifluoroethyl or bromomethyl, especially methyl, ethyl, propyl or trifluoromethyl. It shall be understood that the respective denotation of A is independently of one another in any radical of the invention.

The terms "carbocycle" or "carbocyclyl" for the purposes of this invention refers to a mono- or polycyclic hydrocarbon systems of 3 to 14 ring atoms, preferably 4 to 10 ring atoms, more preferably 6 to 8 carbon atoms. The cyclic system may be saturated, mono- or poly-unsaturated, or aromatic.

The term "aryl" or "carboaryl" for the purposes of this invention refers to a mono- or polycyclic aromatic hydrocarbon systems having 3 to 14, preferably 4 to 10, more preferably 6 to 8 carbon atoms, which can be optionally substituted. The term "aryl" also includes systems in which the aromatic cycle is part of a bi- or polycyclic saturated, partially unsaturated and/or aromatic system, such as where the aromatic cycle is fused to an aryl, cycloalkyl, heteroaryl or heterocyclyl group as defined herein via any desired and possible ring member of the aryl radical. The bonding to the compounds of the general formula (I) can be effected via any possible ring member of the aryl radical. Examples of suitable aryl radicals are phenyl, biphenyl, naphthyl, 1-naphthyl, 2-naphthyl and anthracenyl, but likewise in-danyl, indenyl or 1,2,3,4-tetrahydronaphthyl. Preferred carboaryls of the invention are optionally substituted phenyl, naphthyl and biphenyl, more preferably optionally substituted monocylic carboaryl having 6-8 C atoms, most preferably optionally substituted phenyl.

In an embodiment of the invention, a carbocycle, including, but not limited to, carboaryl, is defined as "Ar". Examples of suitable Ar radicals are phenyl, o-, m- or p-tolyl, o-, m- or p-ethylphenyl, o-, m- or p-propylphenyl, o-, m- or p-isopropylphenyl, o-, m- or p-tert.-butylphenyl, o-, m- or p-hydroxyphenyl, o-, m- or p-methoxyphenyl, o-, m- or p-ethoxyphenyl, o-, m- or p-fluorophenyl, o-, m- or p-bromophenyl, o-, m- or p-chlorophenyl, o-, m- or p-sulfonamidophenyl, o-, m- or p-(N-methyl-sulfonamido)phenyl, o-, m- or p-(N,N-dimethyl-sulfonamido)-phenyl, o-, m- or p-(N-ethyl-N-methyl-sulfonamido)phenyl, o-, m- or p-(N,N-diethyl-sulfonamido)-phenyl, particularly 2,3-, 2,4-, 2,5-, 2,6-, 3,4- or 3,5-difluorophenyl, 2,3-, 2,4-, 2,5-, 2,6-, 3,4- or 3,5-dichlorophenyl, 2,3-, 2,4-, 2,5-, 2,6-, 3,4- or 3,5-dibromophenyl, 2,3,4-, 2,3,5-, 2,3,6-, 2,4,6- or 3,4,5-trichlorophenyl, 2,4,6-trimethoxyphenyl, 2-hydroxy-3,5-dichlorophenyl, p-iodophenyl, 4-fluoro-3-chlorophenyl, 4-chloro-3-fluorophenyl, 4-fluoro-3-trifluoromethylphenyl, 4-chloro-3-fluorophenyl, 4-chloro-3-trifluoromethylphenyl, 4-chloro-3-methoxylphenyl, 3-cyano-4-chloro-phenyl, 2-fluoro-4-bromophenyl, 2,5-difluoro-4-bromophenyl, 3-bromo-6-methoxyphenyl, 3-chloro-6-methoxyphenyl or 2,5-dimethyl-4-chlorophenyl.

Ar preferably denotes an unsaturated or aromatic mono- or bicyclic carbocycle having 3-10 C atoms, which can be substituted by at least one substituent selected from the group of Hal, A, OY, CN, COY, COOY, CONYY, NYCOY, NYCONYY, $SO_2Y$, $SO_2NYY$, $NYSO_2Y$, NYY, $NO_2$, OCN, SCN, SH, optionally substituted phenyl and $Het^1$. In a more preferred embodiment of the invention, Ar denotes a monocyclic aryl having 4-8 C atoms, which can be substituted by at least one substituent selected from the group of Hal, A, OY or CN. It is most preferred that Ar denotes phenyl, which can be mono- or disubstituted by at least one substituent selected from the group of Hal, A, OA or CN. In a highly preferred embodiment of the invention, Ar denotes phenyl, which is disubstituted by Hal and A.

The terms "heterocycle" or "heterocyclyl" for the purposes of this invention refers to a mono- or polycyclic system of 3 to 14 ring atoms, preferably 4 to 10 ring atoms, more preferably 4 to 8 ring atoms, comprising carbon atoms and 1, 2, 3, 4 or 5 heteroatoms, which are identical or different, in particular nitrogen, oxygen and/or sulfur. The cyclic system may be saturated, mono- or poly-unsaturated, or aromatic. In the case of a cyclic system consisting of at least two rings the rings may be fused or spiro or otherwise connected. Such heterocyclyl radicals can be linked via any ring member. The term "heterocyclyl" also includes systems in which the heterocycle is part of a bi- or polycyclic saturated, partially unsaturated and/or aromatic system, such as where the heterocycle is fused to an aryl, cycloalkyl, heteroaryl or heterocyclyl group as defined herein via any desired and possible ring member of the heterocyclyl radical. The bonding to the compounds of the general formula (I) can be effected via any possible ring member of the heterocyclyl radical.

Examples of suitable heterocyclyl radicals are pyrrolidinyl, thiapyrrolidinyl, piperidinyl, piperazinyl, oxapiperazinyl, oxapiperidinyl, oxadiazolyl, tetrahydrofuryl, imidazolidinyl, thiazolidinyl, tetrahydropyranyl, morpholinyl, tetrahydrothiophenyl, dihydropyranyl.

The term "heteroaryl" for the purposes of this invention refers to a 1-15, preferably 1-9, most preferably 5-, 6- or 7-membered mono- or polycyclic aromatic hydrocarbon radical which comprises at least 1, where appropriate also 2, 3, 4 or 5 heteroatoms, preferably nitrogen, oxygen and/or sulfur, where the heteroatoms are identical or different. Preferably, the number of nitrogen atoms is 0, 1, 2, 3 or 4, and that of the oxygen and sulfur atoms is independently from one another 0 or 1. The term "heteroaryl" also includes systems in which the aromatic cycle is part of a bi- or polycyclic saturated, partially unsaturated and/or aromatic system, such as where the aromatic cycle is fused to an aryl, cycloalkyl, heteroaryl or heterocyclyl group as defined herein via any desired and possible ring member of the heteroaryl radical. The bonding to the compounds of the general formula (I) can be effected via any possible ring member of the heteroaryl radical. Examples of suitable heteroaryl are pyrrolyl, thienyl, furyl, imidazolyl, thiazolyl, isothiazolyl, oxazolyl, oxadiazolyl, isoxazolyl, pyrazolyl, pyridinyl, pyrimidinyl, pyridazinyl, pyrazinyl, indolyl, quinolinyl, isoquinolinyl, imidazolyl, triazolyl, triazinyl, tetrazolyl, phthalazinyl, indazolyl, indolizinyl, quinoxalinyl, quinazolinyl, pteridinyl, carbazolyl, phenazinyl, phenoxazinyl, phenothiazinyl and acridinyl.

It is preferred that heteroaryl in the realms of "$Het^1$" denotes an unsaturated or aromatic mono- or bicyclic heterocycle having 2-10 C atoms and 1-4 N, O and/or S atoms, which can be substituted by at least one substituent selected from the group of Hal, A, OY, CN, COY, COOY, CONYY, NYCOY, NYCONYY, $SO_2Y$, $SO_2NYY$, $NYSO_2Y$, NYY, $NO_2$, OCN, SCN, SH, optionally substituted phenyl and $Het^2$. In a more preferred embodiment of the invention, $Het^1$ denotes a monocyclic heteroaryl having 4-8 C atoms and 1-3 N atoms, which can be substituted by at least one substituent selected from the group of Hal, A or OA. It is most preferred that $Het^1$ denotes pyridyl, which can be mono- or disubstituted by at least one substituent selected from the group of Hal, A or OA. Highly preferred $Het^1$ denotes pyridyl, which can be mono- or disubstituted by at least one substituent selected from the group of Hal or A. It shall be understood that the respective denotation of $Het^1$ is independently of one another in any radical of the invention.

It is preferred that heteroaryl in the realms of "$Het^2$" denotes an optionally substituted, saturated, unsaturated or aromatic monocyclic 5-6-membered heterocycle having 2-5 C atoms and 1-3 N, O and/or S atoms. In a more preferred embodiment of the invention, $Het^2$ denotes a saturated, unsaturated or aromatic monocyclic 5-6-membered heterocycle having 2-5 C atoms and 1-2 N, O and/or S atoms.

The term "halogen", "halogen atom", "halogen substituent" or "Hal" for the purposes of this invention refers to one or, where appropriate, a plurality of fluorine (F, fluoro), bromine (Br, bromo), chlorine (Cl, chloro) or iodine (I, iodo) atoms. The designations "dihalogen", "trihalogen" and "perhalogen" refer respectively to two, three and four substituents, where each substituent can be selected independently from the group consisting of fluorine, chlorine, bromine and iodine. Halogen preferably means a fluorine, chlorine or bromine atom. Fluorine and chlorine are more preferred, particularly when the halogens are substituted on an alkyl (haloalkyl) or alkoxy group (e.g. $CF_3$ and $CF_3O$). It shall be understood that the respective denotation of Hal is independently of one another in any radical of the invention.

In certain embodiments, the invention provides a compound of formula I, wherein each of $W^1$, $W^2$, $W^3$, $W^4$ is independently from one another N or CH but with the proviso that only one of $W^1$, $W^2$, $W^3$ or $W^4$ is N. In other words, either $W^1$, $W^2$, $W^3$ or $W^4$ is N while the respective three other radicals are CH. In certain embodiments, $W^1$ is N, and $W^2$, $W^3$, $W^4$ are CH. In certain embodiments, $W^2$ is N, and $W^1$, $W^3$, $W^4$ are CH.

In certain embodiments, $R^1$ is Ar. In certain embodiments, $R^1$ is $Het^1$.

In certain embodiments, $R^1$ is phenyl, naphthyl, cyclopropyl, cyclobutyl, cyclopentyl, cyclohexyl, cycloheptyl, adamantyl, cyclooctyl, [3.3.0]bicyclooctanyl, [4.3.0]bicyclononanyl, [4.4.0]bicyclodecanyl, [2.2.2]bicyclooctanyl, fluorenyl, indanyl, tetrahydronaphthyl, acridinyl, azocinyl, benzimidazolyl, benzofuranyl, benzothiofuranyl, benzothiophenyl, benzoxazolyl, benzthiazolyl, benztriazolyl, benztetrazolyl, benzisoxazolyl, benzisothiazolyl, benzimidazolinyl, carbazolyl, NH-carbazolyl, carbolinyl, chromanyl, chromenyl, cinnolinyl, decahydroquinolinyl, 2H,6H-1,5,2-dithiazinyl, dihydrofuro [2,3-b] tetrahydrofuran, furanyl, furazanyl, imidazolidinyl, imidazolinyl, imidazolyl, 1H-indazolyl, indolenyl, indolinyl, indolizinyl, indolyl, 3H-indolyl, isoindolinyl, isoindolenyl, isobenzofuranyl, isochromanyl, isoindazolyl, isoindolinyl, isoindolyl, isoquinolinyl, isothiazolyl, isoxazolyl, morpholinyl, naphthyridinyl, octahydroisoquinolinyl, oxadiazolyl, 1,2,3-oxadiazolyl, 1,2,4-oxadiazolyl; -1,2,5oxadiazolyl, 1,3,4-oxadiazolyl, oxazolidinyl, oxazolyl, oxazolidinyl, pyrimidinyl, phenanthridinyl, phenanthrolinyl, phenazinyl, phenothiazinyl, phenoxathiinyl, phenoxazinyl, phthalazinyl, piperazinyl, piperidinyl, pteridinyl, purinyl, pyranyl, pyrazinyl, pyrazolidinyl, pyrazolinyl, pyrazolyl, pyridazinyl, pyridooxazole, pyridoimidazole, pyridothiazole, pyridinyl, pyridyl, pyrimidinyl, pyrrolidinyl, pyrrolinyl, 2H-pyrrolyl, pyrrolyl, quinazolinyl, quinolinyl, 4H-quinolizinyl, quinoxalinyl, quinuclidinyl, tetrahydrofuranyl, tetrahydroisoquinolinyl, tetrahydroquinolinyl, 6H-1,2,5-thiadiazinyl, 1,2,3-thiadiazolyl, 1,2,4-thiadiazolyl, 1,2,5-thiadiazolyl, 1,3,4thiadiazolyl, thianthrenyl, thiazolyl, thienyl, thienothiazolyl, thienooxazolyl, thienoimidazolyl, thiophenyl, triazinyl, 1,2,3-triazolyl, 1,2,4-triazolyl, 1,2,5-triazolyl, 1,3,4-triazolyl, oxetanyl, azetidinyl, or xanthenyl; each of which is optionally substituted.

In various embodiments, $R^1$ is phenyl or pyridyl, each of which is optionally substituted.

In various embodiments, $R^1$ is

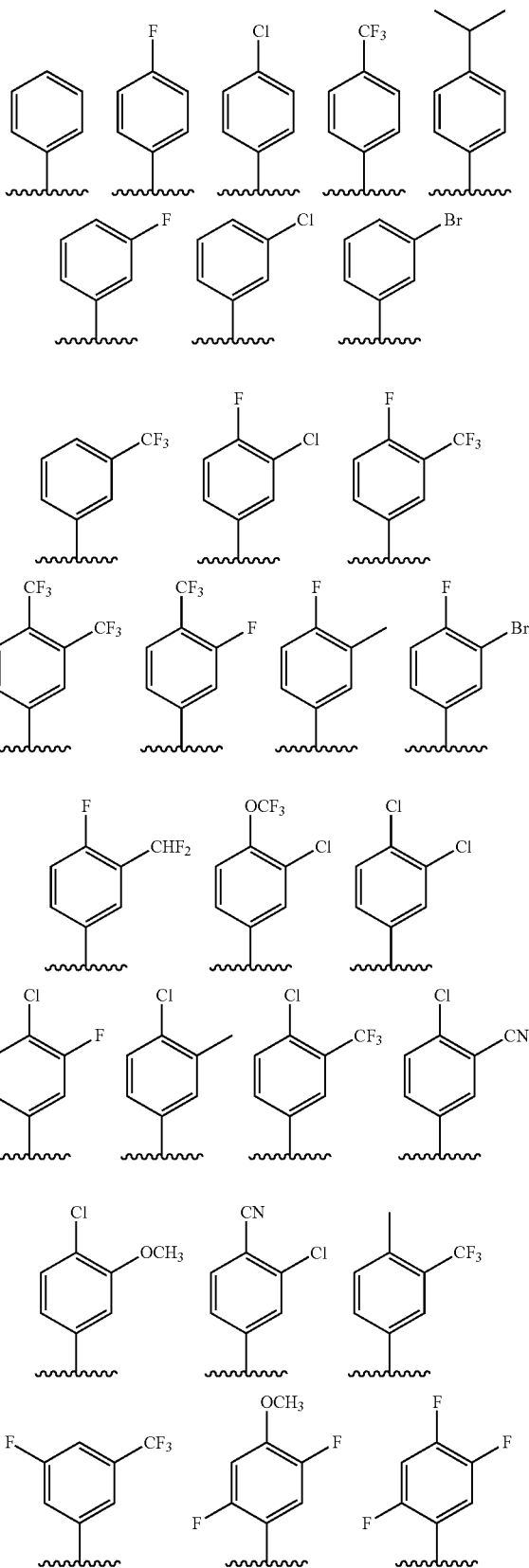

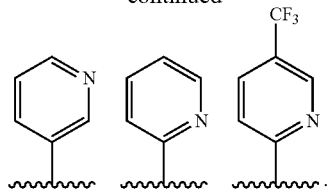

In certain embodiments, $R^2$ is H. In certain embodiments, $R^2$ is unbranched or branched alkyl having 1-10 C atoms, in which 1-7 H atoms can be replaced independently from one another by Hal.

In certain embodiments $R^3$ is H. In certain embodiments, $R^3$ is $-(CH_2)_p-NR^4R^5$. In certain embodiments, $R^3$ is $-CH_2-NR^4R^5$.

In certain embodiments, $R^3$ is H,

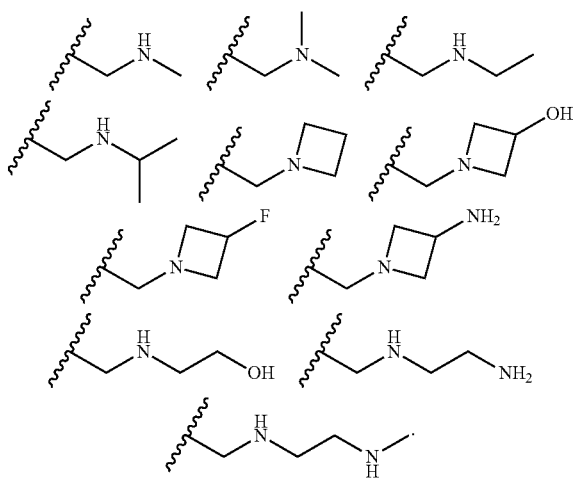

In certain embodiments, $R^2$ and $R^3$ together with the atoms to which each is attached, forms $-(CH_2)_n-NH-(CH_2)_p$. In certain embodiments, the group is

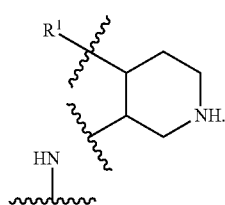

In certain embodiments, the $R^4$, $R^5$ radicals according to the present invention to be A, or together denote $-(CY_2)_q-$. In certain embodiments, $R^4$, $R^5$ together denote $-(CY_2)_q-$. In certain embodiments, $-(CH_2)_q-$. In In certain embodiments, $R^4$, $R^5$ together denote $-(CY_2)_3-$.

In an aspect of the invention, Y denotes H or A. It shall be understood that the respective denotation of Y is independently of one another in any radical of the invention.

In certain embodiments, m is 0 or 1.
In certain embodiments, n is 1 or 2.
In certain embodiments, p is 1 or 2. In certain embodiments, p is 1. It shall be understood that the respective denotation of p is independently of one another in any radical of the invention.

In certain embodiments, q is 3, 4 or 5. In certain embodiments, q is 3 or 4. In certain embodiments, q is 3.

Accordingly, the subject-matter of the invention relates to compounds of formula (I), in which at least one of the aforementioned radicals has any meaning, particularly realize any preferred embodiment, as described above. Radicals, which are not explicitly specified in the context of any embodiment of formula (I), sub-formulae thereof or other radicals thereto, shall be construed to represent any respective denotations according to formula (I) as disclosed hereunder for solving the problem of the invention. That means that the aforementioned radicals may adopt all designated meanings as each described in the prior or following course of the present specification, irrespective of the context to be found, including, but not limited to, any preferred embodiments. It shall be particularly understood that any embodiment of a certain radical can be combined with any embodiment of one or more other radicals.

In certain embodiments, the invention provides a compound of formula (I'):

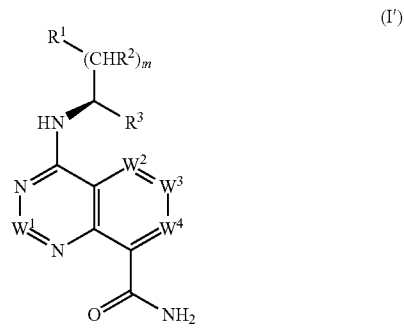

wherein $W^1$, $W^2$, $W^3$, $W^4$, $R^1$, $R^2$, $R^3$ and m are as defined above and described in embodiments, classes and subclasses above and herein, singly or in combination; and/or physiologically acceptable salts thereof.

In certain embodiments, the invention provides a compound of formula (I"):

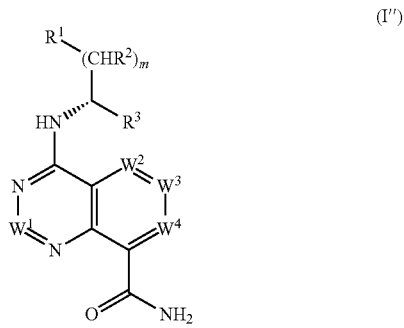

wherein $W^1$, $W^2$, $W^3$, $W^4$, $R^1$, $R^2$, $R^3$ and m are as defined above and described in embodiments, classes and subclasses above and herein, singly or in combination;

and/or physiologically acceptable salts thereof.

In certain embodiments, the invention provides a compound of formula (II):

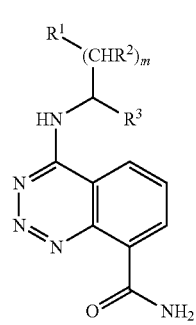

(II)

wherein $R^1$, $R^2$, $R^3$ and m are as defined above and described in embodiments, classes and subclasses above and herein, singly or in combination;
and/or physiologically acceptable salts thereof.

In certain embodiments, the invention provides a compound of formula (III):

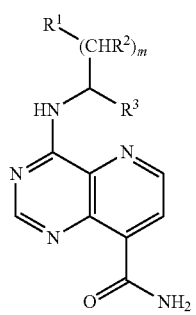

(III)

wherein $R^1$, $R^2$, $R^3$ and m are as defined above and described in embodiments, classes and subclasses above and herein, singly or in combination;
and/or physiologically acceptable salts thereof.

In certain embodiments, the invention provides a compound of formula (III-a):

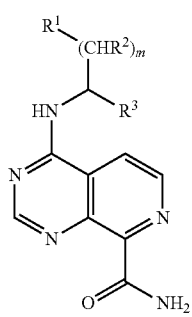

(III-a)

wherein $R^1$, $R^2$, $R^3$ and m are as defined above and described in embodiments, classes and subclasses above and herein, singly or in combination;
and/or physiologically acceptable salts thereof.

In certain embodiments, the invention provides a compound of formula (IV):

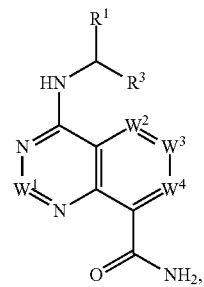

(IV)

wherein $W^1$, $W^2$, $W^3$, $W^4$, $R^1$, $R^3$ and n have the meaning as defined above and described in embodiments, classes and subclasses above and herein, singly or in combination;
and/or physiologically acceptable salts thereof.

In certain embodiments, the invention provides a compound of formula (V):

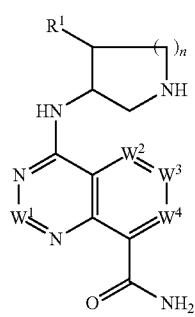

(V)

wherein $W^1$, $W^2$, $W^3$, $W^4$, $R^1$, $R^3$ and n have the meaning as defined above and described in embodiments, classes and subclasses above and herein, singly or in combination;
and/or physiologically acceptable salts thereof.

In certain embodiments, the invention provides a compound of formula (VI):

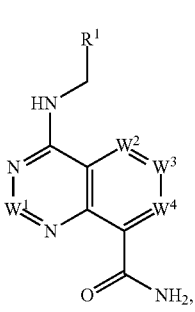

(VI)

wherein $W^1$, $W^2$, $W^3$, $W^4$, $R^1$, $R^4$ and $R^5$ have the meaning as defined above and described in embodiments, classes and subclasses above and herein, singly or in combination;
and/or physiologically acceptable salts thereof.

In certain embodiments, the invention provides a compound of formula (VII):

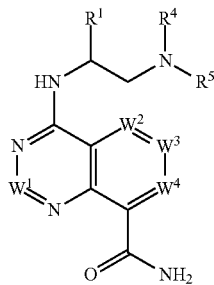

(VII)

wherein $W^1$, $W^2$, $W^3$, $W^4$, $R^1$, $R^4$ and $R^5$ have the meaning as defined above and described in embodiments, classes and subclasses above and herein, singly or in combination; and/or physiologically acceptable salts thereof.

In certain embodiments, the invention provides a compound of formula (VIII):

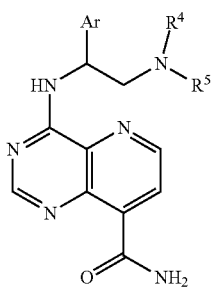

(VIII)

wherein $R^4$, $R^5$ and Ar have the meaning as defined above and described in embodiments, classes and subclasses above and herein, singly or in combination; and/or physiologically acceptable salts thereof.

In certain embodiments, the invention provides a compound of formula (VIII), wherein $R^4$ is methyl and $R^5$ is H. In certain embodiments, the invention provides a compound of formula (VIII), wherein $R^4$ and $R^5$ together with the nitrogen, form an azetidine ring.

In certain embodiments, the invention provides a compound of formula (VIII), wherein Ar is phenyl substituted with one or two of halogen or haloalkyl. In certain embodiments, the invention provides a compound of formula (VIII), wherein Ar is phenyl substituted one or two of Cl or $CF_3$. In certain embodiments, the invention provides a compound of formula (VIII), wherein Ar is phenyl substituted with one Cl and one $CF_3$. In certain embodiments, the invention provides a compound of formula (VIII), wherein Ar is phenyl substituted with two $CF_3$.

In certain embodiments, the invention provides a compound of formula (VIII), wherein $R^4$ is methyl and $R^5$ is H. In a further embodiment, Ar is phenyl substituted with one or two of halogen or haloalkyl. In a further embodiment, the invention provides a compound of formula (VIII), wherein Ar is phenyl substituted with para Cl and meta $CF_3$.

In certain embodiments, each of $W^1$, $W^2$, $W^3$, $W^4$, $R^1$, $R^2$, $R^3$, $R^4$ and $R^5$ and m is as defined above and described in embodiments, classes and subclasses above and herein, singly or in combination.

In certain embodiments, the invention provides a compound selected from 1-76 found in the examples.

The azaquinazoline carboxamide derivatives according to formula (I) and the starting materials for its preparation, respectively, are produced by methods known per se, as described in the literature (for example in standard works, such as Houben-Weyl, Methoden der organischen Chemie [Methods of Organic Chemistry], Georg-Thieme-Verlag, Stuttgart), i.e. under reaction conditions that are known and suitable for said reactions.

Use can also be made of variants that are known per se, but are not mentioned in greater detail herein. If desired, the starting materials can also be formed in-situ by leaving them in the un-isolated status in the crude reaction mixture, but immediately converting them further into the compound according to the invention. On the other hand, it is possible to carry out the reaction stepwise.

The reaction is generally carried out in an inert solvent. Suitable inert solvents are, for example, hydrocarbons, such as hexane, petroleum ether, benzene, toluene or xylene; chlorinated hydrocarbons, such as trichloroethylene, 1,2-dichloroethane, carbon tetrachloride, chloroform or dichloromethane; alcohols, such as methanol, ethanol, isopropanol, n-propanol, n-butanol or tert-butanol; ethers, such as diethyl ether, diisopropyl ether, tetrahydrofuran (THF) or dioxane; glycol ethers, such as ethylene glycol monomethyl or monoethyl ether, ethylene glycol dimethyl ether (diglyme); ketones, such as acetone or butanone; amides, such as acetamide, dimethylacetamide or dimethylformamide (DMF); nitriles, such as acetonitrile; sulfoxides, such as dimethyl sulfoxide (DMSO); carbon disulfide; carboxylic acids, such as formic acid, acetic acid or trifluoroacetic acid (TFA); nitro compounds, such as nitromethane or nitrobenzene; esters, such as ethyl acetate, or mixtures of the said solvents. Particular preference is given to DMF, TFA, $H_2O$, THF, tert-butanol, tert-amylalcohol, triethylamine or dioxane.

Depending on the conditions used, the reaction time is between a few minutes and 14 days, the reaction temperature is between about −30° C. and 140° C., normally between −10° C. and 130° C., preferably between 0° C. and 1000.

The present invention also relates to a process for manufacturing compounds of formula (I) comprising the steps of:
(a) reacting a compound of formula (IX)

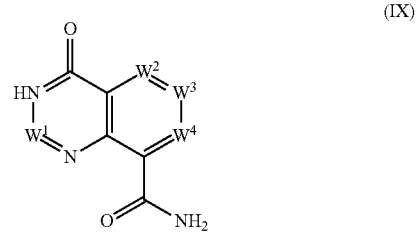

(IX)

wherein $W^1$, $W^2$, $W^3$ and $W^4$ have the meaning as defined above,
with a compound of formula (X)

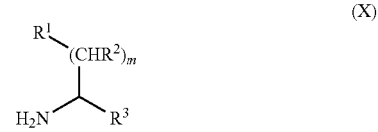

(X)

wherein R¹, R², R³ and m have the meaning as defined above,
to yield a compound of formula (I)

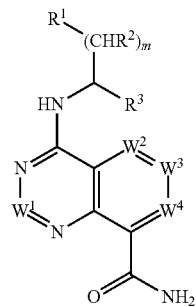

(I)

wherein W¹, W², W³, W⁴, R¹, R², R³ and m have the meaning as defined above,
and optionally
(b) converting a base or an acid of the compound of formula (I) into a salt thereof.

The azaquinazoline carboxamide derivatives of formula (I) are accessible via the route above. The starting materials, including the compounds of formulae (IX) and (X) are usually known to the skilled artisan, or they can be easily prepared by known methods. Accordingly, any compound of formulae (IX) and (X) can be purified, provided as intermediate product and used as starting material for the preparation of compounds of formula (I).

In the final step of the processes above, a salt of the compounds according to formula (I) is optionally provided. The said compounds according to the invention can be used in their final non-salt form. On the other hand, the present invention also encompasses the use of these compounds in the form of their pharmaceutically acceptable salts, which can be derived from various organic and inorganic acids and bases by procedures known in the art. Pharmaceutically acceptable salt forms of the compounds according to the invention are for the most part prepared by conventional methods. If the compound according to the invention contains a carboxyl group, one of its suitable salts can be formed by the reaction of the compound with a suitable base to give the corresponding base-addition salt. Such bases are, for example, alkali metal hydroxides, including potassium hydroxide, sodium hydroxide and lithium hydroxide; alkaline earth metal hydroxides, such as barium hydroxide and calcium hydroxide; alkali metal alkoxides, for example potassium ethoxide and sodium propoxide; and various organic bases, such as piperidine, diethanolamine and N-methylglutamine. The aluminum salts of the compounds according to the invention are likewise included. In most case of the compounds according to the invention, it is preferred that acid-addition salts are formed by treating these compounds with pharmaceutically acceptable organic and inorganic acids, for example hydrogen halides, such as hydrogen chloride, hydrogen bromide or hydrogen iodide, other mineral acids and corresponding salts thereof, such as sulfate, nitrate or phosphate and the like, and alkyl- and monoarylsulfonates, such as ethanesulfonate, toluenesulfonate and benzenesulfonate, and other organic acids and corresponding salts thereof, such as acetate, trifluoroacetate, tartrate, maleate, succinate, citrate, benzoate, salicylate, ascorbate and the like. Accordingly, pharmaceutically acceptable acid-addition salts of the compounds according to the invention include the following: acetate, adipate, alginate, arginate, aspartate, benzoate, benzenesulfonate (besylate), bisulfate, bisulfite, bromide, butyrate, camphorate, camphor-sulfonate, caprylate, chloride, chlorobenzoate, citrate, cyclopentanepropionate, digluconate, dihydrogenphosphate, dinitrobenzoate, dodecylsulfate, ethanesulfonate, fumarate, galacterate (from mucic acid), galacturonate, glucoheptanoate, gluconate, glutamate, glycerophosphate, hemisuccinate, hemisulfate, heptanoate, hexanoate, hippurate, hydrochloride, hydrobromide, hydroiodide, 2-hydroxyethanesulfonate, iodide, isethionate, isobutyrate, lactate, lactobionate, malate, maleate, malonate, mandelate, metaphosphate, methanesulfonate, methylbenzoate, monohydrogenphosphate, 2-naphthalenesulfonate, nicotinate, nitrate, oxalate, oleate, palmoate, pectinate, persulfate, phenylacetate, 3-phenylpropionate, phosphate, phosphonate, phthalate, but this does not represent a restriction.

With regard to that stated above, it can be seen that the expressions "pharmaceutically acceptable salt" and "physiologically acceptable salt", which are used interchangeable herein, in the present connection are taken to mean an active ingredient which comprises a compound according to the invention in the form of one of its salts, in particular if this salt form imparts improved pharmacokinetic properties on the active ingredient compared with the free form of the active ingredient or any other salt form of the active ingredient used earlier. The pharmaceutically acceptable salt form of the active ingredient can also provide this active ingredient for the first time with a desired pharmacokinetic property which it did not have earlier and can even have a positive influence on the pharmacodynamics of this active ingredient with respect to its therapeutic efficacy in the body.

Object of the present invention is also the use of compounds according to formula (I) and/or physiologically acceptable salts thereof for modulating and preferably inhibiting p70S6 kinase activity. The term "modulation" denotes any change in p70S6K-mediated signal transduction, which is based on the action of the specific inventive compounds capable to interact with the p70S6K target in such a manner that makes recognition, binding and inhibition possible. The term "inhibition" denotes any reduction in p70S6K activity, which is based on the action of the specific inventive compounds capable to interact with the target p70S6K in such a manner that makes recognition, binding and blocking possible. The compounds are characterized by such an appreciable affinity to p70S6K, which ensures a reliable binding and blocking of p70S6K activity. The same is valid for the Akt target, if appropriate. Preferably, the substances are p70S6K-specific in order to guarantee an exclusive and directed recognition of the p70S6K target. More preferably, the substances are bi-specific in order to guarantee an exclusive and directed recognition of the p70S6K target and the Akt target. In the context of the present invention, the term "recognition"—without being limited thereto—relates to any type of interaction between the specific compounds and the target, particularly covalent or non-covalent binding or association, such as a covalent bond, hydrophobic/hydrophilic interactions, van der Waals forces, ion pairs, hydrogen bonds, ligand-receptor interactions, and the like. Such association may also encompass the presence of other molecules such as peptides, proteins or nucleotide sequences. The present interaction is characterized by high affinity, high selectivity and minimal or even lacking cross-reactivity to other target molecules to exclude unhealthy and harmful impacts to the treated subject.

A preferred object of the present invention relates to a method for inhibiting p70S6 kinase, wherein a system capable of expressing the p70S6 kinase, preferably expressing the p70S6 kinase, is contacted with at least one compound of formula (I) according to the invention and/or physiologically acceptable salts thereof, under conditions such that said p70S6 kinase is inhibited. A cellular system is preferred in the scope of the invention. The cellular system is defined to be any subject provided that the subject comprises cells. Hence, the cellular system can be selected from the group of single cells, cell cultures, tissues, organs and animals. The method for inhibiting p70S6 kinase is preferably performed in-vitro. The prior teaching of the present specification concerning the compounds of formula (I), including any preferred embodiment thereof, is valid and applicable without restrictions to the compounds according to formula (I) and their salts when used in the method for inhibiting p70S6 kinase.

The compounds according to the invention preferably exhibit an advantageous biological activity, which is easily demonstrated in cell culture-based assays, for example assays as described herein or in prior art. In such assays, the compounds according to the invention preferably exhibit and cause an inhibiting effect. The compounds of the invention exhibit $EC_{50}$ values in the range of 10 nM to 25 µM. It is preferred that the compounds of the invention have an activity, as expressed by an $EC_{50}$ standard, of 5 µM or less, preferably 1 µM or less, more preferably 0.5 µM or less, most preferably less than 0.1 µM. "$EC_{50}$" is the effective concentration of a compound that produces 50% of the maximum possible response for that compound.

The method of the invention can be performed either in-vitro or in-vivo. The susceptibility of a particular cell to treatment with the compounds according to the invention can be particularly determined by in-vitro tests, whether in the course of research or clinical application. Typically, a culture of the cell is combined with a compound according to the invention at various concentrations for a period of time which is sufficient to allow the active agents to modulate p70S6K activity, usually between about one hour and one week. In-vitro treatment can be carried out using cultivated cells from a biopsy sample or cell line. In a preferred aspect of the invention, a follicle cell is stimulated for maturation. The viable cells remaining after the treatment are counted and further processed.

The host or patient can belong to any mammalian species, for example a primate species, particularly humans; rodents, including mice, rats and hamsters; rabbits; horses, cows, dogs, cats, etc. Animal models are of interest for experimental investigations, providing a model for treatment of human disease.

For identification of a signal transduction pathway and for detection of interactions between various signal transduction pathways, various scientists have developed suitable models or model systems, for example cell culture models and models of transgenic animals. For the determination of certain stages in the signal transduction cascade, interacting compounds can be utilized in order to modulate the signal. The compounds according to the invention can also be used as reagents for testing p70S6K-dependent signal transduction pathways in animals and/or cell culture models or in the clinical diseases mentioned in this application.

The use according to the previous paragraphs of the specification may be either performed in-vitro or in-vivo models. The modulation can be monitored by the techniques described in the course of the present specification. The in-vitro use is preferably applied to samples of humans suffering from hyperproliferative disorders. Testing of several specific compounds and/or derivatives thereof makes the selection of that active ingredient possible that is best suited for the treatment of the human subject. The in-vivo dose rate of the chosen derivative is advantageously pre-adjusted to the p70S6K susceptibility and/or severity of disease of the respective subject with regard to the in-vitro data. Therefore, the therapeutic efficacy is remarkably enhanced. Moreover, the subsequent teaching of the present specification concerning the use of the compounds according to formula (I) and its derivatives for the production of a medicament for the prophylactic or therapeutic treatment and/or monitoring is considered as valid and applicable without restrictions to the use of the compound for the modulation of p70S6K activity if expedient.

As discussed herein, the PI3K signaling pathway is relevant for various diseases, preferably in oncology. Accordingly, the compounds according to the invention are useful in the prophylaxis and/or treatment of diseases that are dependent on the said signaling pathways by interaction with one or more of the said signaling pathways. The present invention therefore relates to compounds according to the invention as modulators, preferably inhibitors, of the signaling pathways described herein, preferably of the PI3K-mediated signaling pathway. In particular, the invention relates to the use of compounds according to the invention for the preparation of a medicament for the treatment of hyperproliferative diseases related to the hyperactivity of p70S6K as well as diseases modulated by the p70S6K cascade in mammals, or disorders mediated by aberrant proliferation, such as cancer and inflammation.

The invention furthermore relates to a medicament comprising at least one compound according to the invention and/or pharmaceutically usable derivatives, salts, solvates and stereoisomers thereof, including mixtures thereof in all ratios. Preferably, the invention relates to a medicament comprising at least one compound according to the invention and/or physiologically acceptable salts thereof.

A "medicament" in the meaning of the invention is any agent in the field of medicine, which comprises one or more compounds of formula (I) or preparations thereof (e.g. a pharmaceutical composition or pharmaceutical formulation) and can be used in prophylaxis, therapy, follow-up or aftercare of patients who suffer from diseases, which are associated with p70S6K activity, in such a way that a pathogenic modification of their overall condition or of the condition of particular regions of the organism could establish at least temporarily.

Consequently, the invention also relates to a pharmaceutical composition comprising as active ingredient at least one compound of formula (I) according to the invention and/or physiologically acceptable salts thereof together with pharmaceutically tolerable adjuvants and/or excipients. It shall be understood that the compound of the invention is provided in an effective amount.

In the meaning of the invention, an "adjuvant" denotes every substance that enables, intensifies or modifies a specific response against the active ingredient of the invention if administered simultaneously, contemporarily or sequentially. Known adjuvants for injection solutions are, for example, aluminum compositions, such as aluminum hydroxide or aluminum phosphate, saponins, such as QS21, muramyldipeptide or muramyltripeptide, proteins, such as gamma-interferon or TNF, M59, squalen or polyols.

Furthermore, the active ingredient may be administered alone or in combination with other treatments. A synergistic effect may be achieved by using more than one compound in the pharmaceutical composition, i.e. the compound of formula (I) is combined with at least another agent as active ingredient, which is either another compound of formula (I) or a compound of different structural scaffold. The active ingredients can be used either simultaneously or sequentially. The invention also relates to a compound or pharmaceutical composition for inhibiting abnormal cell growth/cancer in a mammal which comprises an amount of a compound of the present invention, or a pharmaceutically acceptable salt or solvate or prodrug thereof, in combination with an amount of another anti-cancer therapeutic, wherein the amounts of the compound, salt, solvate, or prodrug, and of the chemotherapeutic are together effective in inhibiting abnormal cell growth/cancer. The present compounds are suitable for combination with known anti-cancer agents.

Many oncology therapeutics are presently known in the art. In a preferred embodiment, the other active pharmaceutical ingredient is an anti-cancer therapeutic that is a chemotherapeutic selected from the group consisting of mitotic inhibitors, alkylating agents, anti-metabolites, intercalating antibiotics, growth factor inhibitors, cell cycle inhibitors, enzymes, topoisomerase inhibitors, biological response modifiers, anti-hormones, angiogenesis inhibitors, and anti-androgens. In another preferred embodiment of the invention, the anti-cancer therapeutic is an antibody selected from the group consisting of bevacizumab, CD40-specific antibodies, chTNT-1/B, denosumab, zanolimumab, IGF1R-specific antibodies, lintuzumab, edrecolomab, WX G250, rituximab, ticilimumab, trastuzumab and cetuximab. In yet another preferred embodiment of the invention, the anti-cancer therapeutic is an inhibitor of another protein kinase, such as Akt, Axl, dyrk2, epha2, fgfr3, igf1r, IKK2, JNK3, Vegfr1, Vegfr2, Vegfr3 (also known as Flt-4), KDR, MEK, MET, Plk1, RSK1, Src, TrkA, Zap70, cKit, bRaf, EGFR, Jak2, PI3K, NPM-Alk, c-Abl, BTK, FAK, PDGFR, TAK1, LimK, Flt-3, PDK1, and Erk. Further anti-cancer agents are known to those of skill in the art and are useful with the compounds of the present invention.

The invention also relates to a set (kit) consisting of separate packs of an effective amount of a compound according to the invention and/or pharmaceutically acceptable salts, derivatives, solvates and stereoisomers thereof, including mixtures thereof in all ratios, and an effective amount of a further medicament active ingredient. The set comprises suitable containers, such as boxes, individual bottles, bags or ampoules. The set may, for example, comprise separate ampoules, each containing an effective amount of a compound according to the invention and/or pharmaceutically acceptable salts, derivatives, solvates and stereoisomers thereof, including mixtures thereof in all ratios, and an effective amount of a further medicament active ingredient in dissolved or lyophilized form.

Pharmaceutical formulations can be adapted for administration via any desired suitable method, for example by oral (including buccal or sublingual), rectal, nasal, topical (including buccal, sublingual or transdermal), vaginal or parenteral (including subcutaneous, intramuscular, intravenous or intradermal) methods. Such formulations can be prepared using all processes known in the pharmaceutical art by, for example, combining the active ingredient with the excipient(s) or adjuvant(s).

The pharmaceutical composition of the invention is produced in a known way using common solid or liquid carriers, diluents and/or additives and usual adjuvants for pharmaceutical engineering and with an appropriate dosage. The amount of excipient material that is combined with the active ingredient to produce a single dosage form varies depending upon the host treated and the particular mode of administration. Suitable excipients include organic or inorganic substances that are suitable for the different routes of administration, such as enteral (e.g. oral), parenteral or topical application, and which do not react with compounds of formula (I) or salts thereof. Examples of suitable excipients are water, vegetable oils, benzyl alcohols, alkylene glycols, polyethylene glycols, glycerol triacetate, gelatin, carbohydrates, e.g. lactose or starch, magnesium stearate, talc and petroleum jelly.

Pharmaceutical formulations adapted for oral administration can be administered as separate units, such as, for example, capsules or tablets; powders or granules; solutions or suspensions in aqueous or non-aqueous liquids; edible foams or foam foods; or oil-in-water liquid emulsions or water-in-oil liquid emulsions.

Pharmaceutical formulations adapted for parenteral administration include aqueous and non-aqueous sterile injection solutions comprising antioxidants, buffers, bacteriostatics and solutes, by means of which the formulation is rendered isotonic with the blood of the recipient to be treated; and aqueous and non-aqueous sterile suspensions, which may comprise suspension media and thickeners. The formulations can be administered in single-dose or multi-dose containers, for example sealed ampoules and vials, and stored in freeze-dried (lyophilized) state, so that only the addition of the sterile carrier liquid, for example water for injection purposes, immediately before use is necessary. Injection solutions and suspensions prepared in accordance with the recipe can be prepared from sterile powders, granules and tablets.

It goes without saying that, in addition to the above particularly mentioned constituents, the formulations may also comprise other agents usual in the art with respect to the particular type of formulation; thus, for example, formulations which are suitable for oral administration may comprise flavors.

In a preferred embodiment of the present invention, the pharmaceutical composition is adapted for oral administration. The preparations can be sterilized and/or can comprise auxiliaries, such as carrier proteins (e.g. serum albumin), lubricants, preservatives, stabilizers, fillers, chelating agents, antioxidants, solvents, bonding agents, suspending agents, wetting agents, emulsifiers, salts (for influencing the osmotic pressure), buffer substances, colorants, flavorings and one or more further active substances, for example one or more vitamins. Additives are well known in the art, and they are used in a variety of formulations.

Accordingly, the invention also relates to a pharmaceutical composition comprising as active pharmaceutical ingredient at least one compound of formula (I) according to the invention and/or physiologically acceptable salts thereof together with pharmaceutically tolerable adjuvants, optionally in combination with at least another active pharmaceutical ingredient. Both active pharmaceutical ingredients are particularly provided in effective amounts. The prior teaching of the present specification concerning administration route and combination product, respectively, is valid and applicable without restrictions to the combination of both features if expedient.

The terms "effective amount" or "effective dose" or "dose" are interchangeably used herein and denote an amount of the pharmaceutical compound having a prophylactically or therapeutically relevant effect on a disease or pathological conditions, i.e. which causes in a tissue, system, animal or human a biological or medical response which is sought or desired, for example, by a researcher or physician. A "prophylactic effect" reduces the likelihood of developing a disease or even prevents the onset of a disease.

A "therapeutically relevant effect" relieves to some extent one or more symptoms of a disease or returns to normality either partially or completely one or more physiological or biochemical parameters associated with or causative of the disease or pathological conditions. In addition, the expression "therapeutically effective amount" denotes an amount which, compared with a corresponding subject who has not received this amount, has the following consequence: improved treatment, healing, prevention or elimination of a disease, syndrome, condition, complaint, disorder or side-effects or also the reduction in the advance of a disease, complaint or disorder. The expression "therapeutically effective amount" also encompasses the amounts which are effective for increasing normal physiological function.

The respective dose or dosage range for administering the pharmaceutical composition according to the invention is sufficiently high in order to achieve the desired prophylactic or therapeutic effect of reducing symptoms of the aforementioned diseases, such as cancer and inflammation. It will be understood that the specific dose level, frequency and period of administration to any particular human will depend upon a variety of factors including the activity of the specific compound employed, the age, body weight, general state of health, gender, diet, time and route of administration, rate of excretion, drug combination and the severity of the particular disease to which the specific therapy is applied. Using well-known means and methods, the exact dose can be determined by one of skill in the art as a matter of routine experimentation. The prior teaching of the present specification is valid and applicable without restrictions to the pharmaceutical composition comprising the compounds of formula (I) if expedient.

Pharmaceutical formulations can be administered in the form of dosage units which comprise a predetermined amount of active ingredient per dosage unit. The concentration of the prophylactically or therapeutically active ingredient in the formulation may vary from about 0.1 to 100 wt %. Preferably, the compound of formula (I) or the pharmaceutically acceptable salts thereof are administered in doses of approximately 0.5 to 1000 mg, more preferably between 1 and 700 mg, most preferably 5 and 100 mg per dose unit. Generally, such a dose range is appropriate for total daily incorporation. In other terms, the daily dose is preferably between approximately 0.02 and 100 mg/kg of body weight. The specific dose for each patient depends, however, on a wide variety of factors as already described in the present specification (e.g. depending on the condition treated, the method of administration and the age, weight and condition of the patient). Preferred dosage unit formulations are those which comprise a daily dose or part-dose, as indicated above, or a corresponding fraction thereof of an active ingredient. Furthermore, pharmaceutical formulations of this type can be prepared using a process which is generally known in the pharmaceutical art.

Although a therapeutically effective amount of a compound according to the invention has to be ultimately determined by the treating doctor or vet by considering a number of factors (e.g. the age and weight of the animal, the precise condition that requires treatment, severity of condition, the nature of the formulation and the method of administration), an effective amount of a compound according to the invention for the treatment of neoplastic growth, for example colon or breast carcinoma, is generally in the range from 0.1 to 100 mg/kg of body weight of the recipient (mammal) per day and particularly typically in the range from 1 to 10 mg/kg of body weight per day. Thus, the actual amount per day for an adult mammal weighing 70 kg is usually between 70 and 700 mg, where this amount can be administered as a single dose per day or usually in a series of part-doses (such as, for example, two, three, four, five or six) per day, so that the total daily dose is the same. An effective amount of a salt or solvate or of a physiologically functional derivative thereof can be determined as the fraction of the effective amount of the compound according to the invention per se. It can be assumed that similar doses are suitable for the treatment of other conditions mentioned above.

The pharmaceutical composition of the invention can be employed as medicament in human and veterinary medicine. According to the invention, the compounds of formula (I) and/or physiologically salts thereof are suited for the prophylactic or therapeutic treatment and/or monitoring of diseases that are caused, mediated and/or propagated by p70S6K activity. It is preferred that the diseases are selected from the group of hyperproliferative disorders, cancer, metastases, tumors, angiogenesis disorders, tumor angiogenesis, benign hyperplasia, hemangioma, glioma, melanoma, Kaposi's sarcoma, prostate diseases related to vasculogenesis or angiogenesis, inflammation, pancreatitis, retinopathy, retinopathy of prematurity, diabetic retinopathy, diabetes, pain, restenosis, psoriasis, eczema, scleroderma and age-related macular degeneration. It shall be understood that the host of the compound is included in the present scope of protection according to the present invention.

Particular preference is given to the treatment of cancer, such as brain, lung, colon, epidermoid, squamous cell, bladder, gastric, pancreatic, breast, head, neck, renal, kidney, liver, ovarian, prostate, colorectal, uterine, rectal, oesophageal, testicular, gynecological, thyroid cancer, melanoma; hematologic malignancies, such as acute myelogenous leukemia, multiple myeloma, chronic myelogneous leukemia, myeloid cell leukemia; glioma; Kaposi's sarcoma; or any other type of solid or liquid tumors. More preferably, the cancer to be treated is chosen from breast, colorectal, lung, prostate or pancreatic cancer, or glioblastoma.

Exemplary disorders treated by the compounds of the invention include prostate cancer, thyroid cancer, liver cancer, lung cancer, breast cancer, colon cancer, prostate cancer, pituitary tumors, carcinoma of the bladder, breast, colon (e.g. colorectal carcinomas such as colon adenocarcinoma and colon adenoma), kidney, epidermis, liver, lung, for example adenocarcinoma, small cell lung cancer and non-small cell lung carcinomas, oesophagus, gall bladder, ovary, pancreas e.g. exocrine pancreatic carcinoma, stomach, cervix, endometrium, thyroid, prostate, or skin, for example squamous cell carcinoma; a hematopoietic tumour of lymphoid lineage, for example leukemia, acute lymphocytic leukemia, chronic lymphocytic leukemia, B-cell lymphoma, T-cell lymphoma, Hodgkin's lymphoma, non-Hodgkin's lymphoma; hairy cell lymphoma, or Burkett's lymphoma; a hematopoietic tumour of myeloid lineage, for example leukemias, acute and chronic myelogenous leukemias, myeloproliferative syndrome, myelodysplastic syndrome, or promyelocytic leukemia; multiple myeloma; thyroid follicular cancer; a tumour of mesenchymal origin, for example fibrosarcoma or rhabdomyosarcoma; a tumour of the central or peripheral nervous system, for example astrocytoma, neuroblastoma, glioma or schwannoma; melanoma; seminoma; teratocarcinoma; osteosarcoma; xeroderma pigmentosum; keratoctanthoma; thyroid follicular cancer; or Kaposi's sarcoma.

In certain embodiments, the disorder is bladder cancer, breast cancer, cervical cancer, colon cancer, epidermis cancer, gall bladder cancer, kidney cancer, liver cancer, lung cancer, pituitary tumors, oesophagus cancer, ovarian cancer, pancreatic cancer, prostate cancer, stomach cancer, thyroid cancer, leukemia, B-cell lymphoma, T-cell lymphoma, Hodgkin's lymphoma, non-Hodgkin's lymphoma, hairy cell lymphoma, Burkett's lymphoma, acute and chronic myelogenous leukemias, myeloproliferative syndrome, myelodysplastic syndrome, promyelocytic leukemia; multiple myeloma, thyroid follicular cancer; astrocytoma, neuroblastoma, glioma, schwannoma, melanoma or Kaposi's sarcoma.

In certain embodiments, the disorder is multiple myeloma, myeloproliferatoive disorders, endometrial cancer, prostate cancer, bladder cancer, lung cancer, ovarian cancer, breast cancer, gastric cancer, colorectal cancer, and oral squamous cell carcinoma. In certain embodiments, the disorder is multiple myeloma, bladder cancer, cervical cancer, prostate cancer, thyroid carcinomas, lung cancer, breast cancer, or colon cancer.

Further preference is given to treatment of a disease related to vasculogenesis or angiogenesis in a mammal, which comprises the administration of a therapeutically effective amount of a compound of the present invention, or a pharmaceutically acceptable salt, prodrug or hydrate thereof, and a pharmaceutically acceptable carrier. In one embodiment, the compound or pharmaceutical composition of the invention is for treating a disease selected from the group consisting of tumor angiogenesis; chronic inflammatory disease, such as rheumatoid arthritis, inflammatory bowel disease, atherosclerosis; skin diseases, such as psoriasis, eczema, scleroderma; metabolic diseases, such as diabetes, obesity, metabolic syndrome, insulin resistance, hyperglycemia, hyperaminoacidemia, hyperlipidmia, diabetic retinopathy, retinopathy of prematurity; and age-related macular degeneration.

The invention also relates to the use of compounds according to formula (I) and/or physiologically acceptable salts thereof for the prophylactic or therapeutic treatment and/or monitoring of diseases that are caused, mediated and/or propagated by p70S6 activity.

Furthermore, the invention relates to the use of compounds according to formula (I) and/or physiologically acceptable salts thereof for the production of a medicament for the prophylactic or therapeutic treatment and/or monitoring of diseases that are caused, mediated and/or propagated by p70S6K activity. Compounds of formula (I) and/or a physiologically acceptable salt thereof can furthermore be employed as intermediate for the preparation of further medicament active ingredients. The medicament is preferably prepared in a non-chemical manner, e.g. by combining the active ingredient with at least one solid, fluid and/or semi-fluid carrier or excipient, and optionally in conjunction with a single or more other active substances in an appropriate dosage form.

Another object of the present invention are compounds of formula (I) according to the invention and/or physiologically acceptable salts thereof for use in the prophylactic or therapeutic treatment and/or monitoring of diseases that are caused, mediated and/or propagated by p70S6K activity. Another preferred object of the invention concerns compounds of formula (I) according to the invention and/or physiologically acceptable salts thereof for use in the prophylactic or therapeutic treatment and/or monitoring of hyperproliferative disorders. The prior teaching of the present specification concerning the compounds of formula (I), including any preferred embodiment thereof, is valid and applicable without restrictions to the compounds according to formula (I) and their salts for use in the prophylactic or therapeutic treatment and/or monitoring of hyperproliferative disorders.

The compounds of formula (I) according to the invention can be administered before or following an onset of disease once or several times acting as therapy. The aforementioned compounds and medical products of the inventive use are particularly used for the therapeutic treatment. A therapeutically relevant effect relieves to some extent one or more symptoms of a disorder, or returns to normality, either partially or completely, one or more physiological or biochemical parameters associated with or causative of a disease or pathological condition. Monitoring is considered as a kind of treatment provided that the compounds are administered in distinct intervals, e.g. in order to booster the response and eradicate the pathogens and/or symptoms of the disease completely. Either the identical compound or different compounds can be applied. The medicament can also be used to reducing the likelihood of developing a disorder or even prevent the initiation of disorders associated with p70S6K activity in advance or to treat the arising and continuing symptoms. The disorders as concerned by the invention are preferably hyperproliferative disorders.

In the meaning of the invention, prophylactic treatment is advisable if the subject possesses any preconditions for the aforementioned physiological or pathological conditions, such as a familial disposition, a genetic defect, or a previously passed disease.

It is another object of the invention to provide a method for treating diseases that are caused, mediated and/or propagated by p70S6K activity, wherein at least one compound of formula (I) according to the invention and/or physiologically acceptable salts thereof is administered to a mammal in need of such treatment. It is another preferred object of the invention to provide a method for treating hyperproliferative disorders, wherein at least one compound of formula (I) according to the invention and/or physiologically acceptable salts thereof is administered to a mammal in need of such treatment. The compound is preferably provided in an effective amount as defined above. The preferred treatment is an oral administration.

In another preferred aspect, the method for treating cancer in a mammal comprises administering to the mammal an amount of a compound of the present invention in combination with radiation therapy, wherein the amount of the compound is in combination with the radiation therapy effective in treating cancer in the mammal. Techniques for administering radiation therapy are known in the art, and these techniques can be used in the combination therapy described herein. The amount and administration of a compound of the invention in this combination therapy can be determined according to the means for ascertaining effective amounts, doses and routes of such compounds as described herein. It is believed that the compounds of the present invention can render abnormal cells more sensitive to treatment with radiation for purposes of killing and/or inhibiting the growth of such cells. Accordingly, this invention relates to a method for sensitizing abnormal cells in a mammal to treatment with radiation which comprises administering to the mammal an amount of a compound of the present invention which amount is effective in sensitizing abnormal cells to treatment with radiation.

It is still another aspect of the invention to provide a method for inhibiting abnormal cell growth in a mammal which comprises an amount of a compound of the present invention or an isotopically-labeled derivative thereof, and an amount of one or more substances selected from anti-angiogenesis agents, signal transduction inhibitors, and anti-proliferative agents.

The disclosed compounds of the formula I can be administered in combination with other known therapeutic agents, including anticancer agents. As used here, the term "anticancer agent" relates to any agent which is administered to a patient with cancer for the purposes of treating the cancer.

The anti-cancer treatment defined above may be applied as a monotherapy or may involve, in addition to the herein disclosed compounds of formula I, conventional surgery or radiotherapy or medicinal therapy. Such medicinal therapy, e.g. a chemotherapy or a targeted therapy, may include one or more, but preferably one, of the following anti-tumor agents:

Alkylating agents: such as altretamine, bendamustine, busulfan, carmustine, chlorambucil, chlormethine, cyclophosphamide, dacarbazine, ifosfamide, improsulfan, tosilate, lomustine, melphalan, mitobronitol, mitolactol, nimustine, ranimustine, temozolomide, thiotepa, treosulfan, mechloretamine, carboquone; apaziquone, fotemustine, glufosfamide, palifosfamide, pipobroman, trofosfamide, uramustine, TH-302[4], VAL-083[4];

Platinum Compounds: such as carboplatin, cisplatin, eptaplatin, miriplatine hydrate, oxaliplatin, lobaplatin, nedaplatin, picoplatin, satraplatin; lobaplatin, nedaplatin, picoplatin, satraplatin;

DNA altering agents: such as amrubicin, bisantrene, decitabine, mitoxantrone, procarbazine, trabectedin, clofarabine; amsacrine, brostallicin, pixantrone, laromustine[1,3];

Topoisomerase Inhibitors: such as etoposide, irinotecan, razoxane, sobuzoxane, teniposide, topotecan; amonafide, belotecan, elliptinium acetate, voreloxin;

Microtubule modifiers: such as cabazitaxel, docetaxel, eribulin, ixabepilone, paclitaxel, vinblastine, vincristine, vinorelbine, vindesine, vinflunine; fosbretabulin, tesetaxel;

Antimetabolites: such as asparaginase[3], azacitidine, calcium levofolinate, capecitabine, cladribine, cytarabine, enocitabine, floxuridine, fludarabine, fluorouracil, gemcitabine, mercaptopurine, methotrexate, nelarabine, pemetrexed, pralatrexate, azathioprine, thioguanine, carmofur; doxifluridine, elacytarabine, raltitrexed, sapacitabine, tegafur[2,3], trimetrexate;

Anticancer antibiotics: such as bleomycin, dactinomycin, doxorubicin, epirubicin, idarubicin, levamisole, miltefosine, mitomycin C, romidepsin, streptozocin, valrubicin, zinostatin, zorubicin, daunorubicin, plicamycin; aclarubicin, peplomycin, pirarubicin;

Hormones/Antagonists: such as abarelix, abiraterone, bicalutamide, buserelin, calusterone, chlorotrianisene, degarelix, dexamethasone, estradiol, fluocortolone fluoxymesterone, flutamide, fulvestrant, goserelin, histrelin, leuprorelin, megestrol, mitotane, nafarelin, nandrolone, nilutamide, octreotide, prednisolone, raloxifene, tamoxifen, thyrotropin alfa, toremifene, trilostane, triptorelin, diethylstilbestrol; acolbifene, danazol, deslorelin, epitiostanol, orteronel, enzalutamide[1,3];

Aromatase inhibitors: such as aminoglutethimide, anastrozole, exemestane, fadrozole, letrozole, testolactone; formestane;

Small molecule kinase inhibitors: such as crizotinib, dasatinib, erlotinib, imatinib, lapatinib, nilotinib, pazopanib, regorafenib, ruxolitinib, sorafenib, sunitinib, vandetanib, vemurafenib, bosutinib, gefitinib, axitinib; afatinib, alisertib, dabrafenib, dacomitinib, dinaciclib, dovitinib, enzastaurin, nintedanib, lenvatinib, linifanib, linsitinib, masitinib, midostaurin, motesanib, neratinib, orantinib, perifosine, ponatinib, radotinib, rigosertib, tipifarnib, tivantinib, tivozanib, trametinib, pimasertib, brivanib alaninate, cediranib, apatinib[4], cabozantinib S-malate[1,3], ibrutinib[1,3], icotinib[4], buparlisib[2], cipatinib[4], cobimetinib[1,3], idelalisib[1,3], fedratinib[1], XL-647[4];

Photosensitizers: such as methoxsalen[3]; porfimer sodium, talaporfin, temoporfin;

Antibodies: such as alemtuzumab, besilesomab, brentuximab vedotin, cetuximab, denosumab, ipilimumab, ofatumumab, panitumumab, rituximab, tositumomab, trastuzumab, bevacizumab, pertuzumab[2,3]; catumaxomab, elotuzumab, epratuzumab, farletuzumab, mogamulizumab, necitumumab, nimotuzumab, obinutuzumab, ocaratuzumab, oregovomab, ramucirumab, rilotumumab, siltuximab, tocilizumab, zalutumumab, zanolimumab, matuzumab, dalotuzumab[1,2,3], onartuzumab[1,3], racotumomab[1], tabalumab[1,3], EMD-525797[4], nivolumab[1,3];

Cytokines: such as aldesleukin, interferon alfa[2], interferon alfa2a[3], interferon alfa2b[2,3]; celmoleukin, tasonermin, teceleukin, oprelvekin[1,3], recombinant interferon beta-1a[4];

Drug Conjugates: such as denileukin diftitox, ibritumomab tiuxetan, iobenguane I123, prednimustine, trastuzumab emtansine, estramustine, gemtuzumab, ozogamicin, aflibercept; cintredekin besudotox, edotreotide, inotuzumab ozogamicin, naptumomab estafenatox, oportuzumab monatox, technetium (99mTc) arcitumomab[1,3], vintafolide[1,3];

Vaccines: such as sipuleucel[3]; vitespen[3], emepepimut-S[3], oncoVAX[4], rindopepimut[3], troVax[4], MGN-1601[4], MGN-1703[4]; and Miscellaneous: alitretinoin, bexarotene, bortezomib, everolimus, ibandronic acid, imiquimod, lenalidomide, lentinan, metirosine, mifamurtide, pamidronic acid, pegaspargase, pentostatin, sipuleucel[3], sizofiran, tamibarotene, temsirolimus, thalidomide, tretinoin, vismodegib, zoledronic acid, vorinostat; celecoxib, cilengitide, entinostat, etanidazole, ganetespib, idronoxil, iniparib, ixazomib, lonidamine, nimorazole, panobinostat, peretinoin, plitidepsin, pomalidomide, procodazol, ridaforolimus, tasquinimod, telotristat, thymalfasin, tirapazamine, tosedostat, trabedersen, ubenimex, valspodar, gendicine[4], picibanil[4], reolysin[4], retaspimycin hydrochloride[1,3], trebananib[2,3], virulizin[4], carfilzomib[1,3], endostatin[4], immucothel[4], belinostat[3], MGN-1703[4].

([1] Prop. INN (Proposed International Nonproprietary Name); [2] Rec. INN (Recommended International Nonproprietary Names); [3] USAN (United States Adopted Name); [4] no INN).

The above teaching of the invention and its embodiments is valid and applicable without restrictions to the methods of treatment if expedient.

In the scope of the present invention, novel azaquinazoline carboxamide compounds of formula (I) are provided for the first time. The p70S6K inhibitors of the invention are structurally distinct from compounds in the art because of introducing heteroatoms into the quinazoline carboxamide scaffold. The invention comprises the use of compounds of formula (I) in the regulation, modulation and/or inhibition of the PI3K signal cascade via p70S6K, which a member of said pathway. The compounds of the invention can be advantageously applied as research tool, for diagnosis and/or in treatment of any disorders that are responsive to p70S6K signaling and inhibition.

For example, the compounds of the invention are useful in-vitro as unique tools for understanding the biological role of p70S6K, including the evaluation of the many factors thought to influence, and be influenced by, the production of p70S6K. The present compounds are also useful in the development of other compounds that interact with p70S6K since the present compounds provide important structure-activity relationship (SAR) information that facilitate that development.

The compounds of the invention are potent, selective and orally bioavailable p70S6K inhibitors that address this unmet medical need for the several conditions, particularly cancer and inflammation, with respect to the progressive features of the diseases. Medicaments and pharmaceutical compositions containing said compounds and the use of said compounds to treat p70S6K-mediated conditions is a promising, novel approach for a broad spectrum of therapies causing a direct and immediate improvement in the state of health, whether in man and animal. The impact is of special benefit to efficiently combat hyperproliferative disorders, either alone or in combination with other treatments.

Due to the surprisingly appreciable inhibitory activity on p70S6K, the compounds of the invention can be advantageously administered at lower doses compared to other less potent or selective inhibitors of prior art while still achieving equivalent or even superior desired biological effects. In addition, such a dose reduction advantageously leads to less or even no medicinal adverse effects. Moreover, the compounds of formula (I), their salts, isomers, tautomers, enantiomeric forms, diastereomers, racemates, derivatives, prodrugs and/or metabolites are characterized by a high specificity and stability, low manufacturing costs and convenient handling. These features form the basis for a reproducible action, wherein the lack of cross-reactivity is included, and for a reliable and safe interaction with the target structure.

All the references cited herein are incorporated by reference in the disclosure of the invention hereby.

It is to be understood that this invention is not limited to the particular compounds, pharmaceutical compositions, uses and methods described herein, as such matter can, of course, vary. It is also to be understood that the terminology used herein is for the purpose of describing particular embodiments only and is not intended to limit the scope of the present invention, which is only defined by the appended claims. As used herein, including the appended claims, singular forms of words such as "a," "an," and "the" include their corresponding plural referents unless the context clearly dictates otherwise. Thus, e.g., reference to "a compound" includes a single or several different compounds, and reference to "a method" includes reference to equivalent steps and methods known to a person of ordinary skill in the art, and so forth. Unless otherwise defined, all technical and scientific terms used herein have the same meaning as commonly understood by a person of ordinary skill in the art to which this invention belongs.

The techniques that are essential according to the invention are described in detail in the specification. Other techniques which are not described in detail correspond to known standard methods that are well known to a person skilled in the art, or the techniques are described in more detail in cited references, patent applications or standard literature. Although methods and materials similar or equivalent to those described herein can be used in the practice or testing of the present invention, suitable examples are described below. The following examples are provided by way of illustration and not by way of limitation. Within the examples, standard reagents and buffers that are free from contaminating activities (whenever practical) are used. The example are particularly to be construed such that they are not limited to the explicitly demonstrated combinations of features, but the exemplified features may be unrestrictedly combined again if the technical problem of the invention is solved. Similarly, the features of any claim can be combined with the features of one or more other claims.

In the following examples, "conventional workup" means: water was added if necessary, the pH was adjusted, if necessary, to a value of between 2 and 10, depending on the constitution of the end product, the mixture was extracted with ethyl acetate or dichloromethane, the phases were separated, the organic phase was dried over sodium sulfate and evaporated, and the product was purified by chromatography on silica gel or C-18, and/or by crystallization.

Some abbreviations that may appear in this application are as follows:

| | |
|---|---|
| ACN | acetonitrile |
| AcOH | Acetic acid |
| AIBN | Azobisisobutylonitrile |
| ATP | Adenosine triphosphate |
| b | Broad peak |
| Bop-Cl | Bis(2-oxo-3-oxazolidinyl)phosphinic chloride |
| Conc. | concentrated |
| d | Doublet |
| DCM | Dichloromethane |
| DCE | dichloroethane |
| DMAP | dimethylaminopyridine |
| DMF | dimethylformamide |
| DMSO | dimethylsulfoxide |
| DIEA/DIPEA | N,N-Diisopropylethylamine |
| DTT | dithiothreitol |
| EDTA | Ethylenediaminetetraacetic acid |
| equiv./eq. | equivalents |
| Et | ethyl |
| h | hour |
| HEPES | 4-(2-hydroxyethyl)-1-piperazineethanesulfonic acid |
| HPLC | High pressure liquid chromatography |
| LC/MS | Liquid chromatography coupled to mass spectrometry |
| LiOH | Lithium hydroxide |
| m | multiplet |
| M | Molecular ion |
| m/z | Mass-to-charge ratio |
| Me | methyl |
| MeOH | methanol |
| min | minute |

| | |
|---|---|
| MS | Mass spectrometry |
| N | Normal (unit of concentration) |
| NaOH | Sodium hydroxide |
| NBS | N-bromosuccinimide |
| NMO | 4-methylmorpholine N-oxide |
| NMP | N-Methyl-2-pyrrolidone |
| NMR | Nuclear Magnetic Resonance |
| PG | Protecting group |
| psi | Pounds per square inch |
| PyBOP | (Benzotriazol-1-yloxy)tripyrrolidinophosphonium hexafluorophosphate |
| q | Quartette (or quartet) |
| Rf | Retention factor |
| RT/rt | Room temperature |
| Rt. | Retention time |
| s | Singlet |
| T3P | Propylphosphonic anhydride |
| TBAF | Tetrabutylammonium fluoride |
| Tert | Tertiary |
| TEA | Triethylamine |
| TFA | Trifluoroacetic acid |
| THAB | Tetrahexylammonium bromide |
| THF | Tetrahydrofuran |
| UV | ultraviolet |
| VIS | visible |

NMR Spectra

NMR Spectra were acquired on a Varian $^{Unity}$Inova or Bruker 400 MHz NMR spectrometer equipped with an Automation Triple Broadband (ATB) probe. The ATB probe was simultaneously tuned to $^1$H, $^{19}$F and $^{13}$C. For typical $^1$H NMR spectra, the pulse angle was 45 degrees, 8 scans were summed and the spectral width was 16 ppm (−2 ppm to 14 ppm). A total of 32768 complex points were collected during the 5.1 second acquisition time, and the recycle delay was set to 1 second. Spectra were collected at 25° C. $^1$H NMR Spectra are typically processed with 0.2 Hz line broadening and zero-filling to 131072 points prior to Fourier transformation.

Analytical LC/MS was performed using the following three methods:

Method A: A Discovery $C^{18}$, 5 µm, 3×30 mm column was used at a flow rate of 400 µL/min, sample loop 5 µL, mobile phase: (A) water with 0.1% formic acid, mobile phase, (B) methanol with 0.1% formic acid; retention times are given in minutes. Method details: (I) runs on a Quaternary Pump G1311A (Agilent) with UV/VIS diode array detector G1315B (Agilent) and Finnigan LCQ Duo MS detector in ESI+ modus with UV-detection at 254 and 280 nm with a gradient of 15-95% (B) in a 3.2 min linear gradient; (11) hold for 1.4 min at 95% (B); (111) decrease from 95-15% (B) in a 0.1 min linear gradient; (IV) hold for 2.3 min at 15% (B).

Method B: A Waters Symmetry $C^{18}$, 3.5 µm, 4.6×75 mm column at a flow rate of 1 mL/min, sample loop 10 µL, mobile phase (A) is water with 0.05% TFA, mobile phase (B) is ACN with 0.05% TFA; retention times are given in minutes. Methods details: (I) runs on a Binary Pump G1312A (Agilent) with UV/Vis diode array detector G1315B (Agilent) and Agilent G1956B (SL) MS detector in ESI+ mode with UV-detection at 254 and 280 nm with a gradient of 20-85% (B) in a 10 min linear gradient; (II) hold for 1 min at 85% (B); (Ill) decrease from 20-85% (B) in a 0.2 min linear gradient; (IV) hold for 3.8 min at 20% (B).

Method C: Gradient: 4.2 min; Flow: 2 ml/min; 99:1-0:100 Water+0.1% (Vol.) TFA, Acetonitril+0.1% (Vol.) TFA; (i) 0.0 to 0.2 min: 99:1; (ii) 0.2 to 3.8 min: 99:1→0:100; (iii) 3.8 to 4.2 min: 0:100; Column: Chromolith Performance RP18e; 100 mm long, 3 mm diameter; Wavelength: 220 nm.

Analytical Chiral HPLC

Analytical chiral HPLC was performed using a ChiralPak AD-H column (250×4.6 mm) from Daicel Chemical Industries, Ltd. on an Agilent 1100 Series system. The method used a 5.0 µL injection volume, with a flow rate of 1 mL/min of 100% methanol for 15 min at 25° C., and UV-detection at 254 and 280 nm.

Preparative HPLC

Preparative HPLC was performed using either a Waters Atlantis $dC_{18}$ OBD 10 µM (30×250 mm) column or a Waters Sunfire Prep $C_{18}$ OBD 10 µM (30×250 mm) column. The columns were used at a flow rate of 60 mL/min on a Waters Prep LC 4000 System equipped with a sample loop (10 mL) and an ISCO UA-6 UV/Vis detector. The mobile phase was drawn from two solvent reservoirs containing (A) water and (B) HPLC-grade acetonitrile. A typical preparative run used a linear gradient (e.g., 0-60% solvent B over 60 min).

The present invention also relates to processes for manufacturing the compounds according to the hereinafter described schemes and working examples.

General Synthetic Schemes

Scheme 1A: Alcohol intermediate A (WO12/69146) was converted to the corresponding mesylate, which was then reacted with a secondary alkyl amine followed by Boc-deprotection with hydrochloric acid afforded the desired amine hydrochloride salt intermediate B.

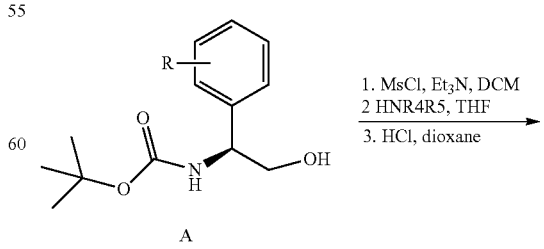

-continued

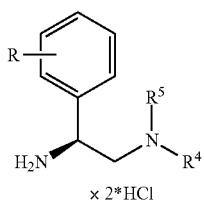

B

Scheme 1B: Nucleophilic attack of intermediate C (WO12/69146) with a secondary alkyl amine followed by Boc-deprotection with hydrochloric acid afforded the desired amine hydrochloride salt intermediate B.

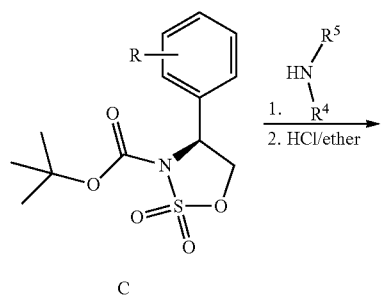

C

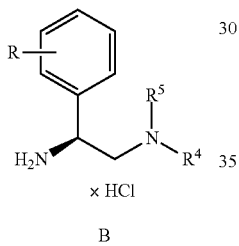

B

Scheme 2: Nucleophilic attack of intermediate C (WO12/69146) with a nosyl-protected primary amine followed by Boc-deprotection with hydrochloric acid afforded the desired amine hydrochloride salt intermediate D.

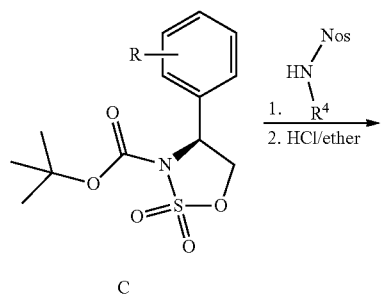

C

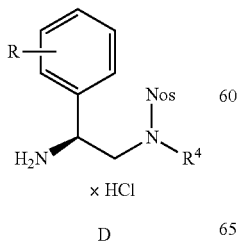

D

Scheme 3: 2-Nitro-m-xylene was treated with potassium permanganate in the presence of NaOH in water to afford 2-nitroisophthalic acid intermediate. The diacid was refluxed with thionyl chloride in DMF, followed by addition of aqueous ammonia in THF to give 2-nitro isophthalamide, which was then hydrogenated using Pd/C to give the 2-amino isophthlalamide intermediate. Cyclization of 2-amino isophthalamide proceeded in DMF using sodium nitrite in 0.5M Hydrochloric acid gave the desired 4-Oxo-3,4-dihydro-benzo[d][1,2,3]triazine-8-carboxamide E.

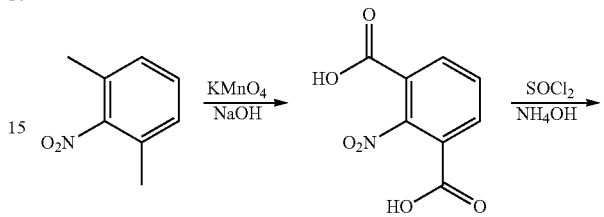

E

Scheme 4: A mixture of dimethyl 3-oxopentanedioate, triethoxymethane and urea in toluene was refluxed to afford dimethyl 4-oxo-1,4-dihydropyridine-3,5-dicarboxylate as a precipitate. This intermediate was then refluxed in phosphoryl chloride to give the 4-chloropyridine intermediate. The solution of diester and formimidamide acetate in 1,4-dioxane were treated with sodium hydride to afford 4-hydroxypyrido[4,3-d]pyrimidine-8-carboxamide F.

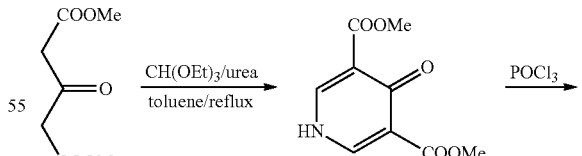

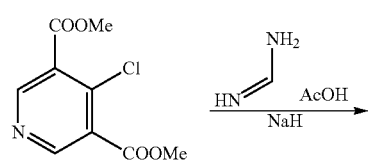

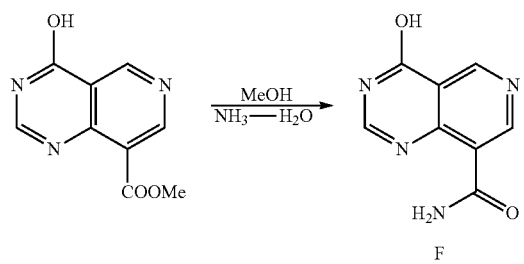

Scheme 5: The nitropyridine was treated with potassium permanganate to afford the desired diacid, which was then treated with iodoethane to give the diethyl ester derivative. Palladium-catalyzed hydrogenation of the nitropyridyl diester afforded the aminopyridine diester which was then cyclized by treatment with formamide to give a mixture of both G (major product) and H (minor product) which was used without separation.

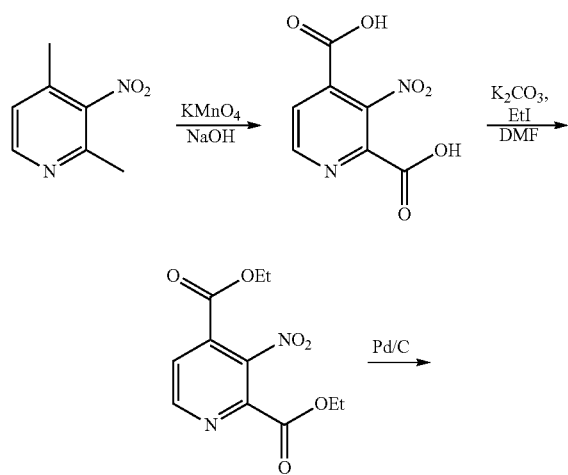

Scheme 6: The amino pyridine derivative was treated with concentrated sulfuric acid and sodium nitrite affording the pyridone derivative which was then treated with phosphorus oxybromide to give the bromo pyridine intermediate. The bromo pyridine was treated with copper cyanide to provide the nitrile derivative followed by hydrolysis with sulfuric acid to afford the amide derivative. The reduction of the resultant amide derivative with iron powder afforded the desired aminopyridine. The aminopyridine derivative was refluxed in excess of triethylorthoformate yielding the desired pyridopyrimidinone intermediate, which was treated with sulfuric acid and potassium dichromate to yield the desired acid.
The acid was treated with carbonyldiimidazole in dimethylformamide followed by the addition of either ammonia to afford the desired 4-hydroxypyrido[3,2-d]pyrimidine-8-carboxamide G or methanol to yield the desired methyl 4-hydroxypyrido[3,2-d]pyrimidine-8-carboxylate I.

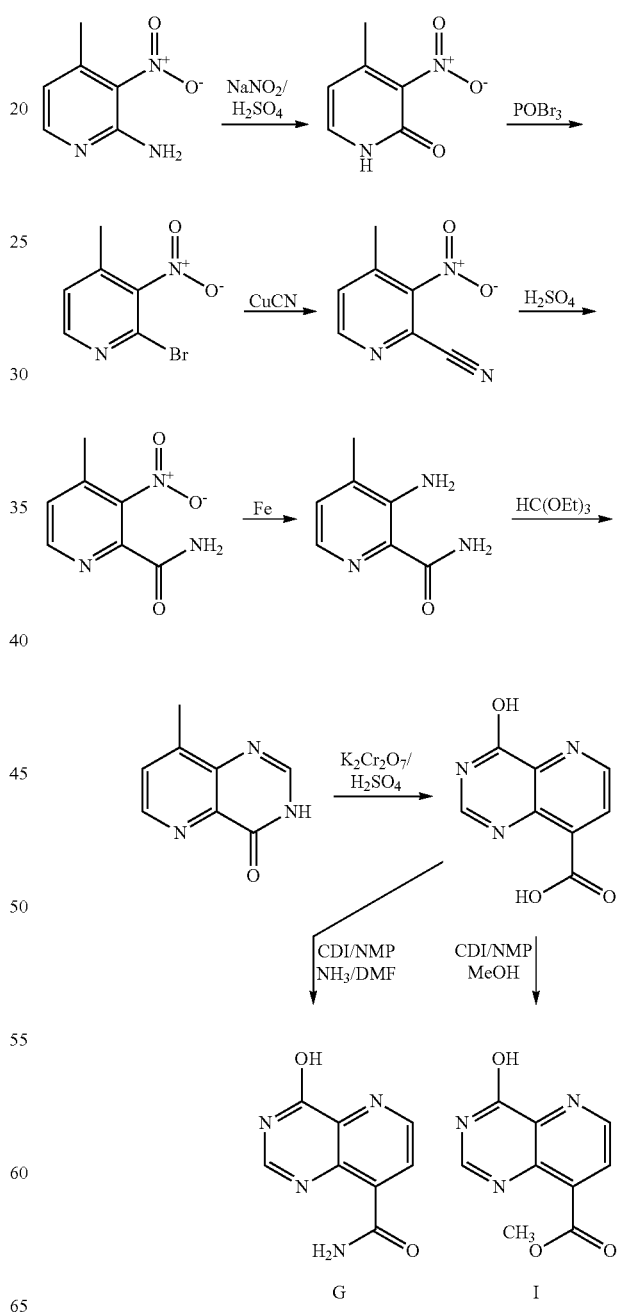

Scheme 7: Aza-quinazoline carboxamide intermediate J was reacted with amine intermediate K in the presence of DIEA and PyBop in DMSO or DMF or NMP at 50° C. to afford the desired compound L.

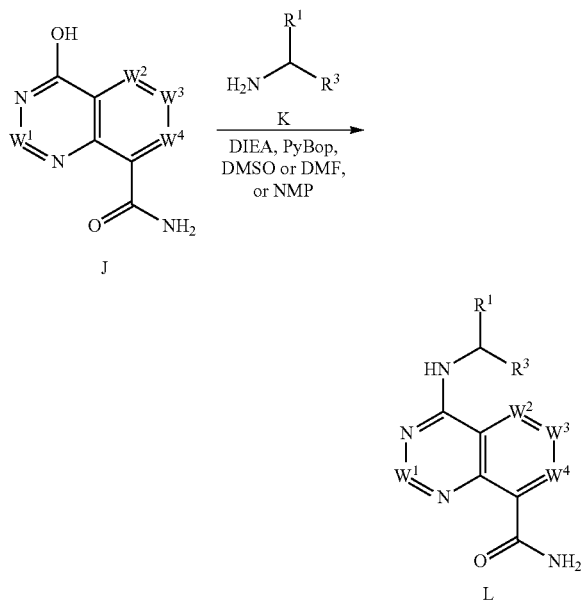

Scheme 8: Aza-quinazoline carboxamide intermediate J was reacted with amine intermediate D in the presence of DIEA and PyBop in DMSO or DMF or NMP at 50° C. afford the nosyl protected intermediate, which was treated with thiophenol in the presence of potassium carbonate to give the desired compound M.

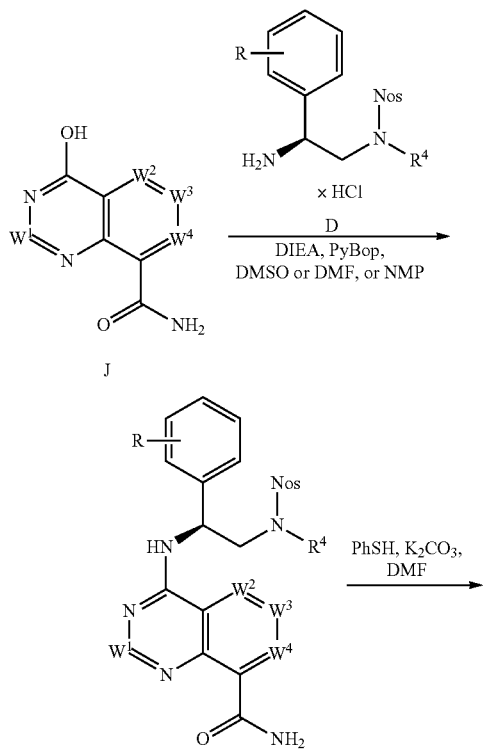

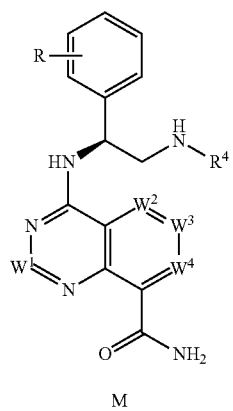

Scheme 9: Aza-quinazoline carboxamide intermediate J was reacted with amine intermediate N in the presence of DIEA and PyBop in DMSO or DMF or NMP at 50° C. afford the Boc-protected intermediate, which was treated with HCl/dioxane solution in MeOH to give the desired compound O.

Scheme 10: Methyl aza-quinazoline carboxylate intermediate was reacted with amine intermediate in the presence of DIEA and PyBop in DMSO at 40° C. afford the nosyl-protected intermediate, which was then converted to its carboxamide intermediate with ammonia in methanol. De-Nosylation with mercaptoacetic acid in the presence of base gave the desired compound M.

Scheme 11: Aza-quinazoline carboxamide intermediate J or Aza-quinazoline nitrile intermediate P was reacted with phosphorus trioxychloride to afford the desired chloride intermediate. Reaction of said chloride intermediate with the appropriate amine affords the desired compound Q (if R' is not Nos) or the nosyl-protected intermediate (if R' = Nos), which was then treated with mercaptoacetic acid in the presence of base to give the desired compound M.

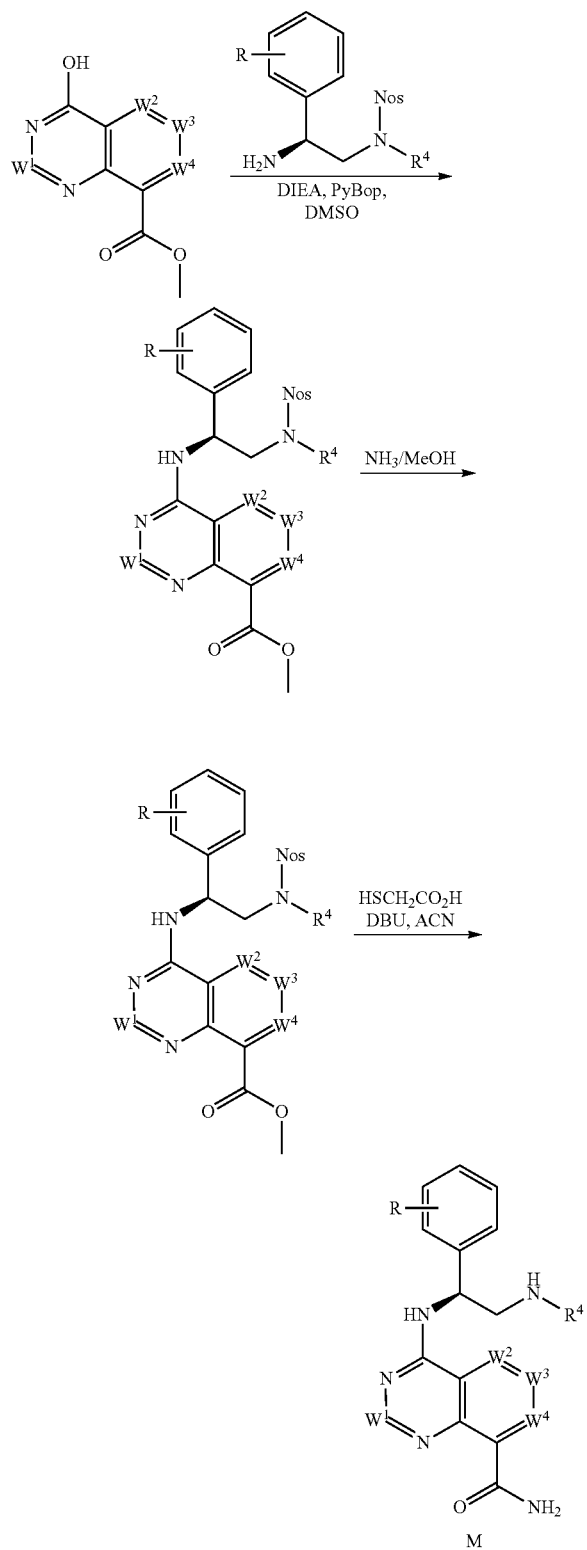

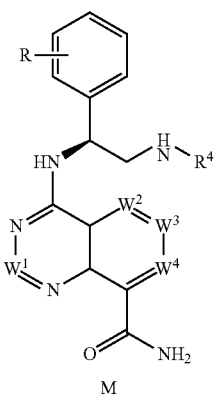

M

Example 1: Synthesis of Intermediates

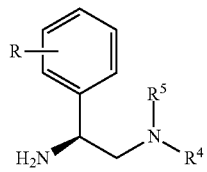

Amino Phenylethanamine Dihydrochloride (B)
(Scheme 1A)

A solution of alcohol intermediate A (3.17 mmol) in DCM (5.00 mL) was cooled to −78° C. and treated with triethylamine (9.52 mmol) and methanesulfonyl chloride (4.76 mmol) then stirred for 30-60 minutes before being quenched with saturated sodium bicarbonate solution (10 mL). The organic layer was extracted with brine, dried over magnesium sulfate, filtered and concentrated to give the corresponding mesylate which was used without further purification.

The mesylate was treated with amine (2-5 eq. if neat; or 1.5 eq. if in THF solution) at room temperature for 30-60 minutes. The resultant desired 2-phenylethan-1,2-diamine was diluted with EtOAc and subjected to aqueous extraction with saturated sodium bicarbonate. The organic layers were washed with brine, dried over magnesium sulfate, filtered and concentrated. The crude residue was then purified under normal phase chromatography (20-50% EtOAc in hexanes on silica gel) to afford the pure desired boc-protected amino phenylethanamine intermediate as a white solid in yield of (55-78%).

A suspension of the Boc-protected amino phenylethanamine intermediate (0.22 mmol) in anhydrous DCM (2 mL) was treated with 4.0 M HCl in 1,4-dioxane (1.1 mmol, 5 eq), and the contents were stirred at room temperature. Dissolution occurred, followed by precipitation of a solid. After 3 hours, the solid was collected by filtration, washed with diethyl ether (10 mL) and dried under vacuum for 2 hours to afford B as a white or off-white solid (63-95%).

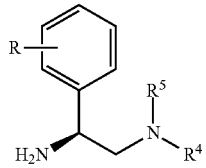

Amino Phenylethanamine Dihydrochloride (B)
(Scheme 1B)

A suspension of the cyclic sulfone intermediate C (52.52 mmol) in CH₃CN (100 mL) was treated with a secondary amine (65.67 mmol, 1.25 eq), and the contents were stirred at room temp for 30-60 minutes. A solid precipitated, which was filtered, washed with MeOH or acetone (100 mL) and dried under vacuum for 2 hours to provide the Boc-protected amino phenylethanamine intermediate (60-77%) as a white solid.

A suspension of the Boc-protected amino phenylethanamine intermediate (38.61 mmol) in anhydrous MeOH (50 mL) was treated with 2.0 M HCl in diethyl ether (200 mmol, 5 eq), and the contents were stirred at room temperature. Dissolution occurred, followed by precipitation of a solid. After 3 hours, the solid was collected by filtration, washed with diethyl ether (100 mL) and dried under vacuum for 2 hours to afford B as a white or off-white solid (69-75%).

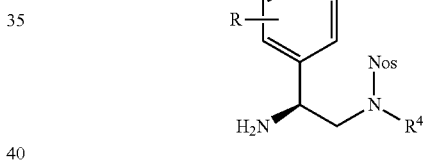

Amino Phenylethanamine Dihydrochloride (D)
(Scheme 2)

N-alkyl-4-nitrobenzenesulfonamide (7.84 mmol) was added to a suspension of powdered potassium hydroxide (15.68 mmol) in CH₃CN (30.00 ml), and the reaction mixture was stirred for 15 minutes. A solution of the cyclic sulfone intermediate C (7.47 mmol) in MeCN (30.00 ml) was added dropwise and the solution was stirred for 12 h. To the reaction mixture was added 0.5 N HCl (50 mL) and the solution was allowed to stir for an additional 15 minutes. A precipitate formed after a few minutes. The solid was collected by filtration, washed with water (50 mL), and dried under vacuum to yield Boc-protected intermediate as a beige solid (50-60%).

A suspension of the Boc-protected intermediate (0.77 mmol) in anhydrous MeOH (1 mL) was treated with 2.0 M HCl in diethyl ether (4.6 mmol, 5 eq), and the contents were stirred at room temperature. Dissolution occurred, followed by precipitation of a solid. After 3 hours, the reaction mixture was diluted with diethyl ether (10 mL) and the solid was collected by filtration, washed with diethyl ether (10 mL) and dried under vacuum to afford D as a beige solid (65-75%).

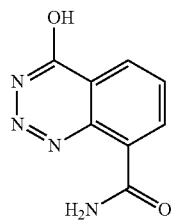 [SMILES: NC(=O)c1cccc2c(O)nnnc12]

4-hydroxybenzo[d][1,2,3]triazine-8-carboxamide (E) (Scheme 3)

2-Nitroisophthalic Acid

A mixture of 2-nitro-m-xylene (10.0 g, 0.066 mol) and sodium hydroxide (2.29 g, 0.072 mol) in water (200 mL) was heated to 90° C. and potassium permanganate (41.0 g, 0.264 mol) was added in lot wise during a period of 3 h. The reaction mixture was heated to 90° C. for 20 h. The reaction mass was filtered through celite bed, washed with hot water (50 mL) and acidified using 6N HCl (pH>1). The solid precipitated out were collected by filtration, washed with water and dried under suction to afford the title compound as the white solid (72% yield). LC-MS [210 (M−H)], $^1$H NMR (400 MHz, DMSO-$d_6$): δ 8.18 (d, J=7.80 Hz, 2H), 7.80 (t, J=7.80 Hz, 1H).

2-Nitro-isophthalamide

A mixture of 2-nitro-isophthalic acid (10.0 g, 0.047 mol), thionyl chloride (100 mL) and DMF (0.1 mL) was heated to reflux for 16 h under nitrogen atmosphere. The reaction mixture was evaporated under reduced pressure. The residue was dissolved in THF (50 mL), cooled to 0° C. and aqueous ammonia (50 mL) was added in drops. The reaction mixture was stirred at RT for 6 h, the solid precipitated out were collected by filtration, washed with water and dried under suction to afford the title compound as the white solid (61% yield). LC-MS [208 (M−H)], $^1$H NMR (400 MHz, DMSO-$d_6$): δ 8.28 (brs, 2H), 7.77 (brs, 2H), 7.74-7.67 (m, 3H).

2-Amino isophthalamide

A mixture of 2-nitro-isophthalamide (6 g, 0.028 mol) and Pd/C (0.6 g) in DMF (100 mL) was hydrogenated at RT under hydrogen bladder pressure for 16 h. The reaction mixture was filtered through celite bed, washed with DMF and filtrate was evaporated under vacuum to afford the title compound as a brown solid (yield 78%). LC-MS [178 (M−H)], $^1$H NMR (400 MHz, DMSO-$d_6$): δ 7.97 (s, 2H), 7.84 (brs, 2H), 7.65 (d, J=7.76 Hz, 2H), 7.22 (brs, 2H), 6.49 (t, J=7.76 Hz, 1H).

4-hydroxybenzo[d][1,2,3]triazine-8-carboxamide

A solution of 2-amino-isophthalamide (4.0 g, 0.022 mol) in DMF (40 mL) was added to a solution of sodium nitrite (1.85 g, 0.0267 mol) in 0.5 M HCl (120 mL) at 0° C. The reaction mixture was stirred at RT for 2 h and evaporated under reduced pressure. The residue was made slurry with water and filtered, dried under suction to afford the title compound C as a white solid (yield 84%). LC-MS [191 (M+H)], $^1$H NMR (400 MHz, DMSO-$d_6$) δ 15.19 (s, 1H), 8.48 (s, 1H), 8.32-8.29 (m, 2H), 7.94 (dd, J=5.5, 14.4 Hz, 2H).

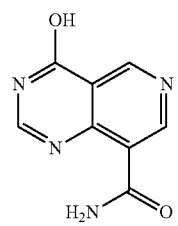 [SMILES: NC(=O)c1cncc2c(O)ncnc12]

4-hydroxypyrido[4,3-d]pyrimidine-8-carboxamide (F) (Scheme 4)

Dimethyl 4-oxo-1,4-dihydropyridine-3,5-dicarboxylate

A mixture of dimethyl 3-oxopentanedioate (12 g, 69 mmol), CH(OEt)3 (15.1 g, 100 mmol) and urea (6 g, 100 mmol) in xylene (25 mL) was heated to reflux for 3 hours. The mixture was cooled to room temperature and the precipitate was filtered, washed with xylene and DCM to afford the title compound as white solid (yield 82.3%).

Dimethyl 4-chloropyridine-3,5-dicarboxylate

A mixture of dimethyl 4-oxo-1,4-dihydropyridine-3,5-dicarboxylate (3 g, crude) and POCl3 (10 mL) was heated to 140° C. in the sealed tube for 15 hours. The mixture was cooled to RT, poured into ice and extracted with ether. The organic layer was washed with brine, dried over Na2SO4, filtered and concentrated to afford the title compound as solid (yield 33.7%).

Methyl 4-hydroxypyrido[4,3-d]pyrimidine-8-carboxylate

To the mixture of dimethyl 4-chloropyridine-3,5-dicarboxylate (0.6 g, 2.6 mmol) and formimidamide acetate (0.82 g, 7.8 mmol) in dioxane (20 mL) was added NaH (0.31 g, 7.8 mmol). The resulting mixture was refluxed for 48 hours, cooled to RT. The precipitate was filtered, and washed with EA to afford the title compound as grey solid (yield 56.1%).

4-hydroxypyrido[4,3-d]pyrimidine-8-carboxamide

The mixture of methyl 4-hydroxypyrido[4,3-d]pyrimidine-8-carboxylate (47 mg, 0.1 mmol), NH4OH (3 mL) and MeOH (10 mL) was heated to reflux for 20 hours in a sealed tube. The mixture was then concentrated and purified by prep-HPLC to afford the title compound as a white solid (yield 41.1%).

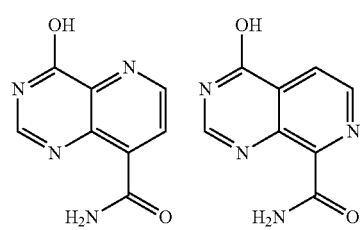

4-hydroxypyrido[3,2-d]pyrimidine-8-carboxamide (G) and 4-hydroxypyrido[3,4-d]pyrimidine-8-carboxamide (H) (Scheme 5)

3-Nitro-pyridine-2,4-dicarboxylic Acid

To a solution of sodium hydroxide (515.24 g; 12881.94 mmol) in water (15.00 l; 30.00 V) was added 2,4-Dimethyl-3-nitro-pyridine (500.00 g; 3220.48 mmol). The mixture was stirred at 90° C. and potassium permanganate (5.25 kg; 32204.85 mmol) was added in small portions and the mixture was heated to reflux while stirred for 16 hours. After cooling to room temperature, the mixture was filtered through celite and washed with water (1 L). The filtrate was evaporated under vacuum to ½th of the original volume with resulting solution cooled ~5° C. HCl (conc., aq.) was added in drops and pH was adjusted to ~2. The product was extracted with EtOAc (5×3 L). The combined organic layer was dried over Na2SO4 and evaporated under vacuum to afford the titled compound as a yellow solid (yield 12.4%). LC-MS [167 (M+H)], $^1$H NMR (400 MHz, DMSO-d6) 14.2 (bs, 2H), 9.0-8.99 (d, 2H), 8.11-8.10 (d, 1H).

3-Nitro-pyridine-2,4-dicarboxylic Acid Diethyl Ester

To a solution of 3-Nitro-pyridine-2,4-dicarboxylic acid (110.00 g; 0.40 mol) in DMF (1100.00 ml; 10.00 V), was added potassium carbonate (170.02 g; 1.19 mol) and iodoethane (94.95 ml; 1.19 mol). The mixture was stirred at ambient temperature for 16 hours. After completion of reaction, the reaction mixture was filtered and the filtrate removed by concentration under vacuum. The residue was taken in ethyl acetate (1 L), filtered again and concentrated under vacuum. The residue was diluted with cold water (1 L) and extracted with diethyl ether (3×1 L). The combined organic layer was washed with water (2×300 mL), dried over $Na_2SO_4$ and concentrated under vacuum. The residue was purified by the column chromatography over silica gel (60-120 mesh) using 5-10% EtOAc: Hexanes to afford the titled compound as a brown liquid (yield 51.6%). LC-MS [269 (M+H)], $^1$HNMR (400 MHz, CDCl3) 8.94-8.93 (d, 1H), 8.00-7.98 (d, 1H), 4.48-4.38 (m, 4H), 1.41-1.38 (m, 6H).

3-Amino-pyridine-2,4-dicarboxylic Acid Diethyl Ester

To a solution of 3-Nitro-pyridine-2,4-dicarboxylic acid diethyl ester (55.00 g; 0.19 mol) was added Palladium on carbon (10% w/w) (6.00 g; 0.01 mol). The mixture was stirred at room temperature for 4 hours under 5 Kg of hydrogen pressure. After completion of the reaction, the reaction mixture was filtered through celite and the filtrate concentrated under vacuum. The residue was purified by column chromatography (60-120 mesh) using 15-20% EtOAc: petroleum ether to afford the title compound as a yellow solid (yield 69.7%). LC-MS [239 (M+H)], $^1$H NMR (400 MHz, DMSO-d6), 7.94-7.93 (d, 1H), 7.84-7.83 (d, 1H), 4.34-4.27 (m, 4H), 1.33-1.29 (m, 6H)

4-Hydroxy-pyrido[3,2-d]pyrimidine-8-carboxylamide (G) and 4-Hydroxy-pyrido[3,4-d]pyrimidine-8-carboxylamide (H)

A solution of 3-Amino-pyridine-2,4-dicarboxylic acid diethyl ester (30.00 g; 0.13 mol) in formamide (150.00 ml; 5.00 V) was stirred at 140° C. for 4 days. The reaction mixture was cooled to 0° C. After 5 hours stirring at 0° C., the reaction mixture was filtered and the collected solids were washed with water (20 mL). A slurry was made with the solids in IPA (20 mL), filtered and again washed with IPA, then dried under suction to afford a mixture of the title compounds (G, major product) and (H, minor product) as a gray solid (yield 50.1%). LC-MS [189 (M–H)], $^1$H NMR (400 MHz, DMSO-d6) 12.42 (bs, 1H), 9.33 (s, 1H), 8.88-8.87 (d, 1H), 8.33 (s, 1H), 8.21-8.20 (d, 1H), 8.13 (s, 1H)

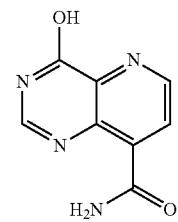

4-hydroxypyrido[3,2-d]pyrimidine-8-carboxamide (G) (Scheme 6)

4-methyl-3-nitropyridin-2(1H)-one

2-Amino-4-methyl-3-nitropyridine (120 g, 0.78 mol) was suspended in water (1.6 L), a concentrated sulfuric acid (120 mL) was added dropwise, and the clear yellow solution was cooled to 0° C. in an ice bath. Sodium nitrite (98 g, 1.42 mol) dissolved in water (250 mL) was added slowly bellow the liquid surface of the reaction solution through a long stem funnel. The reaction mixture was stirred at room temperature for 2 h and was boiled up until no further emission of a brown gas was observed. The reaction solution was cooled, filtered, and dried to obtain the title compound (yield 91.6%).

2-bromo-4-methyl-3-nitropyridine

The 4-methyl-3-nitropyridin-2(1H)-one (110 g, 0.71 mol) was suspended in dichloroethane (1 L). The solution of phosphorus oxybromide (317 g, 1.1 mol) in dichloroethane (1 L) was added dropwise thereto at the ambient temperature. The reaction mixture was refluxed for 12 hours. The mixture was allowed to cool to room temperature, poured into ice water, and neutralized with potassium carbonate. The organic layer was separated, washed with water and brine, and dried over sodium sulfate. The solvent was evaporated to provide the thtile compound (yield 71.8%).

4-methyl-3-nitropicolinonitrile

The bromopyridine (110 g, 0.51 mol) and freshly prepared copper cyanide (50 g, 0.56 mol) were heated in DMF (1 L) at 100° C. for 13 hours. The reaction mixture was allowed to cool to room temperature and poured into a mixture EtOAc/H2O (1.5 L: 3 L). Obtained triphasic mixture was filtered from inorganic solid material. Organic phase was separated, washed with water and dried over sodium sulfate. The solvent was evaporated to provide the title compound (yield 63.7%).

4-methyl-3-nitropicolinamide

The nitrile derivative (106 g, 0.65 mol) was carefully dissolved in 90% sulfuric acid (350 mL). The reaction mixture was heated at 70° C. for 3 hours. Then the reaction mixture was allowed to cool to room temperature and was poured into crushed. The precipitated amide was filtered and dried under reduced pressure (yield 59.5%).

3-amino-4-methylpicolinamide

Three-necked round bottom flask (4 L) quipped with mechanical stirred bar and condenser was charged with nitro derivative (70 g, 0.39 mol) dissolved in i-PrOH (2 L). NH4Cl (7 g), HCl (7 mL), H2O (7 mL) was added thereto. The reaction mixture was heated up to reflux. Iron powder (156 g, 2.8 mol) was added in small portions. After full consumption of starting material, sodium carbonate (106 g, 2.8 mol) was added in small portions. The hot reaction mixture was filtered; insoluble material was washed with hot ethanol several times. The solvent was evaporated to provide the pure amineproduct (yield 61.5%).

8-methylpyrido[3,2-d]pyrimidin-4(3H)-one

The amine derivative (37 g, 0.24 mol) was refluxed in excess of triethylorthoformate (500 mL) for 24 hours. The precipitate was collected, washed with MTBE to obtain the title compound (yield 90.5%).

4-oxo-3,4-dihydropyrido[3,2-d]pyrimidine-8-carboxylic Acid

Two-necked round bottom flask (2 L) equipped with mechanical stirred bar was charged with 98% conc. sulfuric acid (350 mL, d=1.98). The pyrmidinone (35 g, 217 mmol) was carefully added to the mixture. Potassium dichromate (95.8 g, 0.33 mol) was added portionwise to reaction mixture maintaining the temperature between 20-30° C. The reaction mixture was stirred at room temperature overnight. Crushed ice (1.5 kg) was added to the reaction mixture in small portions maintaining the temperature in the 20-30° C. range. Potassium carbonate was added portionwise to pH 1. The formed precipitate was filtered, washed with water and dried under reduced pressure to the title compound (yield 72.4%).

4-Hydroxy-pyrido[3,2-d]pyrimidine-8-carboxylamide

The acid intermediate (8.3 g, 43 mmol) was dissolved in DMF (200 mL) and CDI (8.8 g, 54 mmol) was added thereto. The reaction mixture was warmed to 70° C. and gas evolution was observed. After completion gas evolution the reaction mixture was heated at the same temperature for additional hour to provide a clear solution. Aqueous 25% ammonia (30 ml, 10 eq.) was added and the reaction mixture was heated at 70° C. overnight. The reaction mixture was allowed to cool to room temperature and the solvent was evaporated under reduced pressure. The residue was diluted with water, filtered, washed with water and dried under reduced pressure to provide the title compound (yield 81.9%).

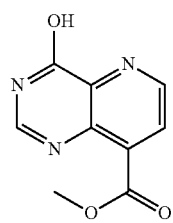

Methyl 4-hydroxypyrido[3,4-d]pyrimidine-8-carboxylate (I) (Scheme 6)

The 4-oxo-3,4-dihydropyrido[3,2-d]pyrimidine-8-carboxylic acid (39.0 g, 0.20 mol) was dissolved in anhydrous NMP (700 mL) and CDI (41.3 g, 0.26 mol, 10 eq.) was added. The reaction mixture was warmed to 70° C. and gas evolution was observed. After completion gas evolution the reaction mixture was heated at the same temperature for additional hour to provide a clear solution. Methanol (65 g, 2 mol) was added thereto and the reaction mixture was heated at 70° C. overnight. The reaction mixture was allowed to cool to room temperature and the organic material was precipitated. It was filtered, washed with methanol and dried under reduced pressure to provide the title compound (I) (yield 75.0%).

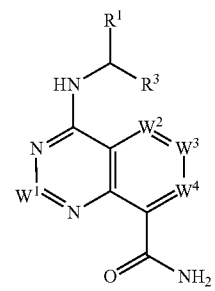

4-substituted-aza-quinazolin-8-carboxamide (L) (Scheme 7)

A mixture of aza-quinazoline carboxamide J (0.21 mmol), amine intermediate K (0.21 mmol), and DIEA (0.86 mmol) were suspended in the solvent (DMF or NMP or DMSO) (2.00 mL) under Ar. The reaction mixture was stirred at rt for 5 min before the addition of PyBOP (0.59 mmol). The reaction was stirred at room temperature for 12 h. The reaction mixture was diluted with water (10 mL) and extracted with EtOAc (3×10 mL). The combined organics were dried over sodium sulfate and concentrated. The residue was purified by either reverse phase HPLC or Biotage to give the desired product L as an off-white solid (11-40%).

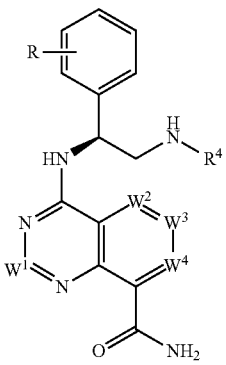

4-substituted-aza-quinazolin-8-carboxamide (M) (Scheme 8)

A mixture of nosyl-protected amine D (0.34 mmol), aza-quinazoline carboxamide J (0.44 mmol), and DIEA (0.68 mmol) were suspended in DMSO (3.00 mL) under Ar. The reaction mixture was stirred at rt for 5 min before addition of PyBOP (0.44 mmol). The reaction was stirred at 40° C. for 12 h. The reaction mixture was filtered and purified by either reverse phase HPLC or Biotage to give the desired nosyl-protected intermediate as an off-white solid (40-92%).

To the solution of the nosyl-protected intermediate (0.38 mmol) in DMF (3.00 ml) was added potassium carbonate (1.13 mmol) and the suspension was stirred for 10 minutes.

Benzenethiol (1.51 mmol) was added via syringe and the solution was stirred vigorously at room temperature overnight. The reaction mixture was filtered and purified by either reverse phase HPLC or Biotage to give the desired product M as a white solid (65-85%).

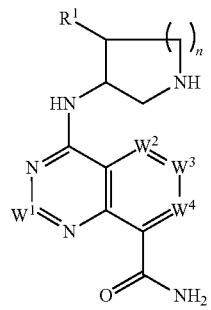

4-substituted-aza-quinazolin-8-carboxamide (O)
(Scheme 9)

A mixture of Boc-protected amine N (0.53 mmol), aza-quinazoline carboxamide J (0.53 mmol), DIEA (1.58 mmol) and PyBOP (0.79 mmol) were suspended in DMSO (2.00 mL) under Ar. The reaction was stirred at 50° C. for 18 h. The reaction mixture was partitioned between EtOAc (25 mL) and saturated sodium bicarbonate solution (5 mL) and phases were separated. The organic phase was washed 4× with water (5 mL) and with brine. The organic layer was dried with sodium sulfate, filtered and concentrated. The reaction mixture was purified on Si-gel with Biotage (EtOAC/hexanes) to give the desired Boc-protected intermediate as an off-white solid (26-48%).

To the solution of the Boc-protected intermediate (0.12 mmol) in methanol (1.5 ml) at room temperature was added 4N HCl in 1,4-dioxane (0.50 mL) and the suspension was stirred for 1 hour. The reaction mixture was filtered and purified by reverse phase HPLC to give the desired products O as a white solid (44-72%).

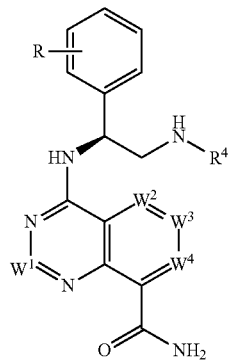

4-substituted-aza-quinazolin-8-carboxamide (M)
(Scheme 10)

A mixture of methyl aza-quinazoline carboxylate (2.4 mmol), DIEA (4.8 mmol) and PyBOP (2.9 mmol) were suspended in DMSO (10 mL) under Ar. The reaction mixture was stirred at rt for 10 min before the addition of nosyl-protected amine (2.4 mmol). The reaction was stirred at 40° C. overnight. After cooling to RT, the reaction was diluted with EtOAc and washed with saturated sodium bicarbonate solution. The separated organic phase was washed with 1M HCl (1×), followed by water (4×), and then brine (1×). The organic phase was dried over Na2SO4, filtered and concentrated in vacuo to give the crude, which was purified on Biotage to give the desired methyl ester intermediate as an light yellow foam (50-65%).

The reaction mixture of the methyl ester intermediate (1.5 mmol) in 7N ammonia in MeOH (12 mL) was stirred at rt overnight. The reaction mixture was concentrated to yield the desired nosyl-protected amide intermediate (80-85%).

To the solution of the nosyl-protected amide intermediate (0.6 mmol) in acetonitrile (2 mL) was added DBU (1.8 mmol) and mercaptoacetic acid (0.9 mmol). The reaction mixture was stirred at room temperature overnight. The reaction was concentrated and dissolved in DCM, which was washed with saturated sodium bicarbonate solution followed by brine. The organic layer was dried over sodium sulfate, filtered and concentrated to yield the crude product. The desired amide M was then isolated via trituration with dichloromethane to give an off-white solid (70-85%).

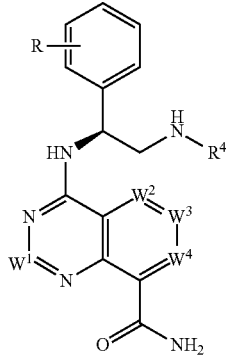

4-substituted-aza-quinazolin-8-carboxamide (Q)
(Scheme 11)

The aza-quinazoline carboxamide J (1.92 mmol) was refluxed in phosphoryl chloride (215 mmol) for 12-18 hours. Upon completion, the reaction was concentrated en vacuo by rotary evaporation. The residue was then taken up in cold ethyl acetate and washed with ice cold saturated sodium bicarbonate solution. The organic layer was washed with brine, dried over sodium sulfate, filtered and concentrated to yield the desired bicyclic chloride intermediate as a yellow solid (34-94%).

The amine (8.43 mmol) was suspended in acetonitrile (85 mL) in a clean, dry round bottom flask equipped a magnetic stir bar. To this was added Hunig's base (50 mmol) and sodium sulfate (28 mmol). The resultant suspension was stirred for 5 minutes, then the bicyclic chloride intermediate (8.43 mmol) was added. The reaction mixture was stirred and heated to 40° C. for 12-18 hours. Upon completion, the reaction was concentrated en vacuo by rotary evaporation. The residue was purified by flash chromatography on silica under 20-50% ethyl acetate in hexanes to yield the desire nitrile intermediate as a light yellow solid (24-60%).

To a mixture of nitrile intermediate (1.37 mmol) and sodium hydroxide (5.46 mmol) in isopropyl alcohol (5.00 ml) and minimal DMSO (0.5 mL) was added hydrogen peroxide (8.2 mmol) at room temperature. The mixture was stirred for until completion. The desired amide compound Q was isolated by diluting the reaction mixture with water (20 mL) then filtering the solids (75-95%).

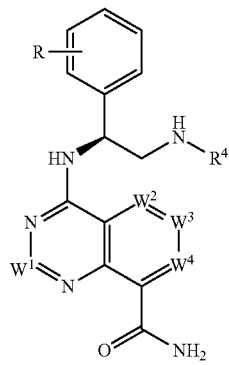

4-substituted-aza-quinazolin-8-carboxamide (M) (Scheme 11)

To the solution of the nosyl protected amide intermediate (5.74 mmol) in acetonitrile (15 mL) was added DBU (17.2 mmol) and mercaptoacetic acid (8.61 mmol). The reaction mixture was stirred at room temperature. Upon completion, the reaction was concentrated and taken up in dichloromethane, washed with saturated sodium bicarbonate solution followed by brine solution. The organic layer was then dried over sodium sulfate, filtered and concentrated to yield the crude product. The desired amide M was then isolated via trituration with dichloromethane to give an off-white solid (57-95%).

Example 2: Synthesis of Compounds of the Invention

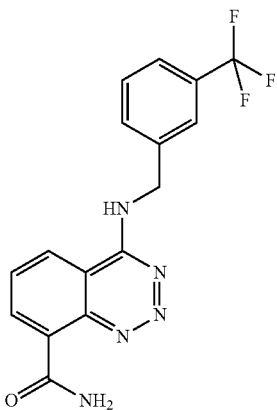 [SMILES: NC(=O)c1cccc2c(NCc3cccc(C(F)(F)F)c3)nnnc12]

4-(3-Trifluoromethyl-benzylamino)-benzo[d][1,2,3]triazine-8-carboxamide (1)

Compound 1 was prepared following general synthetic scheme 7 wherein 3-trifluoromethyl-benzylamine was reacted with 4-hydroxybenzo[d][1,2,3]triazine-8-carboxamide to give the title compound. LC-MS [348 (M+1)], $^1$HNMR (400 MHz, DMSO-d$_6$): δ 9.36-9.33 (m, 2H), 8.55-8.49 (m, 2H), 8.04 (s, 1H), 8.02-7.98 (m, 1H), 7.80 (s, 1H), 7.72 (d, 1H), 7.64 (d, 1H), 7.59-7.56 (m, 1H), 5.00 (d, 2H).

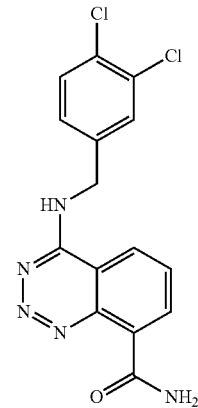 [SMILES: NC(=O)c1cccc2c(NCc3ccc(Cl)c(Cl)c3)nnnc12]

4-((3,4-dichlorobenzyl)amino)benzo[d][1,2,3]triazine-8-carboxamide (2)

Compound 2 was prepared following general synthetic scheme 7 wherein (3,4-dichlorophenyl)methanamine was reacted with 4-hydroxybenzo[d][1,2,3]-triazine-8-carboxamide to give the title compound. LC-MS [350 (M+1)], $^1$H NMR (400 MHz, DMSO-d6): δ 9.37 (s, 1H), 9.31 (t, 1H), 8.54 (d, 1H), 8.49 (d, 1H), 8.05 (s, 1H), 8.00 (t, 1H), 7.70 (s, 1H), 7.60 (d, 1H), 7.40 (d, 1H), 4.90 (d, 1H).

4-((pyridin-3-ylmethyl)amino)benzo[d][1,2,3]triazine-8-carboxamide (3)

Compound 3 was prepared following general synthetic scheme 7 wherein pyridin-3-ylmethanamine was reacted with 4-hydroxybenzo[d][1,2,3]-triazine-8-carboxamide to give the title compound. LC-MS [281 (M+1)], $^1$H NMR (400 MHz, DMSO-d): δ 9.38-9.32 (m, 2H), 8.66 (s, 1H), 8.54 (d, 1H), 8.50-8.48 (m, 2H), 8.05 (s, 1H), 7.99 (t, 1H), 7.82 (d, 1H), 7.38-7.35 (m, 1H), 4.93 (s, 2H).

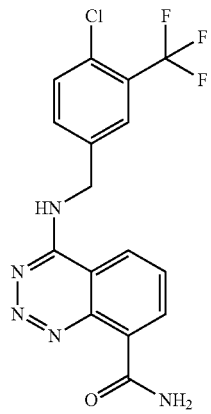 [SMILES: NC(=O)c1cccc2c(NCc3ccc(Cl)c(C(F)(F)F)c3)nnnc12]

4-((4-chloro-3-(trifluoromethyl)benzyl)amino)benzo[d][1,2,3]triazine-8-carboxamide (4)

Compound 4 was prepared following general synthetic scheme 7 wherein (4-chloro-3-(trifluoromethyl)phenyl)methanamine was reacted with 4-hydroxybenzo[d][1,2,3]-triazine-8-carboxamide to give the title compound. LC-MS [382 (M+1)], $^1$H NMR (400 MHz, DMSO-d): δ 9.38-9.32 (m, 2H), 8.54 (d, 1H), 8.48 (d, 1H), 8.05 (s, 1H), 8.02-7.98 (m, 1H), 7.95 (s, 1H), 7.73-7.68 (m, 2H), 4.96 (d, 2H).

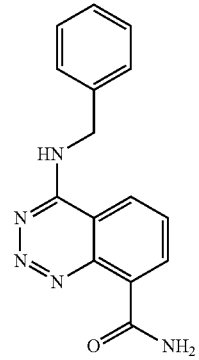

4-(benzylamino)benzo[d][1,2,3]triazine-8-carboxamide (6)

Compound 6 was prepared following general synthetic scheme 7 wherein benzylamine was reacted with 4-hydroxybenzo[d][1,2,3]-triazine-8-carboxamide to give the title compound. LC-MS [280 (M+1)], $^1$H NMR (400 MHz, DMSO-d): δ 9.42 (s, 1H), 9.31 (t, 1H), 8.53 (t, 1H), 8.04 (s, 1H), 7.98 (t, 1H), 7.41 (d, 2H), 7.34 (t, 2H), 7.28-7.24 (m, 1H), 4.92 (d, 2H).

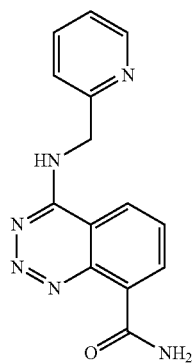 [SMILES: NC(=O)c1cccc2c(NCc3ccccn3)nnnc12]

4-((pyridin-2-ylmethyl)amino)benzo[d][1,2,3]triazine-8-carboxamide (5)

Compound 5 was prepared following general synthetic scheme 7 wherein pyridin-2-ylmethanamine was reacted with 4-hydroxybenzo[d][1,2,3]-triazine-8-carboxamide to give the title compound. LC-MS [281 (M+1)], $^1$H NMR (400 MHz, DMSO-d): δ 9.40 (s, 2H), 8.56-8.51 (m, 3H), 8.04 (s, 1H), 8.00 (t, 1H), 7.76-7.72 (m, 1H), 7.40 (d, 1H), 7.29-7.26 (m, 1H), 4.99 (d, 2H).

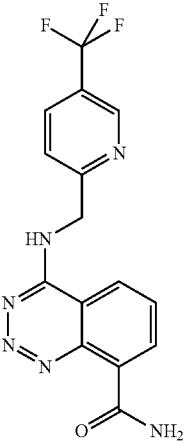 [SMILES: NC(=O)c1cccc2c(NCc3ccc(C(F)(F)F)cn3)nnnc12]

4-(((5-(trifluoromethyl)pyridin-2-yl)methyl)amino)benzo[d][1,2,3]triazine-8-carboxamide (7)

Compound 7 was prepared following general synthetic scheme 7 wherein (5-(trifluoromethyl)-pyridin-2-yl)methanamine was reacted with 4-hydroxybenzo[d][1,2,3]-triazine-8-carboxamide to give the title compound. LC-MS [349 (M+1)], $^1$H NMR (400 MHz, DMSO-d): δ 9.50 (t, 1H), 9.35 (s, 1H), 8.93 (s, 1H), 8.55 (d, 2H), 8.16 (dd, 1H), 8.05-8.01 (m, 2H), 7.65 (d, 1H), 5.07 (d, 2H).

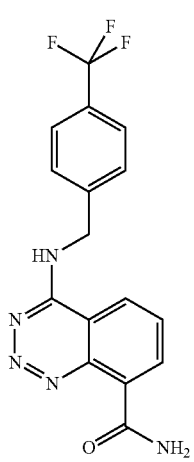 [SMILES: NC(=O)c1cccc2c(NCc3ccc(C(F)(F)F)cc3)nnnc12]

4-((4-(trifluoromethyl)benzyl)amino)benzo[d][1,2,3]triazine-8-carboxamide (8)

Compound 8 was prepared following general synthetic scheme 7 wherein (4-(trifluoromethyl)phenyl)methanamine was reacted with 4-hydroxybenzo[d][1,2,3]-triazine-8-carboxamide to give the title compound. LC-MS [348 (M+1)], $^1$H NMR (400 MHz, DMSO-d): δ 9.40-9.37 (m, 2H), 8.56-8.51 (m, 2H), 8.05 (s, 1H), 8.01 (t, 1H), 7.70 (d, 2H), 7.62 (d, 2H), 4.99 (d, 2H).

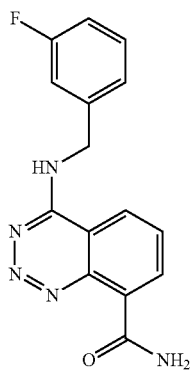 [SMILES: NC(=O)c1cccc2c(NCc3cccc(F)c3)nnnc12]

4-((3-fluorobenzyl)amino)benzo[d][1,2,3]triazine-8-carboxamide (9)

Compound 9 was prepared following general synthetic scheme 7 wherein (3-fluorophenyl)methanamine was reacted with 4-hydroxybenzo[d][1,2,3]-triazine-8-carboxamide to give the title compound. LC-MS [298 (M+1)], $^1$H NMR (400 MHz, DMSO-d6): 9.39 (s, 1H), 9.32 (s, 1H), 8.55-8.50 (m, 2H), 8.05 (s, 1H), 7.99 (t, 1H), 7.41-7.35 (m, 1H), 7.26-7.23 (m, 2H), 7.11-7.09 (m, 1H), 4.93 (d, 2H).

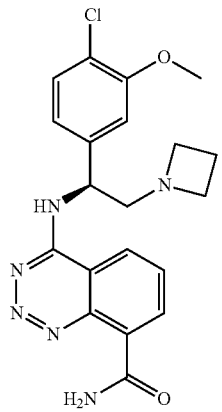 [SMILES: COc1cc([C@@H](CN2CCC2)Nc2nnnc3c(C(N)=O)cccc23)ccc1Cl]

(S)-4-((2-(azetidin-1-yl)-1-(4-chloro-3-methoxyphenyl)ethyl)amino)-benzo[d][1,2,3]triazine-8-carboxamide (10)

Compound 10 was prepared following general synthetic scheme 7 wherein (S)-2-(azetidin-1-yl)-1-(4-chloro-3-methoxyphenyl)ethanamine was reacted with 4-hydroxybenzo[d][1,2,3]-triazine-8-carboxamide to give the title compound. LC-MS [413 (M+1)], $^1$H NMR (400 MHz, DMSO-d6): δ 10.01 (s, 1H), 9.29 (s, 1H), 9.08 (d, 1H), 8.58 (d, 2H), 8.08 (t, 2H), 7.44 (d, 2H), 7.15 (dd, 1H), 6.05-6.00 (m, 1H), 4.44-4.41 (m, 1H), 4.26-4.22 (m, 1H), 4.21-4.05 (m, 2H), 3.89 (s, 3H), 3.80-3.74 (m, 3H), 2.49-2.40 (m, 2H).

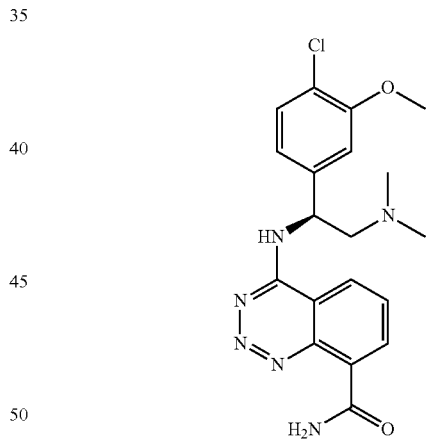

(S)-4-((1-(4-chloro-3-methoxyphenyl)-2-(dimethylamino)ethyl)amino)-benzo[d][1,2,3]triazine-8-carboxamide (11)

Compound 11 was prepared following general synthetic scheme 7 wherein (S)-1-(4-chloro-3-methoxyphenyl)-N2,N2-dimethylethane-1,2-diamine was reacted with 4-hydroxybenzo[d][1,2,3]-triazine-8-carboxamide to give the title compound. LC-MS [401 (M+1)], $^1$H NMR (400 MHz, DMSO-d6): δ 9.51 (s, 1H), 9.27 (s, 1H), 9.09 (d, 1H), 8.58 (dd, 2H), 8.08 (t, 2H), 7.44 (d, 2H), 7.18 (dd, 1H), 6.26 (t, 1H), 3.89 (s, 3H), 3.83-3.76 (m, 1H), 3.62-3.57 (m, 1H), 2.92 (d, 6H).

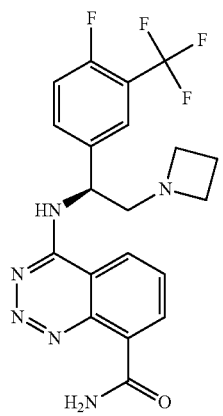 [SMILES: NC(=O)c1cccc2c(N[C@H](CN3CCC3)c3ccc(F)c(C(F)(F)F)c3)nnnc12]

(S)-4-((2-(azetidin-1-yl)-1-(4-fluoro-3-(trifluoromethyl)phenyl)ethyl)amino)benzo[d][1,2,3]triazine-8-carboxamide (12)

Compound 12 was prepared following general synthesis scheme 7 wherein 4-hydroxybenzo[d][1,2,3]-triazine-8-carboxamide was reacted with (S)-2-(azetidin-1-yl)-1-(4-fluoro-3-(trifluoromethyl)phenyl)ethanamine to give the title compound as a white solid. LC-MS [435 (M+1)].

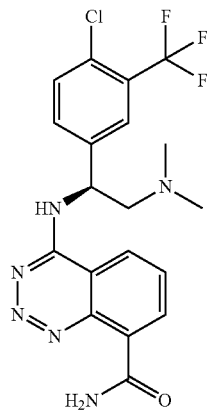 [SMILES: CN(C)C[C@@H](Nc1nnnc2c(C(N)=O)cccc12)c1ccc(Cl)c(C(F)(F)F)c1]

(S)-4-((1-(4-chloro-3-(trifluoromethyl)phenyl)-2-(dimethylamino)ethyl)amino)benzo-[d][1,2,3]triazine-8-carboxamide (13)

Compound 13 was prepared following general synthetic scheme 7 wherein (S)-1-(4-Chloro-3-(trifluoromethyl)phenyl)-N2,N2-dimethylethane-1,2-diamine was reacted with 4-hydroxybenzo[d][1,2,3]triazine-8-carboxamide to give the title compound. LC-MS [439 (M+1)], $^1$H NMR (400 MHz, DMSO-d6): δ 9.61 (brs, 1H), 9.23 (s, 1H), 9.17 (s, 1H), 8.58 (s, 2H), 8.19 (s, 1H), 8.08 (d, J=8.0 Hz, 2H), 7.92 (s, 1H), 7.78 (d, J=7.2 Hz, 1H), 6.34 (s, 1H), 3.83-3.63 (m, 2H), 2.91 (s, 6H).

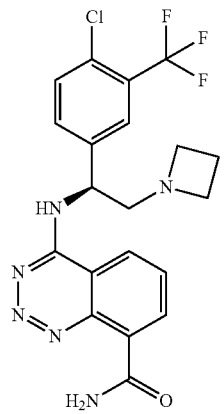 [SMILES: NC(=O)c1cccc2c(N[C@H](CN3CCC3)c3ccc(Cl)c(C(F)(F)F)c3)nnnc12]

(S)-4-((2-(azetidin-1-yl)-1-(4-chloro-3-(trifluoromethyl)phenyl)ethyl)amino)benzo[d][1,2,3]triazine-8-carboxamide (14)

Compound 14 was prepared following general synthetic scheme 7 wherein (S)-2-(Azetidin-1-yl)-1-(4-chloro-3-(trifluoromethyl)phenyl)ethan-1-amine was reacted with 4-hydroxybenzo[d][1,2,3]-triazine-8-carboxamide to give the title compound. LC-MS [451 (M+1)], $^1$H NMR (400 MHz, DMSO-d6): δ 9.30 (s, 1H), 8.87 (d, 1H), 8.63 (d, 1H), 8.54 (d, 1H), 8.05-8.01 (m, 3H), 7.81 (d, 1H), 7.70 (d, 1H), 5.59 (d, 1H), 3.21-3.14 (m, 4H), 3.02 (t, 1H), 2.99-2.78 (m, 1H), 1.92 (t, 2H).

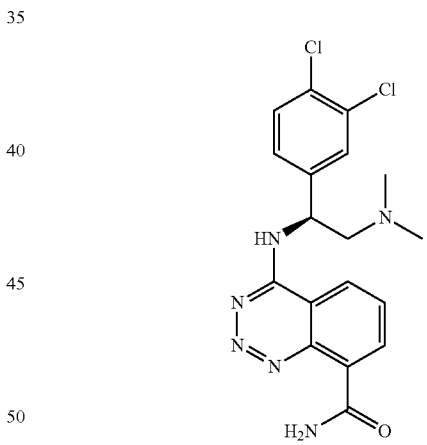

(S)-4-((1-(3,4-dichlorophenyl)-2-(dimethylamino)ethyl)amino)benzo[d][1,2,3]triazine-8-carboxamide (15)

Compound 15 was prepared following general synthetic scheme 7 wherein (S)-1-(3,4-dichlorophenyl)-N2,N2-dimethylethane-1,2-diamine was reacted with 4-hydroxybenzo[d][1,2,3]-triazine-8-carboxamide to give the title compound. LC-MS [407 (M+1)], $^1$H NMR (400 MHz, DMSO-d6): δ 9.63 (s, 1H), 9.24 (s, 1H), 9.12 (d, 1H), 8.59-8.56 (m, 2H), 8.10-8.06 (m, 2H), 7.95 (d, 1H), 7.69 (d, 1H), 7.60 (dd, 1H), 6.25 (t, 1H), 3.80 (t, 1H), 3.61-3.59 (m, 1H), 2.91 (d, 6H).

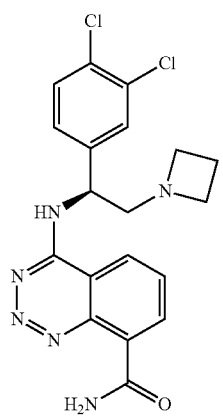 [SMILES: NC(=O)c1cccc2c(N[C@H](CN3CCC3)c3ccc(Cl)c(Cl)c3)nnnc12]

(S)-4-((2-(azetidin-1-yl)-1-(3,4-dichlorophenyl)ethyl)amino)benzo[d][1,2,3]triazine-8-carboxamide (16)

Compound 16 was prepared following general synthetic scheme 7 wherein (S)-2-(Azetidin-1-yl)-1-(3,4-dichlorophenyl)ethanamine was reacted with 4-hydroxybenzo[d][1,2,3]triazine-8-carboxamide to give the title compound. LC-MS [417 (M+1)].

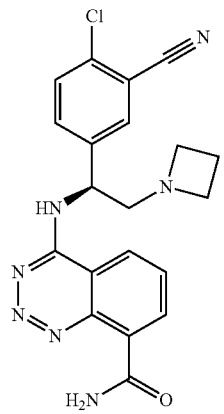

(S)-4-((2-(azetidin-1-yl)-1-(4-chloro-3-cyanophenyl)ethyl)amino)benzo[d][1,2,3]triazine-8-carboxamide (18)

Compound 18 was prepared following general synthetic scheme 7 wherein (S)-5-(1-amino-2-(azetidin-1-yl)ethyl)-2-chlorobenzonitrile was reacted with 4-hydroxybenzo[d][1,2,3]-triazine-8-carboxamide to give the title compound. LC-MS [408 (M+1)], $^1$H NMR (400 MHz, DMSO-d6): δ 9.31 (s, 1H), 8.82 (d, 1H), 8.63 (d, 1H), 8.55 (d, 1H), 8.12 (d, 1H), 8.03 (t, 2H), 7.85 (dd, 1H), 7.72 (d, 1H), 5.54 (d, 1H), 3.21-3.12 (m, 4H), 3.02-2.97 (m, 1H), 2.83-2.79 (m, 1H).

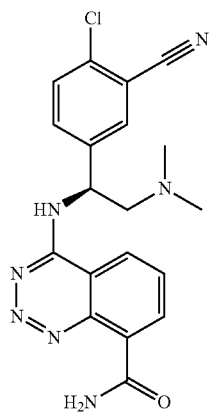 [SMILES: CN(C)C[C@@H](Nc1nnnc2c(C(N)=O)cccc12)c1ccc(Cl)c(C#N)c1]

(S)-4-((1-(4-chloro-3-cyanophenyl)-2-(dimethylamino)ethyl)amino)-benzo[d][1,2,3]triazine-8-carboxamide (17)

Compound 17 was prepared following general synthetic scheme 7 wherein (S)-5-(1-amino-2-(dimethylamino)ethyl)-2-chlorobenzonitrile was reacted with 4-hydroxybenzo[d][1,2,3]-triazine-8-carboxamide to give the title compound. LC-MS [397 (M+1)], $^1$H NMR (400 MHz, DMSO-d6): δ 9.31 (s, 1H), 8.81 (d, 1H), 8.63 (d, 1H), 8.55 (d, 1H), 8.15 (d, 1H), 8.05-8.01 (m, 2H), 7.88 (dd, 1H), 7.72 (d, 1H), 5.78 (q, 1H), 2.95-2.89 (m, 1H), 2.62-2.58 (m, 1H), 2.24 (s, 6H).

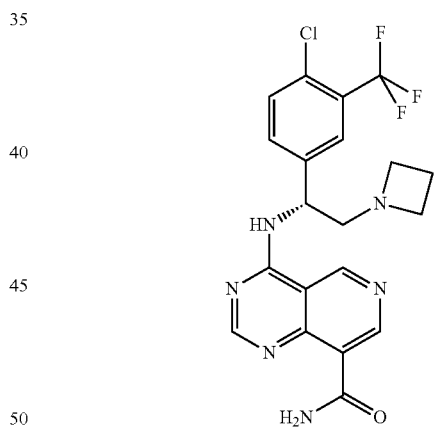

(R)-4-((2-(azetidin-1-yl)-1-(4-chloro-3-(trifluoromethyl)phenyl)ethyl)amino)pyrido[4,3-d]pyrimidine-8-carboxamide (19)

Compound 19 was prepared following general synthetic scheme 7 wherein (R)-2-(azetidin-1-yl)-1-(4-chloro-3-(trifluoromethyl)phenyl)ethanamine was reacted with 4-hydroxypyrido[4,3-d]pyrimidine-8-carboxamide to give the title compound as an off-white solid. LC-MS [451 (M+1)], $^1$H NMR (400 MHz, Chloroform-d) δ 10.43 (s, 1H), 9.75 (s, 1H), 9.59 (s, 1H), 8.62 (s, 1H), 7.98 (s, 1H), 7.69 (s, 1H), 7.48 (d, 2H), 6.12 (s, 1H), 5.18 (d, 1H), 3.25 (dq, 4H), 3.05-2.89 (m, 2H), 2.14 (p, 2H).

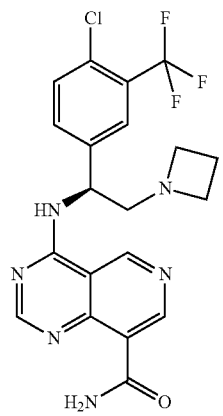 [SMILES: NC(=O)c1cncc2c(N[C@H](CN3CCC3)c3ccc(Cl)c(C(F)(F)F)c3)ncnc12]

(S)-4-((2-(azetidin-1-yl)-1-(4-chloro-3-(trifluoromethyl)phenyl)ethyl)amino)pyrido[4,3-d]pyrimidine-8-carboxamide (20)

Compound 20 was prepared following general synthetic scheme 7 wherein (S)-2-(azetidin-1-yl)-1-(4-chloro-3-(trifluoromethyl)phenyl)ethanamine was reacted with 4-hydroxypyrido[4,3-d]pyrimidine-8-carboxamide to give the title compound. LC-MS [451 (M+1)], ¹H NMR (400 MHz, Chloroform-d) δ 10.43 (s, 1H), 9.75 (s, 1H), 9.59 (s, 1H), 8.62 (s, 1H), 7.98 (s, 1H), 7.69 (s, 1H), 7.48 (d, 2H), 6.12 (s, 1H), 5.18 (d, 1H), 3.25 (dq, 4H), 3.05-2.89 (m, 2H), 2.14 (p, 2H).

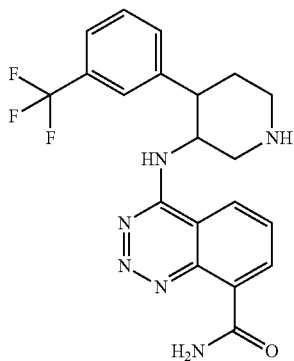 [SMILES: NC(=O)c1cccc2c(NC3CNCCC3c3cccc(C(F)(F)F)c3)nnnc12]

4-((4-(3-(trifluoromethyl)phenyl)piperidin-3-yl)amino)benzo[d][1,2,3]triazine-8-carboxamide (21)

Compound 21 was prepared following general synthesis scheme 9 wherein 4-hydroxybenzo[d][1,2,3]triazine-8-carboxylic acid amide was reacted with tert-butyl 3-amino-4-(3-(trifluoromethyl)phenyl)piperidine-1-carboxylate to give the title compound. LC-MS [417 (M+H)], ¹H NMR (400 MHz, DMSO-d6) δ 9.24 (s, 1H), 8.98 (d, 1H), 8.84 (t, 1H), 8.54 (d, 1H), 8.50 (d, 1H), 8.30 (d, 1H), 8.04-7.89 (m, 2H), 7.67 (s, 1H), 7.59 (t, 1H), 7.45 (d, 2H), 5.42-5.26 (m, 1H), 3.64 (d, 1H), 3.49 (d, 1H), 3.35 (td, 1H), 3.23-2.90 (m, 2H), 2.52-2.00 (m, 2H).

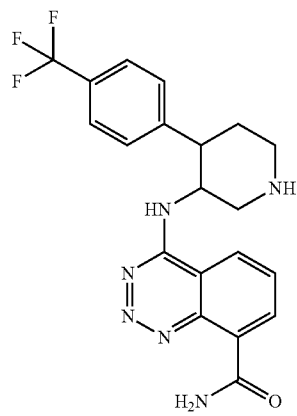 [SMILES: NC(=O)c1cccc2c(NC3CNCCC3c3ccc(C(F)(F)F)cc3)nnnc12]

4-((4-(4-(trifluoromethyl)phenyl)piperidin-3-yl)amino)benzo[d][1,2,3]triazine-8-carboxamide (22)

Compound 22 was prepared following general synthesis scheme 9 wherein 4-hydroxybenzo[d][1,2,3]triazine-8-carboxylic acid amide was reacted with tert-butyl 3-amino-4-(4-(trifluoromethyl)phenyl)piperidine-1-carboxylate to give the title compound. LC-MS [417 (M+H)], ¹H NMR (400 MHz, DMSO-d6) δ 9.21 (s, 1H), 9.04-8.92 (m, 1H), 8.61-8.43 (m, 3H), 8.11-7.92 (m, 2H), 7.72 (d, 1H), 7.64-7.46 (m, 5H), 5.58-5.44 (m, 1H), 3.71-3.44 (m, 4H), 3.30-3.09 (m, 1H), 2.81-2.60 (m, 1H), 2.08 (d, 1H).

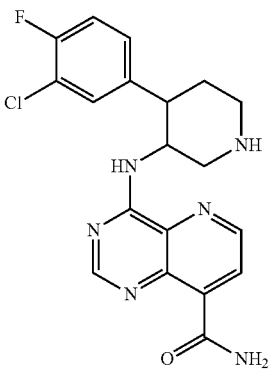 [SMILES: NC(=O)c1ccnc2c(NC3CNCCC3c3ccc(F)c(Cl)c3)ncnc12]

4-[4-(3-Chloro-4-fluoro-phenyl)-piperidin-3-ylamino]-pyrido[3,2-d]pyrimidine-8-carboxamide (23)

Compound 23 was prepared following general synthesis scheme 9 wherein 4-hydroxy-pyrido[3,2-d]pyrimidine-8-carboxylic acid amide was reacted with tert-butyl 3-amino-4-(3-chloro-4-fluoro-phenyl)piperidine-1-carboxylate to give the title compound. LC-MS [401 (M+H)].

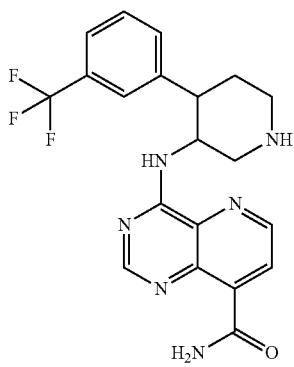 [SMILES: NC(=O)c1ccnc2c(NC3CNCCC3c3cccc(C(F)(F)F)c3)ncnc12]

4-((4-(3-(trifluoromethyl)phenyl)piperidin-3-yl)amino)pyrido[3,2-d]pyrimidine-8-carboxamide (24)

Compound 24 was prepared following general synthesis scheme 9 wherein 4-hydroxy-pyrido[3,2-d]pyrimidine-8-carboxylic acid amide was reacted with tert-butyl 3-amino-4-(3-(trifluoromethyl)phenyl)piperidine-1-carboxylate to give the title compound. LC-MS [417 (M+H)], $^1$H NMR (400 MHz, DMSO-d6) δ 9.78 (d, 1H), 9.06 (d, 1H), 9.03-8.95 (m, 1H), 8.90 (d, 1H), 8.88-8.73 (m, 1H), 8.50 (s, 1H), 8.32 (d, 1H), 8.16 (d, 1H), 7.62 (s, 1H), 7.56 (q, 1H), 7.43 (d, 2H), 5.22-5.02 (m, 1H), 3.60-3.38 (m, 3H), 3.14 (q, 1H), 2.99 (q, 1H), 2.54 (d, 1H), 2.08 (dt, 2H).

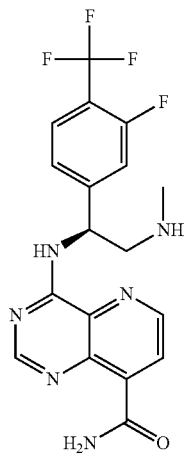

4-[(S)-1-(3-Fluoro-4-trifluoromethyl-phenyl)-2-methylamino-ethylamino]-pyrido[3,2-d]pyrimidine-8-carboxylic Acid Amide (26)

Compound 26 was prepared following general synthesis scheme 8 wherein 4-hydroxypyrido[3,2-d]pyrimidine-8-carboxamide (G) was reacted with N—[(S)-2-Amino-2-(3-fluoro-4-trifluoromethyl-phenyl)-ethyl]-N-methyl-4-nitro-benzenesulfonamide hydrochloride to give the title compound as a white solid. LC/MS [409 (M+H)]; $^1$H NMR (400 MHz, DMSO-d6) δ 9.92 (s, 1H), 9.20 (s, 1H), 9.01 (dd, J=4.7, 1.7 Hz, 1H), 8.54 (d, J=1.7 Hz, 1H), 8.45-8.34 (m, 1H), 8.25-8.10 (m, 1H), 7.72 (t, J=7.8 Hz, 1H), 7.61 (d, J=12.1 Hz, 1H), 7.49 (d, J=8.1 Hz, 1H), 5.53 (t, J=6.5 Hz, 1H), 3.21-3.08 (m, 1H), 3.05-2.88 (m, 1H), 2.30 (s, 3H), 2.01 (s, 1H).

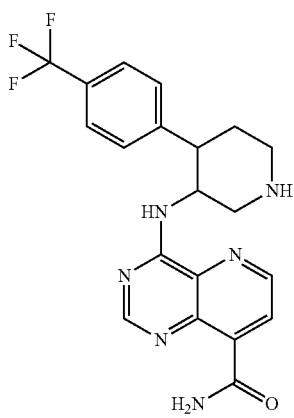 [SMILES: NC(=O)c1ccnc2c(NC3CNCCC3c3ccc(C(F)(F)F)cc3)ncnc12]

4-((4-(4-(trifluoromethyl)phenyl)piperidin-3-yl)amino)pyrido[3,2-d]pyrimidine-8-carboxamide (25)

Compound 25 was prepared following general synthesis scheme 9 wherein 4-hydroxy-pyrido[3,2-d]pyrimidine-8-carboxylic acid amide was reacted with tert-butyl 3-amino-4-(4-(trifluoromethyl)phenyl)piperidine-1-carboxylate to give the title compound. LC-MS [417 (M+H)], $^1$H NMR (400 MHz, DMSO-d6) δ 9.77 (d, 1H), 8.99 (d, 1H), 8.93-8.82 (m, 1H), 8.82-8.70 (m, 1H), 8.65 (d, 1H), 8.36 (d, 2H), 8.16 (d, 1H), 7.48 (t, 4H), 5.37-5.21 (m, 1H), 3.75-3.42 (m, 1H), 3.26-3.06 (m, 1H), 2.02 (d, 1H).

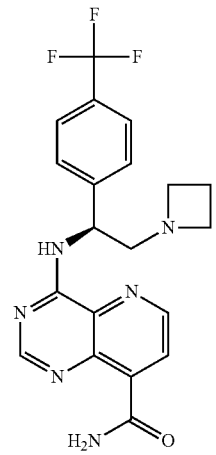 [SMILES: NC(=O)c1ccnc2c(N[C@H](CN3CCC3)c3ccc(C(F)(F)F)cc3)ncnc12]

4-[(S)-2-Azetidin-1-yl-1-(4-trifluoromethyl-phenyl)-ethylamino]-pyrido[3,2-d]pyrimidine-8-carboxylic Acid Amide (27)

Compound 27 was prepared following general synthesis scheme 7 wherein 4-hydroxypyrido[3,2-d]pyrimidine-8-carboxamide (G) was reacted with (S)-2-Azetidin-1-yl-1-(4-trifluoromethyl-phenyl)-ethylamine dihydrochloride to give the title compound as a white solid. LC/MS [417 (M+H)];

¹H NMR (400 MHz, DMSO-d6) δ 9.92 (d, J=3.4 Hz, 1H), 9.11 (d, J=7.9 Hz, 1H), 9.01 (dd, J=4.5, 1.0 Hz, 1H), 8.53 (s, 1H), 8.38 (dd, J=4.5, 1.0 Hz, 1H), 8.16 (d, J=3.4 Hz, 1H), 7.83-7.50 (m, 3H), 5.36 (q, J=7.2 Hz, 1H), 3.21-2.99 (m, 4H), 2.84 (dd, J=12.0, 5.6 Hz, 1H), 1.92 (p, J=6.9 Hz, 2H).

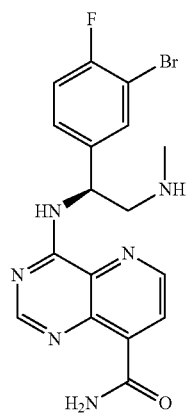 [SMILES: CNC[C@@H](Nc1ncnc2c(C(N)=O)ccnc12)c1ccc(F)c(Br)c1]

4-[(S)-1-(3-Bromo-4-fluoro-phenyl)-2-methylamino-ethylamino]-pyrido[3,2-d]pyrimidine-8-carboxylic Acid Amide (28)

Compound 28 was prepared following general synthesis scheme 8 wherein 4-hydroxypyrido[3,2-d]pyrimidine-8-carboxamide (G) was reacted with N—[(S)-2-Amino-2-(3-bromo-4-fluoro-phenyl)-ethyl]-N-methyl-4-nitro-benzenesulfonamide hydrochloride to give the title compound as a beige solid. LC/MS [419 (M+H)]; ¹H NMR (400 MHz, DMSO-d6) δ 9.90 (s, 1H), 9.40 (d, 1H), 9.02 (dd, 1.9 Hz, 1H), 8.60 (d, 1H), 8.40 (dd, 1H), 8.19 (s, 1H), 8.04-7.76 (m, 1H), 7.55 (ddd, 4.7, 2.1 Hz, 1H), 7.36 (td, 1H), 5.88-5.57 (m, 1H), 3.48 (t, 1H), 3.21 (dd, 1H), 2.54 (d, 1H), 2.50 (s, 3H).

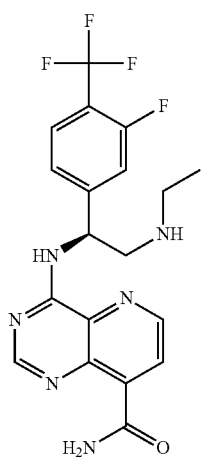 [SMILES: CCNC[C@@H](Nc1ncnc2c(C(N)=O)ccnc12)c1ccc(C(F)(F)F)c(F)c1]

4-[(S)-2-Ethylamino-1-(3-fluoro-4-trifluoromethyl-phenyl)-ethylamino]-pyrido[3,2-d]pyrimidine-8-carboxylic Acid Amide (29)

Compound 29 was prepared following general synthesis scheme 8 wherein 4-hydroxypyrido[3,2-d]pyrimidine-8-carboxamide (G) was reacted with N—[(S)-2-Amino-2-(3-fluoro-4-trifluoromethyl-phenyl)-ethyl]-N-ethyl-4-nitro-benzenesulfonamide hydrochloride to give the title compound as a pale yellow solid. LC/MS [423 (M+H)]; ¹H NMR (400 MHz, DMSO-d6) δ 9.93 (d, J=3.7 Hz, 1H), 9.25 (d, J=7.8 Hz, 1H), 9.01 (d, J=4.5 Hz, 1H), 8.54 (s, 1H), 8.39 (d, J=4.5 Hz, 1H), 8.19 (d, J=3.8 Hz, 1H), 7.73 (t, J=7.9 Hz, 1H), 7.62 (d, J=12.0 Hz, 1H), 7.49 (d, J=8.1 Hz, 1H), 5.51 (q, J=4.9 Hz, 1H), 3.20 (dd, J=12.5, 8.1 Hz, 1H), 3.03 (dd, J=12.4, 5.2 Hz, 1H), 2.70-2.53 (m, 2H), 0.99 (t, J=7.1 Hz, 3H).

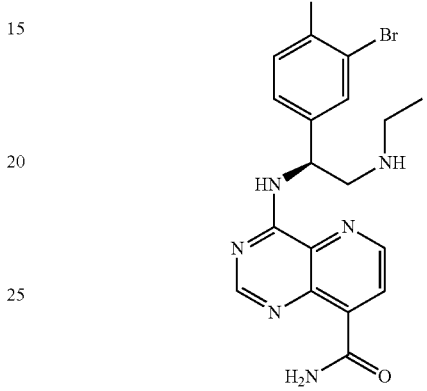

4-[(S)-1-(3-Bromo-4-fluoro-phenyl)-2-ethylamino-ethylamino]-pyrido[3,2-d]pyrimidine-8-carboxylic Acid Amide (30)

Compound 30 was prepared following general synthesis scheme 8 wherein 4-hydroxypyrido[3,2-d]pyrimidine-8-carboxamide (G) was reacted with N—[(S)-2-Amino-2-(3-bromo-4-fluoro-phenyl)-ethyl]-N-ethyl-4-nitro-benzenesulfonamide hydrochloride to give the title compound as a white solid. LC/MS [434 (M+H)]; ¹H NMR (400 MHz, DMSO-d6) δ 9.90 (s, 1H), 9.36 (s, 1H), 9.02 (d, J=4.5 Hz, 1H), 8.60 (s, 1H), 8.40 (d, J=4.4 Hz, 1H), 8.18 (s, 1H), 7.87 (d, J=4.9 Hz, 1H), 7.53 (d, J=5.5 Hz, 1H), 7.35 (t, J=8.7 Hz, 1H), 5.78-5.51 (m, 1H), 3.55-3.36 (m, 1H), 3.23-3.10 (m, 1H), 2.93-2.69 (m, 2H), 1.08 (t, J=7.0 Hz, 3H).

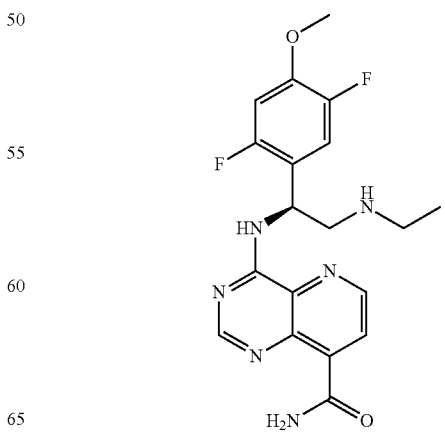

4-[(S)-1-(2,5-Difluoro-4-methoxy-phenyl)-2-ethyl-amino-ethylamino]-pyrido[3,2-d]pyrimidine-8-carboxylic Acid Amide (31)

Compound 31 was prepared following general synthesis scheme 8 wherein 4-hydroxypyrido[3,2-d]pyrimidine-8-carboxamide (G) was reacted with N—[(S)-2-Amino-2-(2,5-difluoro-4-methoxy-phenyl)-ethyl]-N-ethyl-4-nitro-benzenesulfonamide hydrochloride to give the title compound as a pale yellow solid. LC/MS [403 (M+H)]; $^1$H NMR (400 MHz, DMSO-d6) δ 9.94 (s, 1H), 9.03 (d, J=26.0 Hz, 1H), 8.98 (s, 1H), 8.56 (s, 1H), 8.37 (d, J=4.5 Hz, 1H), 8.16 (s, 1H), 7.40 (dd, J=12.1, 7.0 Hz, 1H), 7.09 (dd, J=11.5, 7.3 Hz, 1H), 5.69 (s, 1H), 3.82 (s, 3H), 3.13 (dd, J=12.3, 8.5 Hz, 1H), 2.91 (dd, J=12.4, 5.2 Hz, 1H), 2.63-2.53 (m, 2H), 1.85 (s, 1H), 0.97 (t, J=7.1 Hz, 3H).

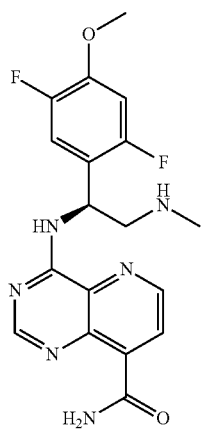 [SMILES: CNC[C@@H](Nc1ncnc2c(C(N)=O)ccnc12)c1cc(F)c(OC)cc1F]

4-[(S)-1-(2,5-Difluoro-4-methoxy-phenyl)-2-methyl-amino-ethylamino]-pyrido[3,2-d]pyrimidine-8-carboxylic Acid Amide (32)

Compound 32 was prepared following general synthesis scheme 8 wherein 4-hydroxypyrido[3,2-d]pyrimidine-8-carboxamide (G) was reacted with N—[(S)-2-Amino-2-(2,5-difluoro-4-methoxy-phenyl)-ethyl]-N-methyl-4-nitro-benzenesulfonamide hydrochloride to give the title compound as a white solid. LC/MS [389 (M+H)]; $^1$H NMR (400 MHz, DMSO-d6) δ 10.03-9.86 (m, 1H), 9.04 (s, 1H), 8.98 (d, J=4.5 Hz, 1H), 8.56 (s, 1H), 8.37 (d, J=4.5 Hz, 1H), 8.24-8.07 (m, 1H), 7.42 (dd, J=12.1, 7.0 Hz, 1H), 7.09 (dd, J=11.5, 7.2 Hz, 1H), 5.72 (s, 1H), 3.82 (s, 3H), 3.11 (dd, J=12.3, 8.5 Hz, 1H), 2.85 (dd, J=12.4, 5.3 Hz, 1H), 2.54 (s, 1H), 2.30 (s, 3H).

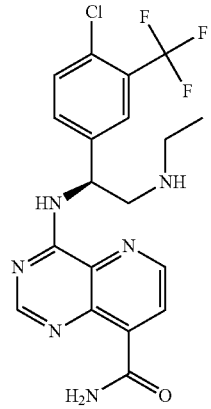 [SMILES: CCNC[C@@H](Nc1ncnc2c(C(N)=O)ccnc12)c1ccc(Cl)c(C(F)(F)F)c1]

4-[(S)-1-(4-Chloro-3-trifluoromethyl-phenyl)-2-ethylamino-ethylamino]-pyrido[3,2-d]pyrimidine-8-carboxylic Acid Amide (33)

Compound 33 was prepared following general synthesis scheme 8 wherein 4-hydroxypyrido[3,2-d]pyrimidine-8-carboxamide (G) was reacted with N—[(S)-2-Amino-2-(4-chloro-3-trifluoromethyl-phenyl)-ethyl]-N-ethyl-4-nitro-benzenesulfonamide hydrochloride to give the title compound as a beige solid. LC/MS [439 (M+H)]; $^1$H NMR (400 MHz, DMSO-d6) δ 9.92 (s, 1H), 9.27 (s, 1H), 9.00 (d, J=4.5 Hz, 1H), 8.54 (s, 1H), 8.38 (d, J=4.5 Hz, 1H), 8.16 (s, 1H), 8.00 (d, J=1.8 Hz, 1H), 7.76 (dd, J=8.3, 1.9 Hz, 1H), 7.66 (d, J=8.3 Hz, 1H), 5.51 (s, 1H), 3.17 (dd, J=12.4, 8.0 Hz, 1H), 3.00 (dd, J=12.4, 5.6 Hz, 1H), 2.60-2.55 (m, 2H), 2.54 (s, 1H), 0.97 (t, J=7.1 Hz, 3H).

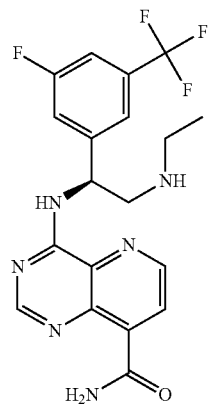 [SMILES: CCNC[C@@H](Nc1ncnc2c(C(N)=O)ccnc12)c1cc(F)cc(C(F)(F)F)c1]

4-[(S)-2-Ethylamino-1-(3-fluoro-5-trifluoromethyl-phenyl)-ethylamino]-pyrido[3,2-d]pyrimidine-8-carboxylic Acid Amide (34)

Compound 34 was prepared following general synthesis scheme 8 wherein 4-hydroxypyrido[3,2-d]pyrimidine-8-carboxamide (G) was reacted with N—[(S)-2-Amino-2-(3-fluoro-5-trifluoromethyl-phenyl)-ethyl]-N-ethyl-4-nitro-benzenesulfonamide hydrochloride to give the title compound as a pale yellow solid. LC/MS [423 (M+H)]; $^1$H NMR (400 MHz, DMSO-d6) δ 9.92 (s, 1H), 9.24 (s, 1H), 9.01 (d, J=4.5 Hz, 1H), 8.55 (s, 1H), 8.38 (d, J=4.4 Hz, 1H), 8.16 (s, 1H), 7.74 (s, 1H), 7.66 (d, J=9.8 Hz, 1H), 7.53 (d, J=8.9 Hz, 1H), 5.73-5.28 (m, 1H), 3.28 (s, 1H), 3.23-3.10 (m, 1H), 3.06-2.93 (m, 1H), 2.56 (d, J=7.1 Hz, 2H), 0.97 (t, J=7.2 Hz, 3H).

NMR (500 MHz, DMSO-d6) δ 9.94 (s, 1H), 9.27-8.84 (m, 2H), 8.53 (s, 1H), 8.37 (d, J=4.4 Hz, 1H), 8.17 (s, 1H), 7.49 (d, J=8.4 Hz, 2H), 7.36 (d, J=8.4 Hz, 2H), 5.37-4.98 (m, 2H), 3.16-2.94 (m, 3H), 2.78 (dd, J=11.9, 5.3 Hz, 1H), 2.07-1.65 (m, 2H).

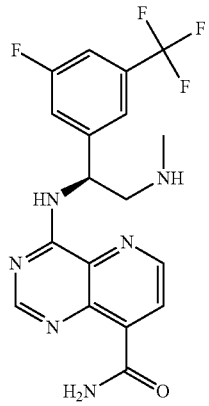

4-[(S)-1-(3-Fluoro-5-trifluoromethyl-phenyl)-2-methylamino-ethylamino]-pyrido[3,2-d]pyrimidine-8-carboxylic Acid Amide (35)

Compound 35 was prepared following general synthesis scheme 8 wherein 4-hydroxypyrido[3,2-d]pyrimidine-8-carboxamide (G) was reacted with N—[(S)-2-Amino-2-(3-fluoro-5-trifluoromethyl-phenyl)-ethyl]-N-methyl-4-nitro-benzenesulfonamide hydrochloride to give the title compound as a white solid. LC/MS [409 (M+H)]; $^1$H NMR (400 MHz, DMSO-d6) δ 9.92 (s, 1H), 9.25 (s, 1H), 9.01 (d, J=4.5 Hz, 1H), 8.55 (s, 1H), 8.38 (d, J=4.5 Hz, 1H), 8.16 (s, 1H), 7.74 (s, 1H), 7.67 (d, J=9.3 Hz, 1H), 7.53 (d, J=8.7 Hz, 1H), 5.57 (s, 1H), 3.15 (dd, J=12.3, 8.3 Hz, 1H), 2.95 (dd, J=12.3, 5.5 Hz, 1H), 2.30 (s, 3H).

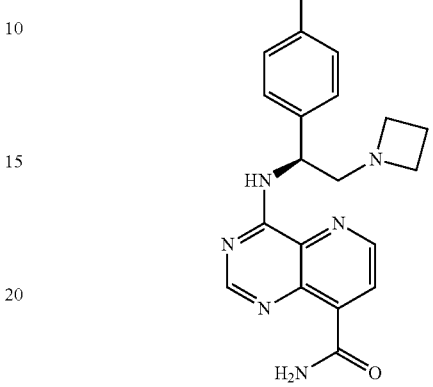

4-[(S)-2-Azetidin-1-yl-1-(4-isopropyl-phenyl)-ethyl-amino]-pyrido[3,2-d]pyrimidine-8-carboxylic Acid Amide (37)

Compound 37 was prepared following general synthesis scheme 7 wherein 4-hydroxypyrido[3,2-d]pyrimidine-8-carboxamide (G) was reacted with (S)-2-Azetidin-1-yl-1-(4-isopropyl-phenyl)-ethylamine dihydrochloride to give the title compound as an off-white solid. LC/MS [391 (M+H)]; 1H NMR (500 MHz, DMSO-d6) δ 9.97 (s, 1H), 9.38-8.87 (m, 2H), 8.53 (s, 1H), 8.37 (d, J=4.4 Hz, 1H), 8.17 (s, 1H), 7.37 (d, J=8.0 Hz, 2H), 7.17 (d, J=8.0 Hz, 2H), 5.60-4.97 (m, 1H), 3.16-2.99 (m, 5H), 2.89-2.77 (m, 1H), 2.74 (dd, J=11.9, 4.9 Hz, 1H), 2.02-1.72 (m, 2H), 1.16 (d, J=6.8 Hz, 6H).

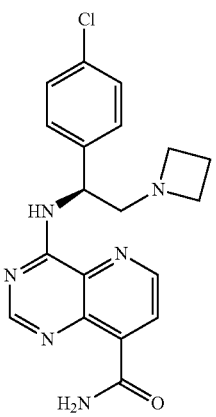 [SMILES: NC(=O)c1ccnc2c(N[C@H](CN3CCC3)c3ccc(Cl)cc3)ncnc12]

4-[(S)-2-Azetidin-1-yl-1-(4-chloro-phenyl)-ethyl-amino]-pyrido[3,2-d]pyrimidine-8-carboxylic Acid Amide (36)

Compound 36 was prepared following general synthesis scheme 7 wherein 4-hydroxypyrido[3,2-d]pyrimidine-8-carboxamide (G) was reacted with (S)-2-Azetidin-1-yl-1-(4-chloro-phenyl)-ethylamine dihydrochloride to give the title compound as an off-white solid. LC/MS [383 (M+H)]; $^1$H

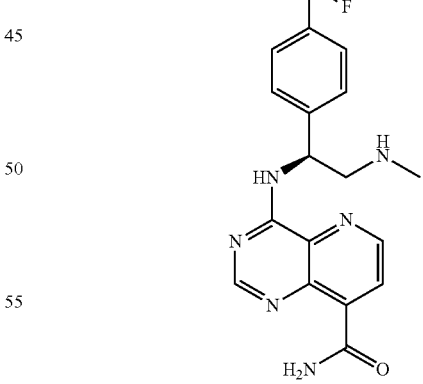

4-[(S)-2-Methylamino-1-(4-trifluoromethyl-phenyl)-ethylamino]-pyrido[3,2-d]pyrimidine-8-carboxylic Acid Amide (38)

Compound 38 was prepared following general synthesis scheme 8 wherein 4-hydroxypyrido[3,2-d]pyrimidine-8-carboxamide (G) was reacted with N—[(S)-2-Amino-2-(4- trifluoromethyl-phenyl)-ethyl]-N-methyl-4-nitro-benzene-sulfonamide hydrochloride to give the title compound as a white solid. LC/MS [391 (M+H)]; $^1$H NMR (500 MHz, DMSO-d6) δ 9.93 (s, 1H), 9.21 (s, 1H), 9.00 (d, J=4.4 Hz, 1H), 8.52 (s, 1H), 8.38 (d, J=4.4 Hz, 1H), 8.17 (s, 1H), 7.68 (s, 4H), 5.53 (s, 1H), 3.20-3.07 (m, 1H), 2.94 (dd, J=12.2, 4.9 Hz, 1H), 2.30 (s, 3H).

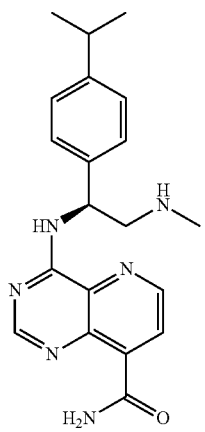 [SMILES: CNC[C@@H](Nc1ncnc2c(C(N)=O)ccnc12)c1ccc(C(C)C)cc1]

4-[(S)-1-(4-Isopropyl-phenyl)-2-methylamino-ethyl-amino]-pyrido[3,2-d]pyrimidine-8-carboxylic Acid Amide (39)

Compound 39 was prepared following general synthesis scheme 8 wherein a mixture of 4-Hydroxy-pyrido[3,2-d]pyrimidine-8-carboxylamide (G) and 4-Hydroxy-pyrido[3,4-d]pyrimidine-8-carboxylamide (H) was reacted with N—[(S)-2-Amino-2-(4-isopropyl-phenyl)-ethyl]-N-methyl-4-nitro-benzenesulfonamide hydrochloride. The title compound was isolated as the major product (white solid). LC/MS [365 (M+H)]; $^1$H NMR (500 MHz, DMSO-d6) δ 9.92 (s, 1H), 9.47 (d, J=8.6 Hz, 1H), 9.03 (d, J=4.3 Hz, 1H), 8.63 (s, 1H), 8.41 (d, J=4.3 Hz, 1H), 8.22 (s, 1H), 7.43 (d, J=8.1 Hz, 2H), 7.25 (d, J=8.1 Hz, 2H), 5.92-5.76 (m, 1H), 3.89-3.65 (m, 1H), 3.39 (d, J=12.6 Hz, 1H), 2.94-2.81 (m, 1H), 2.61 (s, 3H), 1.16 (d, J=6.8 Hz, 6H).

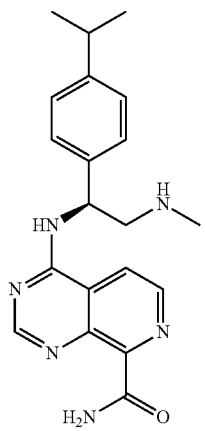 [SMILES: CNC[C@@H](Nc1ncnc2c(C(N)=O)nccc12)c1ccc(C(C)C)cc1]

4-[(S)-1-(4-Isopropyl-phenyl)-2-methylamino-ethyl-amino]-pyrido[3,4-d]pyrimidine-8-carboxylic Acid Amide (40)

Compound 40 was prepared following general synthesis scheme 8 wherein a mixture of 4-Hydroxy-pyrido[3,2-d]pyrimidine-8-carboxylamide (G) and 4-Hydroxy-pyrido[3,4-d]pyrimidine-8-carboxylamide (H) was reacted with N—[(S)-2-Amino-2-(4-isopropyl-phenyl)-ethyl]-N-methyl-4-nitro-benzenesulfonamide hydrochloride. The title compound was isolated as the minor product (white solid). LC/MS [365 (M+H)]; $^1$H NMR (500 MHz, DMSO-d6) δ 9.14 (s, 2H), 8.82-8.58 (m, 2H), 8.40 (s, 1H), 7.82 (s, 1H), 7.42 (d, J=7.8 Hz, 2H), 7.26 (d, J=7.9 Hz, 2H), 6.52 (s, 1H), 5.89 (s, 1H), 3.68-3.54 (m, 1H), 3.51-3.43 (m, 1H), 2.98-2.78 (m, 1H), 2.65 (s, 3H), 1.17 (d, J=6.8 Hz, 6H).

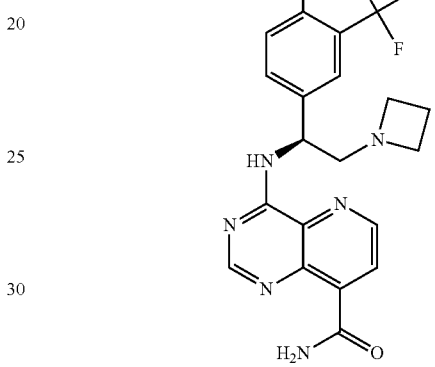

4-[(S)-2-Azetidin-1-yl-1-(4-chloro-3-trifluoromethyl-phenyl)-ethylamino]-pyrido[3,2-d]pyrimidine-8-carboxamide (41)

Compound 41 was prepared following general synthesis scheme 8 wherein 4-hydroxy-pyrido[3,2-d]pyrimidine-8-carboxylamide (G) was reacted with (S)-2-(azetidin-1-yl)-1-(4-chloro-3-(trifluoromethyl)phenyl)ethanamine dihydrochloride to give the title compound as a off-white solid. LC/MS [451 (M+H)]; $^1$H NMR (400 MHz, DMSO-d6) δ 9.93 (s, 1H), 9.20 (s, 1H), 9.01 (d, 1H), 8.56 (d, 1H), 8.39 (dd, 1H), 8.20 (d, 1H), 8.05 (s, 1H), 7.80 (d, 1H), 7.68 (d, 1H), 5.38 (t, 1H), 3.11 (ddd, 5H), 2.84 (dd, 1H), 1.93 (p, 2H). IC$_{50}$ p70S6K: 1.6 nM, Akt: 11 nM

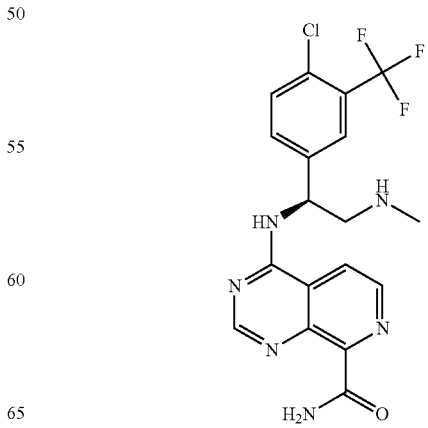

4-[(S)-1-(4-Chloro-3-trifluoromethyl-phenyl)-2-methylamino-ethylamino]-pyrido[3,4-d]pyrimidine-8-carboxylic Acid Amide (42)

Compound 42 was prepared following general synthesis scheme 8 wherein a mixture of 4-Hydroxy-pyrido[3,2-d]pyrimidine-8-carboxylamide (G) and 4-Hydroxy-pyrido[3,4-d]pyrimidine-8-carboxylamide (H) was reacted with N—[(S)-2-Amino-2-(4-chloro-3-trifluoromethyl-phenyl)-ethyl]-N-methyl-4-nitro-benzenesulfonamide hydrochloride. LC/MS [425 (M+H)]; $^1$H NMR (500 MHz, DMSO-d6) δ 9.92 (s, 1H), 9.28 (s, 1H), 9.00 (d, J=4.5 Hz, 1H), 8.55 (s, 1H), 8.38 (d, J=4.5 Hz, 1H), 8.17 (s, 1H), 8.00 (s, 1H), 7.77 (d, J=7.4 Hz, 1H), 7.67 (d, J=8.4 Hz, 1H), 5.64-5.44 (m, 1H), 3.20-3.09 (m, 1H), 3.04-2.88 (m, 1H), 2.30 (s, 3H).

4-[(S)-1-(4-Chloro-3-methyl-phenyl)-2-methyl-amino-ethylamino]-pyrido[3,2-d]pyrimidine-8-carboxylic Acid Amide (44)

Compound 44 was prepared following general synthesis scheme 8 wherein 4-hydroxypyrido[3,2-d]pyrimidine-8-carboxamide (G) was reacted with N—[(S)-2-Amino-2-(4-chloro-3-methyl-phenyl)-ethyl]-N-methyl-4-nitro-benzenesulfonamide hydrochloride to give the title compound as a white solid. LC/MS [371 (M+H)]; $^1$H NMR (500 MHz, DMSO-d6) δ 9.95 (s, 1H), 9.08 (s, 1H), 8.99 (d, J=4.3 Hz, 1H), 8.53 (s, 1H), 8.37 (d, J=4.3 Hz, 1H), 8.17 (s, 1H), 7.43 (s, 1H), 7.34 (d, J=8.2 Hz, 1H), 7.29 (d, J=8.1 Hz, 1H), 5.54-5.26 (m, 1H), 3.21-3.03 (m, 1H), 3.00-2.77 (m, 1H), 2.30 (s, 6H), 1.78 (s, 1H).

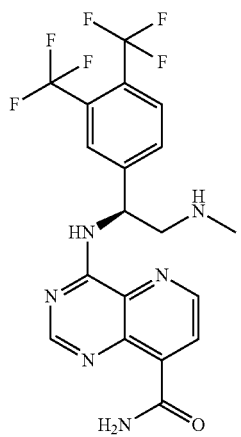 [SMILES: CNC[C@@H](Nc1ncnc2c(C(N)=O)ccnc12)c1ccc(C(F)(F)F)c(C(F)(F)F)c1]

4-[(S)-1-(3,4-Bis-trifluoromethyl-phenyl)-2-methyl-amino-ethylamino]-pyrido[3,2-d]pyrimidine-8-carboxylamide (43)

Compound 43 was prepared following general synthesis scheme 7 wherein 4-hydroxypyrido[3,2-d]pyrimidine-8-carboxamide (G) was reacted with N—[(S)-2-Amino-2-(3,4-bis-trifluoromethyl-phenyl)-ethyl]-N-methyl-4-nitro-benzenesulfonamide hydrochloride to give the title compound as a white solid. LC/MS [459 (M+H)]; $^1$H NMR (400 MHz, DMSO-d6) δ 9.90 (s, 1H), 9.34 (s, 1H), 9.02 (d, 1H), 8.54 (s, 1H), 8.39 (d, 1H), 8.18 (d, 2H), 7.98 (q, 2H), 5.62 (s, 1H), 3.16 (dd, 1H), 3.00 (dd, 1H), 2.32 (d, 3H).

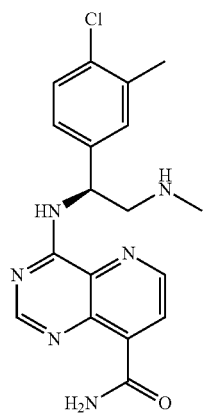 [SMILES: CNC[C@@H](Nc1ncnc2c(C(N)=O)ccnc12)c1ccc(Cl)c(C)c1]

4-[(S)-1-(4-Chloro-phenyl)-2-methylamino-ethylamino]-pyrido[3,2-d]pyrimidine-8-carboxylic Acid Amide (45)

Compound 45 was prepared following general synthesis scheme 8 wherein 4-hydroxypyrido[3,2-d]pyrimidine-8-carboxamide (G) was reacted with N—[(S)-2-Amino-2-(4-chloro-phenyl)-ethyl]-N-methyl-4-nitro-benzenesulfonamide hydrochloride to give the title compound as a white solid. LC/MS [357 (M+H)].

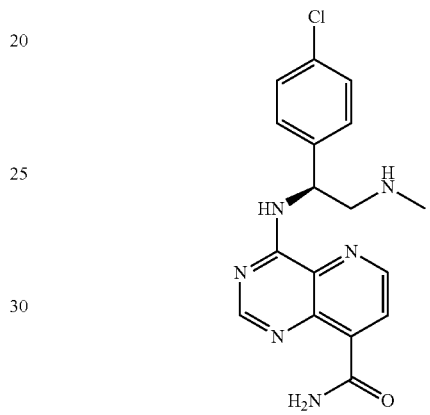

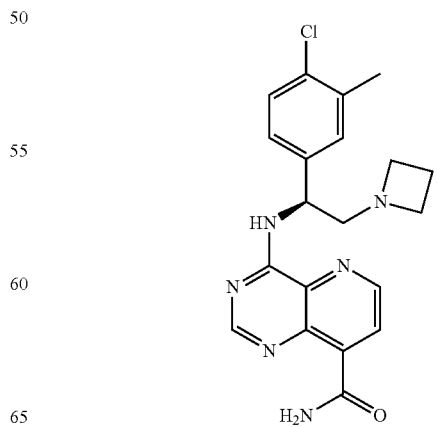

4-[(S)-2-Azetidin-1-yl-1-(4-chloro-3-methyl-phenyl)-ethylamino]-pyrido[3,2-d]pyrimidine-8-carboxylic Acid Amide (46)

Compound 46 was prepared following general synthesis scheme 7 wherein 4-hydroxypyrido[3,2-d]pyrimidine-8-carboxamide (G) was reacted with (S)-2-Azetidin-1-yl-1-(4-chloro-3-methyl-phenyl)-ethylamine dihydrochloride to give the title compound as an off-white solid. LC/MS [397 (M+H)]; $^1$H NMR (500 MHz, DMSO-d6) δ 9.95 (s, 1H), 9.01 (s, 1H), 8.99 (d, J=4.5 Hz, 1H), 8.53 (s, 1H), 8.37 (d, J=4.5 Hz, 1H), 8.17 (s, 1H), 7.45 (s, 1H), 7.39-7.24 (m, 2H), 5.34-5.17 (m, 1H), 3.20-2.98 (m, 5H), 2.83-2.71 (m, 1H), 2.29 (s, 3H), 2.01-1.84 (m, 1H).

4-[(S)-2-Azetidin-1-yl-1-(3-difluoromethyl-4-fluoro-phenyl)-ethylamino]-pyrido[3,2-d]pyrimidine-8-carboxylic Acid Amide (48)

Compound 48 was prepared following general synthesis scheme 7 wherein 4-hydroxypyrido[3,2-d]pyrimidine-8-carboxamide (G) was reacted with (S)-2-Azetidin-1-yl-1-(3-difluoromethyl-4-fluoro-phenyl)-ethylamine hydrochloride to give the title compound as a white solid. LC/MS [409 (M+H)]; $^1$H NMR (400 MHz, DMSO-d6) δ 9.93 (s, 1H), 9.09 (d, 1H), 9.02 (d, 1H), 8.55 (s, 1H), 8.39 (d, 1H), 8.18 (s, 1H), 7.58 (t, 1H), 7.52 (d, 1H), 7.45 (d, 1H), 7.29 (s, 1H), 7.16 (s, 1H), 7.02 (s, 1H), 5.34 (dd, 1H), 3.20-3.02 (m, 4H), 2.84 (dd, 2H), 1.99-1.85 (m, 2H).

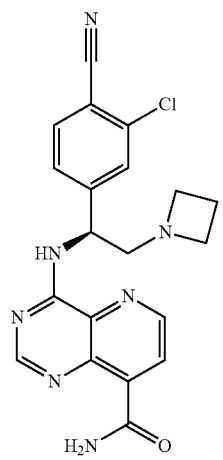 [SMILES: N#Cc1ccc([C@@H](CN2CCC2)Nc2ncnc3c(C(N)=O)ccnc23)cc1Cl]

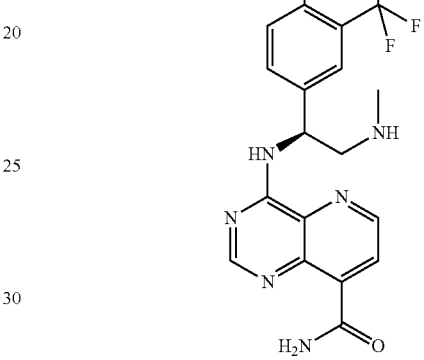

4-[(S)-2-Azetidin-1-yl-1-(3-chloro-4-cyano-phenyl)-ethylamino]-pyrido[3,2-d]pyrimidine-8-carboxylic Acid Amide (47)

Compound 47 was prepared following general synthesis scheme 7 wherein 4-hydroxypyrido[3,2-d]pyrimidine-8-carboxamide (G) was reacted with 4-((S)-1-Amino-2-azetidin-1-yl-ethyl)-2-chloro-benzonitrile hydrochloride to give the title compound as a white solid. LC/MS [409 (M+H)]; $^1$H NMR (400 MHz, DMSO-d6) δ 9.90 (s, 1H), 9.16 (d, 1H), 9.03 (d, 1H), 8.56 (s, 1H), 8.40 (d, 1H), 8.18 (s, 1H), 7.93 (d, 1H), 7.66 (d, 1H), 5.35 (s, 1H), 3.27-2.97 (m, 2H), 2.88 (d, 2H), 2.01-1.83 (m, 4H).

4-[(S)-1-(4-Fluoro-3-trifluoromethyl-phenyl)-2-methylamino-ethylamino]-pyrido[3,2-d]pyrimidine-8-carboxylic Acid Amide (49)

Compound 49 was prepared following general synthesis scheme 7 wherein 4-hydroxypyrido[3,2-d]pyrimidine-8-carboxamide (G) was reacted with N—[(S)-2-Amino-2-(4-fluoro-3-trifluoromethyl-phenyl)-ethyl]-N-methyl-4-nitro-benzenesulfonamide hydrochloride to give the title compound as a white solid. LC/MS [409 (M+H)]; $^1$H NMR (400 MHz, Acetonitrile-d3) δ 10.30 (s, 1H), 8.94 (d, 1H), 8.47 (d, 3H), 7.72 (dd, 2H), 7.28 (t, 1H), 6.59 (s, 1H), 5.41 (d, 1H), 3.13 (dd, 1H), 3.03 (dd, 1H), 2.38 (s, 3H).

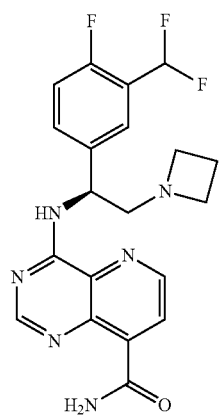 [SMILES: NC(=O)c1ccnc2c(N[C@H](CN3CCC3)c3ccc(F)c(C(F)F)c3)ncnc12]

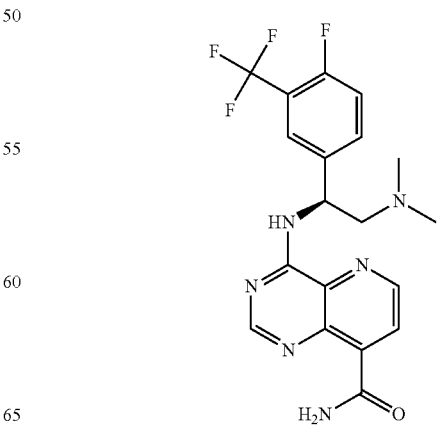

4-[(S)-2-Dimethylamino-1-(4-fluoro-3-trifluoromethyl-phenyl)-ethylamino]-pyrido[3,2-d]pyrimidine-8-carboxylic Acid Amide (50)

Compound 50 was prepared following general synthesis scheme 7 wherein 4-hydroxypyrido[3,2-d]pyrimidine-8-carboxamide (G) was reacted with (S)-1-(4-Fluoro-3-trifluoromethyl-phenyl)-N2,N2-dimethyl-ethane-1,2-diamine hydrochloride to give the title compound as a white solid. LC/MS [423 (M+H)]; $^1$H NMR (400 MHz, Acetonitrile-d3) δ 10.31 (s, 1H), 8.96 (d, 1H), 8.55-8.42 (m, 3H), 7.90-7.73 (m, 2H), 7.33 (t, 1H), 6.63 (s, 1H), 5.55 (s, 1H), 3.20 (s, 1H), 2.81 (s, 1H), 2.17 (s, 6H).

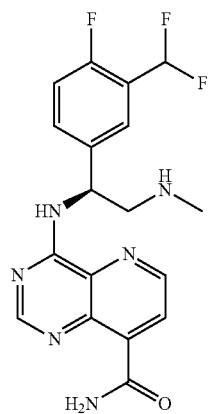 [SMILES: CNC[C@@H](Nc1ncnc2c(C(N)=O)ccnc12)c1ccc(F)c(C(F)F)c1]

4-[(S)-1-(3-Difluoromethyl-4-fluoro-phenyl)-2-methylamino-ethylamino]-pyrido[3,2-d]pyrimidine-8-carboxylic Acid Amide (51)

Compound 51 was prepared following general synthesis scheme 7 wherein 4-hydroxypyrido[3,2-d]pyrimidine-8-carboxamide (G) was reacted with N—[(S)-2-Amino-2-(3-difluoromethyl-4-fluoro-phenyl)-ethyl]-N-methyl-4-nitro-benzenesulfonamide hydrochloride to give the title compound as a white solid. LC/MS [391 (M+H)].

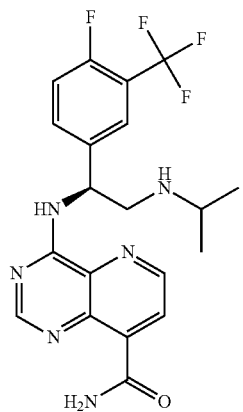 [SMILES: CC(C)NC[C@@H](Nc1ncnc2c(C(N)=O)ccnc12)c1ccc(F)c(C(F)(F)F)c1]

4-[(S)-1-(4-Fluoro-3-trifluoromethyl-phenyl)-2-isopropylamino-ethylamino]-pyrido[3,2-d]pyrimidine-8-carboxylic Acid Amide (52)

Compound 52 was prepared following general synthesis scheme 7 wherein 4-hydroxypyrido[3,2-d]pyrimidine-8-carboxamide (G) was reacted with N—[(S)-2-Amino-2-(4-fluoro-3-trifluoromethyl-phenyl)-ethyl]-N-isopropyl-4-nitro-benzenesulfonamide hydrochloride to give the title compound as a white solid. LC/MS [437 (M+H)]; $^1$H NMR (400 MHz, Acetonitrile-d3) δ 10.31 (s, 1H), 8.93 (d, 1H), 8.49 (t, 3H), 7.79-7.64 (m, 2H), 7.28 (t, 1H), 6.59 (s, 1H), 5.38 (s, 1H), 3.14 (dt, 2H), 2.89-2.72 (m, 1H), 1.03 (t, 6H).

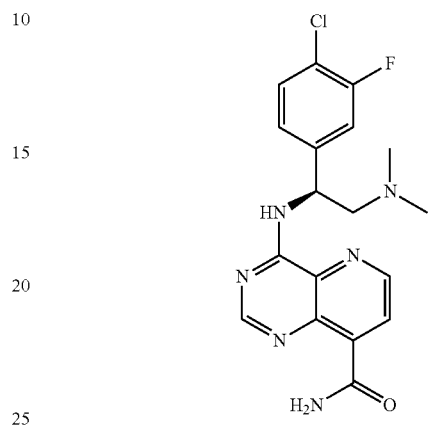

4-[(S)-1-(4-Chloro-3-fluoro-phenyl)-2-dimethylamino-ethylamino]-pyrido[3,2-d]pyrimidine-8-carboxylic Acid Amide (53)

Compound 53 was prepared following general synthesis scheme 7 wherein 4-hydroxypyrido[3,2-d]pyrimidine-8-carboxamide (G) was reacted with (S)-1-(4-Chloro-3-fluoro-phenyl)-N2,N2-dimethyl-ethane-1,2-diamine hydrochloride to give the title compound as a white solid. LC/MS [390 (M+H)]; $^1$H NMR (400 MHz, Acetonitrile-d3) δ 10.34 (s, 1H), 8.96 (d, 1H), 8.49 (d, 2H), 8.35 (s, 1H), 7.46 (t, 1H), 7.35 (d, 1H), 7.28 (d, 1H), 6.62 (s, 1H), 5.26 (d, 1H), 2.93 (t, 1H), 2.60 (dd, 1H), 2.29 (s, 6H).

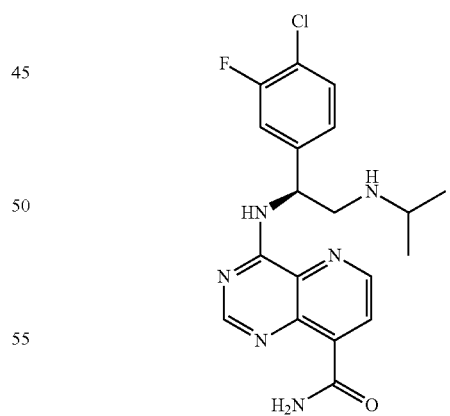

4-[(S)-1-(4-Chloro-3-fluoro-phenyl)-2-isopropylamino-ethylamino]-pyrido[3,2-d]pyrimidine-8-carboxylic Acid Amide (54)

Compound 54 was prepared following general synthesis scheme 7 wherein 4-hydroxypyrido[3,2-d]pyrimidine-8-carboxamide (G) was reacted with N—[(S)-2-Amino-2-(4- chloro-3-fluoro-phenyl)-ethyl]-N-isopropyl-4-nitro-benzenesulfonamide hydrochloride to give the title compound as a white solid. LC/MS [404 (M+H)].

(400 MHz, DMSO-d6) δ 9.93 (d, 1H), 9.26 (s, 1H), 9.00 (d, 1H), 8.54 (s, 1H), 8.37 (d, 1H), 8.16 (d, 1H), 7.92 (dd, 1H), 7.82 (ddd, 1H), 7.44 (dd, 1H), 5.51 (m, 1H), 3.17 (dd, 1H), 2.99 (dd, 1H), 2.62-2.52 (q, 2H), 0.97 (t, 3H).

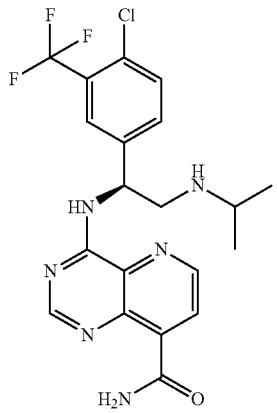 [SMILES: CC(C)NC[C@@H](Nc1ncnc2c(C(N)=O)ccnc12)c1ccc(Cl)c(C(F)(F)F)c1]

4-[(S)-1-(4-Chloro-3-trifluoromethyl-phenyl)-2-isopropylamino-ethylamino]-pyrido[3,2-d]pyrimidine-8-carboxylic Acid Amide (55)

Compound 55 was prepared following general synthesis scheme 7 wherein 4-hydroxypyrido[3,2-d]pyrimidine-8-carboxamide (G) was reacted with N—[(S)-2-Amino-2-(4-chloro-3-trifluoromethyl-phenyl)-ethyl]-N-isopropyl-4-nitro-benzenesulfonamide to give the title compound as a white solid. LC/MS [454 (M+H)]; ¹H NMR (400 MHz, DMSO-d6) δ 9.92 (s, 1H), 9.26 (s, 1H), 9.01 (d, 1H), 8.55 (s, 1H), 8.38 (d, 1H), 8.17 (s, 1H), 8.01 (s, 1H), 7.76 (d, 1H), 7.67 (d, 1H), 5.47 (s, 1H), 3.15 (d, 1H), 3.02 (s, 1H), 2.80-2.69 (m, 1H), 0.96 (dd, 6H).

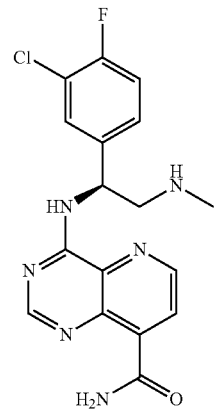

4-[(S)-1-(3-Chloro-4-fluoro-phenyl)-2-methylamino-ethylamino]-pyrido[3,2-d]pyrimidine-8-carboxylic Acid Amide (57)

Compound 57 was prepared following general synthesis scheme 7 wherein 4-hydroxypyrido[3,2-d]pyrimidine-8-carboxamide (G) was reacted with N—[(S)-2-Amino-2-(3-chloro-4-fluoro-phenyl)-ethyl]-N-methyl-4-nitro-benzenesulfonamide hydrochloride to give the title compound as a white solid. LC/MS [376 (M+H)]; ¹H NMR (400 MHz, Acetonitrile-d3) δ 10.31 (s, 1H), 8.93 (d, 1H), 8.46 (dd, 3H), 7.51 (d, 1H), 7.36 (s, 1H), 7.20 (t, 1H), 6.58 (s, 1H), 5.34 (dd, 1H), 3.11 (dd, 1H), 3.00 (dd, 1H), 2.37 (s, 3H).

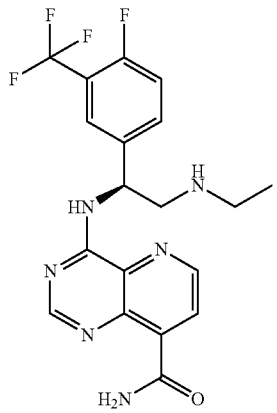 [SMILES: CCNC[C@@H](Nc1ncnc2c(C(N)=O)ccnc12)c1ccc(F)c(C(F)(F)F)c1]

4-[(S)-2-Ethylamino-1-(4-fluoro-3-trifluoromethyl-phenyl)-ethylamino]-pyrido[3,2-d]pyrimidine-8-carboxylic Acid Amide (56)

Compound 56 was prepared following general synthesis scheme 7 wherein 4-hydroxypyrido[3,2-d]pyrimidine-8-carboxamide (G) was reacted with N—[(S)-2-Amino-2-(4-fluoro-3-trifluoromethyl-phenyl)-ethyl]-N-ethyl-4-nitro-benzenesulfonamide hydrochloride to give the title compound as a white solid. LC/MS [423 (M+H)]; ¹H NMR

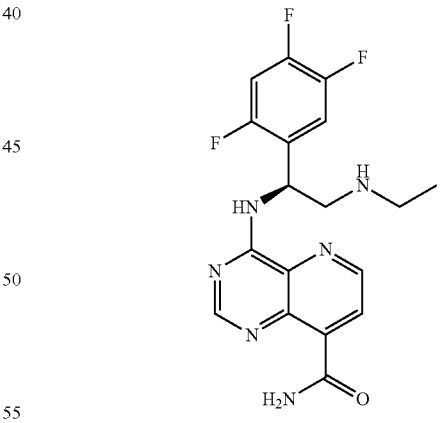

4-[(S)-2-Ethylamino-1-(2,4,5-trifluoro-phenyl)-ethylamino]-pyrido[3,2-d]pyrimidine-8-carboxylic Acid Amide (58)

Compound 58 was prepared following general synthesis scheme 7 wherein 4-hydroxypyrido[3,2-d]pyrimidine-8-carboxamide (G) was reacted with N—[(S)-2-Amino-2-(2,4,5-trifluoro-phenyl)-ethyl]-N-ethyl-4-nitro-benzenesulfonamide hydrochloride to give the title compound as a white solid. LC/MS [391 (M+H)]; ¹H NMR (400 MHz, DMSO-d6) δ 9.92 (s, 1H), 9.13 (s, 1H), 9.02 (d, 1H), 8.57 (s, 1H), 8.38 (t, 1H), 8.18 (s, 1H), 7.66 (dd, 1H), 7.53 (td, 1H), 5.71 (s, 1H), 3.15 (dd, 1H), 2.95 (dd, 1H), 2.67-2.55 (q, 2H), 0.98 (t, 3H).

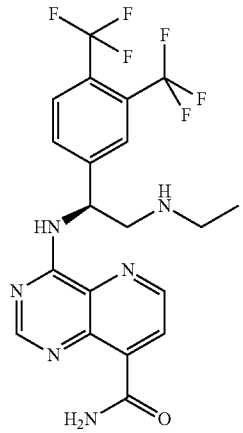 [SMILES: CCNC[C@@H](Nc1ncnc2c(C(N)=O)ccnc12)c1ccc(C(F)(F)F)c(C(F)(F)F)c1]

4-[(S)-1-(3,4-Bis-trifluoromethyl-phenyl)-2-ethyl-amino-ethylamino]-pyrido[3,2-d]pyrimidine-8-carboxylic Acid Amide (59)

Compound 59 was prepared following general synthesis scheme 7 wherein 4-hydroxypyrido[3,2-d]pyrimidine-8-carboxamide (G) was reacted with N—[(S)-2-Amino-2-(3,4-bis-trifluoromethyl-phenyl)-ethyl]-N-ethyl-4-nitro-benzenesulfonamide hydrochloride to give the title compound as a white solid. LC/MS [473 (M+H)]; $^1$H NMR (400 MHz, DMSO-d6) δ 9.91 (s, 1H), 9.35 (s, 1H), 9.03 (d, 1H), 8.55 (s, 1H), 8.40 (d, 1H), 8.19 (d, 2H), 7.99 (q, 2H), 5.60 (s, 1H), 3.25-3.15 (m, 1H), 3.06 (s, 1H), 2.58 (d, 2H), 0.98 (t, 3H).

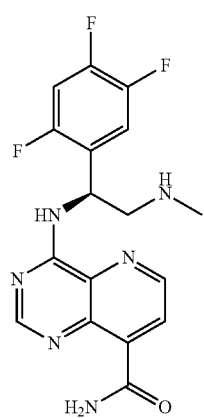 [SMILES: CNC[C@@H](Nc1ncnc2c(C(N)=O)ccnc12)c1cc(F)c(F)cc1F]

4-[(S)-2-Methylamino-1-(2,4,5-trifluoro-phenyl)-ethylamino]-pyrido[3,2-d]pyrimidine-8-carboxylic Acid Amide (60)

Compound 60 was prepared following general synthesis scheme 7 wherein 4-hydroxypyrido[3,2-d]pyrimidine-8-carboxamide (G) was reacted with N—[(S)-2-Amino-2-(2,4,5-trifluoro-phenyl)-ethyl]-N-methyl-4-nitro-benzenesulfonamide hydrochloride to give the title compound as a white solid. LC/MS [377 (M+H)].

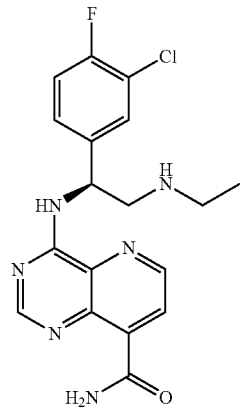 [SMILES: CCNC[C@@H](Nc1ncnc2c(C(N)=O)ccnc12)c1ccc(F)c(Cl)c1]

4-[(S)-1-(3-Chloro-4-fluoro-phenyl)-2-ethylamino-ethylamino]-pyrido[3,2-d]pyrimidine-8-carboxylic Acid Amide (61)

Compound 61 was prepared following general synthesis scheme 7 wherein 4-hydroxypyrido[3,2-d]pyrimidine-8-carboxamide (G) was reacted with N—[(S)-2-Amino-2-(3-chloro-4-fluoro-phenyl)-ethyl]-N-ethyl-4-nitro-benzenesulfonamide hydrochloride to give the title compound as a white solid. LC/MS [390 (M+H)]; $^1$H NMR (400 MHz, DMSO-d6) δ 9.94 (s, 1H), 9.16 (s, 1H), 9.00 (d, 1H), 8.56 (s, 1H), 8.38 (d, 1H), 8.17 (s, 1H), 7.71 (dd, 1H), 7.52-7.43 (m, 1H), 7.35 (t, 1H), 5.44 (s, 1H), 3.16 (dd, 1H), 2.96 (dd, 1H), 2.57 (dt, 2H), 0.98 (t, 3H).

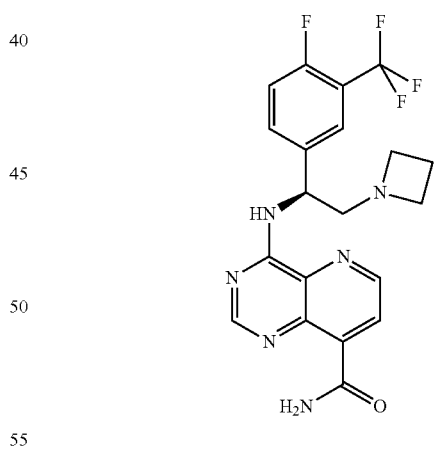

4-[(S)-2-Azetidin-1-yl-1-(4-fluoro-3-trifluoromethyl-phenyl)-ethylamino]-pyrido[3,2-d]pyrimidine-8-carboxylic Acid Amide (62)

Compound 62 was prepared following general synthesis scheme 7 wherein 4-hydroxypyrido[3,2-d]pyrimidine-8-carboxamide (G) was reacted with (S)-2-Azetidin-1-yl-1-(4-fluoro-3-trifluoromethyl-phenyl)-ethylamine to give the title compound as a white solid. LC/MS [390 (M+H)].

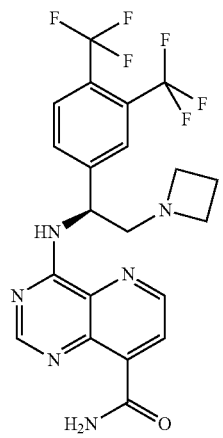 [SMILES: NC(=O)c1ccnc2c(N[C@H](CN3CCC3)c3ccc(C(F)(F)F)c(C(F)(F)F)c3)ncnc12]

4-[(S)-2-Azetidin-1-yl-1-(3,4-bis-trifluoromethyl-phenyl)-ethylamino]-pyrido[3,2-d]pyrimidine-8-carboxylic Acid Amide (63)

Compound 63 was prepared following general synthesis scheme 7 wherein 4-hydroxypyrido[3,2-d]pyrimidine-8-carboxamide (G) was reacted with (S)-2-Azetidin-1-yl-1-(3,4-bis-trifluoromethyl-phenyl)-ethylamine to give the title compound as a white solid. LC/MS [485 (M+H)].

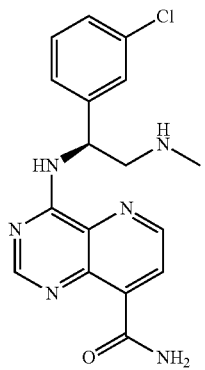 [SMILES: CNC[C@@H](Nc1ncnc2c(C(N)=O)ccnc12)c1cccc(Cl)c1]

4-[(S)-1-(3-Chloro-phenyl)-2-methylamino-ethylamino]-pyrido[3,2-d]pyrimidine-8-carboxylic Acid Amide (64)

Compound 64 was prepared following general synthesis scheme 7 wherein 4-hydroxypyrido[3,2-d]pyrimidine-8-carboxamide (G) was reacted with N—[(S)-2-Amino-2-(3-chloro-phenyl)-ethyl]-N-methyl-4-nitro-benzenesulfonamide hydrochloride to give the title compound. LC/MS [357 (M+H)] $^1$H NMR (400 MHz, DMSO-d6) δ 9.96 (s, 1H), 9.20 (br s, 1H), 9.00 (d, 1H), 8.55 (s, 1H), 8.39 (d, 1H), 8.20 (s, 1H), 7.56 (m, 1H), 7.47-7.26 (m, 3H), 5.48 (s, 1H), 3.16 (dd, 1H), 2.92 (dd, 1H), 2.31 (s, 3H)

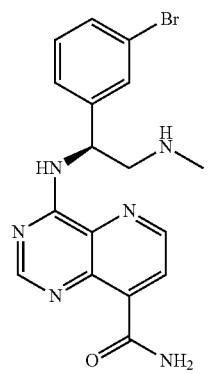 [SMILES: CNC[C@@H](Nc1ncnc2c(C(N)=O)ccnc12)c1cccc(Br)c1]

4-[(S)-1-(3-Bromo-phenyl)-2-methylamino-ethylamino]-pyrido[3,2-d]pyrimidine-8-carboxylic Acid Amide (65)

Compound 65 was prepared following general synthesis scheme 7 wherein 4-hydroxypyrido[3,2-d]pyrimidine-8-carboxamide (G) was reacted with N—[(S)-2-Amino-2-(3-bromo-phenyl)-ethyl]-N-methyl-4-nitro-benzenesulfonamide hydrochloride to give the title compound. LC/MS [401,403 (M+H)] $^1$H NMR (400 MHz, DMSO-d6) δ 9.96 (s, 1H), 9.19 (s, 1H), 9.01 (d, 1H), 8.55 (s, 1H), 8.39 (d, 1H), 8.19 (s, 1H), 7.70 (m, 1H), 7.52-7.38 (m, 3H), 7.29 (m, 1H), 5.48 (s, 1H), 3.15 (dd, 1H), 2.91 (dd, 1H), 2.31 (s, 3H)

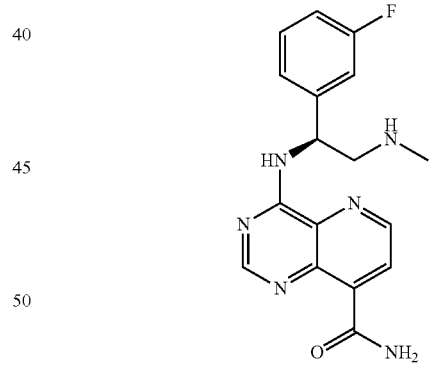

4-[(S)-1-(3-Fluoro-phenyl)-2-methylamino-ethylamino]-pyrido[3,2-d]pyrimidine-8-carboxylic Acid Amide (66)

Compound 66 was prepared following general synthesis scheme 7 wherein 4-hydroxypyrido[3,2-d]pyrimidine-8-carboxamide (G) was reacted with N—[(S)-2-Amino-2-(3-fluoro-phenyl)-ethyl]-N-methyl-4-nitro-benzenesulfonamide hydrochloride to give the title compound. LC/MS [341 (M+H)].

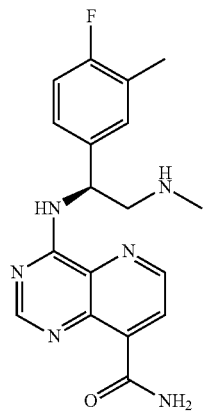 [SMILES: CNC[C@@H](Nc1ncnc2c(C(N)=O)ccnc12)c1ccc(F)c(C)c1]

4-[(S)-1-(4-Fluoro-3-methyl-phenyl)-2-methyl-amino-ethylamino]-pyrido[3,2-d]pyrimidine-8-carboxylic Acid Amide (67)

Compound 67 was prepared following general synthesis scheme 7 wherein 4-hydroxypyrido[3,2-d]pyrimidine-8-carboxamide (G) was reacted with N—[(S)-2-Amino-2-(4-fluoro-3-methyl-phenyl)-ethyl]-N-methyl-4-nitro-benzenesulfonamide hydrochloride to give the title compound. LC/MS [355 (M+H)] $^1$H NMR (400 MHz, DMSO-d6) δ 9.97 (s, 1H), 9.07 (s, 1H), 8.99 (d, 1H), 8.54 (s, 1H), 8.38 (d, 1H), 8.17 (s, 1H), 7.38 (m, 1H), 7.30 (m, 1H), 7.07 (m, 1H), 5.45 (s, 1H), 3.15 (dd, 1H), 2.89 (dd, 1H), 2.32 (s, 3H), 2.21 (s, 3H).

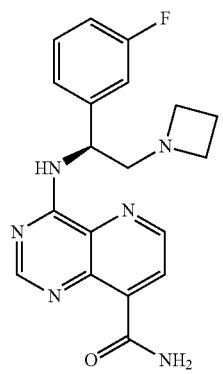 [SMILES: NC(=O)c1ccnc2c(N[C@H](CN3CCC3)c3cccc(F)c3)ncnc12]

4-[(S)-2-Azetidin-1-yl-1-(3-fluoro-phenyl)-ethylamino]-pyrido[3,2-d]pyrimidine-8-carboxylic Acid Amide (68)

Compound 68 was prepared following general synthesis scheme 7 wherein 4-hydroxypyrido[3,2-d]pyrimidine-8-carboxamide (G) was reacted with (S)-2-azetidin-1-yl-1-(3-fluoro-phenyl)-ethylamine hydrochloride to give the title compound. LC/MS [367 (M+H)] $^1$H NMR (400 MHz, DMSO-d6) δ 9.94 (s, 1H), 9.07 (d, 1H), 9.01 (d, 1H), 8.56 (s, 1H), 8.39 (d, 1H), 8.17 (s, 1H), 7.34 (m, 3H), 7.07 (m, 1H), 5.36 (m, 1H), 3.13 (m, 4H), 2.86 (m, 1H), 1.96 (m, 2H).

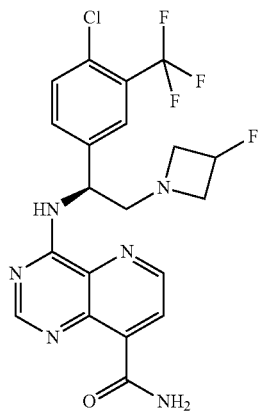 [SMILES: NC(=O)c1ccnc2c(N[C@H](CN3CC(F)C3)c3ccc(Cl)c(C(F)(F)F)c3)ncnc12]

4-[(S)-1-(4-Chloro-3-trifluoromethyl-phenyl)-2-(3-fluoro-azetidin-1-yl)-ethylamino]-pyrido[3,2-d]pyrimidine-8-carboxylic Acid Amide (69)

Compound 69 was prepared following general synthesis scheme 7 wherein 4-hydroxypyrido[3,2-d]pyrimidine-8-carboxamide (G) was reacted with (S)-1-(4-chloro-3-trifluoromethyl-phenyl)-2-(3-fluoro-azetidin-1-yl)-ethylamine hydrochloride to give the title compound. LC/MS [469 (M+H)] $^1$H NMR (400 MHz, DMSO-d6) δ 9.92 (s, 1H), 9.26 (d, 1H), 9.01 (d, 1H), 8.57 (s, 1H), 8.39 (d, 1H), 8.17 (s, 1H), 8.08 (s, 1H), 7.82 (m, 1H), 7.68 (m, 1H), 5.45 (m, 1H), 5.12 (m, 1H), 3.59 (m, 2H), 3.21 (m, 2H), 2.95 (m, 5.6 Hz, 1H).

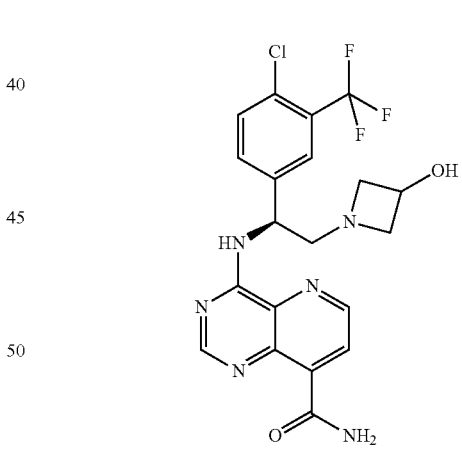

4-[(S)-1-(4-Chloro-3-trifluoromethyl-phenyl)-2-(3-hydroxy-azetidin-1-yl)-ethylamino]-pyrido[3,2-d]pyrimidine-8-carboxylic Acid Amide (70)

Compound 70 was prepared following general synthesis scheme 7 wherein 4-hydroxypyrido[3,2-d]pyrimidine-8-carboxamide (G) was reacted with (S)-1-(4-chloro-3-trifluoromethyl-phenyl)-2-(3-hydroxy-azetidin-1-yl)-ethylamine hydrochloride to give the title compound. LC/MS [467 (M+H)].

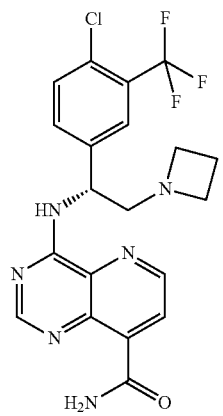 [SMILES: NC(=O)c1ccnc2c(N[C@@H](CN3CCC3)c3ccc(Cl)c(C(F)(F)F)c3)ncnc12]

4-[(R)-2-Azetidin-1-yl-1-(4-chloro-3-trifluoromethyl-phenyl)-ethylamino]-pyrido[3,2-d]pyrimidine-8-carboxylamide (71)

Compound 71 was prepared following general synthesis scheme 7 wherein 4-hydroxypyrido[3,2-d]pyrimidine-8-carboxamide (G) was reacted with (R)-2-azetidin-1-yl-1-(4-chloro-3-trifluoromethyl-phenyl)-ethylamine hydrochloride to give the title compound. LC/MS [451 (M+H)].

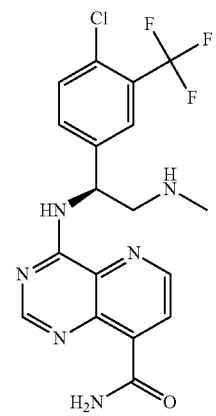 [SMILES: CNC[C@@H](Nc1ncnc2c(C(N)=O)ccnc12)c1ccc(Cl)c(C(F)(F)F)c1]

4-[(S)-1-(4-Chloro-3-trifluoromethyl-phenyl)-2-methylamino-ethylamino]-pyrido[3,2-d]pyrimidine-8-carboxylic Acid Amide (72)

Compound 72 was prepared following general synthesis scheme 10 wherein methyl 4-hydroxypyrido[3,2-d]pyrimidine-8-carboxylate (I) was reacted with N—[(S)-2-Amino-2-(4-chloro-3-trifluoromethyl-phenyl)-ethyl]-N-methyl-4-nitro-benzenesulfonamide to give the title compound. LC/MS [425 (M+H)]; $^1$H NMR (400 MHz, DMSO-d6) δ 9.93 (s, 1H), 9.29 (s, 1H), 9.00 (d, J=4.6 Hz, 1H), 8.54 (s, 1H), 8.38 (d, J=4.5 Hz, 1H), 8.19 (s, 1H), 8.00 (s, 1H), 7.77 (d, J=8.4 Hz, 1H), 7.66 (d, J=8.3 Hz, 1H), 5.53 (s, 1H), 3.13 (dd, J=12.3, 8.3 Hz, 1H), 2.94 (dd, J=12.4, 5.8 Hz, 1H), 2.29 (s, 3H), 1.92 (s, 1H).

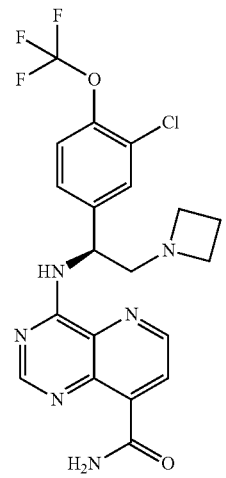 [SMILES: NC(=O)c1ccnc2c(N[C@H](CN3CCC3)c3ccc(OC(F)(F)F)c(Cl)c3)ncnc12]

4-[(S)-2-Azetidin-1-yl-1-(3-chloro4-trifluoromethoxy-phenyl)-ethylamino]-pyrido[3,2-d]pyrimidine-8-carboxylamide (73)

Compound 73 was prepared following general synthesis scheme 11 wherein 4-hydroxypyrido[3,2-d]pyrimidine-8-carboxamide (G) was reacted with (S)-2-azetidin-1-yl-1-(-(3-chloro4-trifluoromethoxy-phenyl)-ethylamine hydrochloride to give 33 mg of the title compound as a white solid. LC/MS [467 (M+H)]; $^1$H NMR (400 MHz, DMSO-d6) δ 9.91 (s, 1H), 9.12 (d, J=8.1 Hz, 1H), 9.00 (d, J=4.5 Hz, 1H), 8.56 (s, 1H), 8.38 (d, J=4.5 Hz, 1H), 8.17 (s, 1H), 7.85 (s, 1H), 7.58 (d, J=8.1 Hz, 1H), 7.51 (d, J=8.6 Hz, 1H), 5.33 (q, J=7.7 Hz, 1H), 3.13 (hept, J=6.7 Hz, 4H), 3.09-2.99 (m, 1H), 2.82 (dd, J=12.0, 5.8 Hz, 1H), 1.92 (p, J=7.0 Hz, 2H).

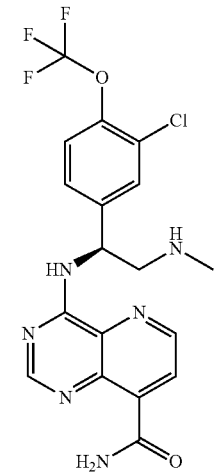 [SMILES: CNC[C@@H](Nc1ncnc2c(C(N)=O)ccnc12)c1ccc(OC(F)(F)F)c(Cl)c1]

4-[(S)-1-(3-Chloro-4-trifluoromethoxy-phenyl)-2-methylamino-ethylamino]-pyrido[3,2-d]pyrimidine-8-carboxylamide (74)

Compound 74 was prepared following general synthesis scheme 11 wherein 4-hydroxypyrido[3,2-d]pyrimidine-8-carboxamide (G) was reacted with N—[(S)-2-amino-2-(3-chloro4-trifluoromethoxy-phenyl)-ethyl]-N-methyl-4-nitrobenzenesulfonamide hydrochloride to give 57 mg of the title compound as a white solid. LC/MS [441 (M+H)])]; 1H NMR (400 MHz, DMSO-d6) δ 9.92 (d, J=3.5 Hz, 1H), 9.35-9.22 (m, 1H), 9.01 (d, J=4.4 Hz, 1H), 8.57 (s, 1H), 8.39 (d, J=4.5 Hz, 1H), 8.18 (d, J=3.9 Hz, 1H), 7.83 (d, J=1.9 Hz, 1H), 7.61-7.47 (m, 2H), 5.60 (s, 1H), 3.26 (d, J=11.3 Hz, 1H), 3.05 (d, J=12.4 Hz, 1H), 2.37 (s, 3H).

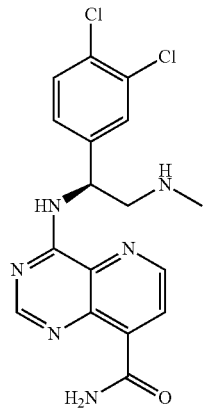

4-[(S)-1-(3,4-Dichloro-phenyl)-2-methylamino-ethylamino]-pyrido[3,2-d]pyrimidine-8-carboxylamide (75)

Compound 75 was prepared following general synthesis scheme 11 wherein 4-hydroxypyrido[3,2-d]pyrimidine-8-carboxamide (G) was reacted with N—[(S)-2-amino-2-(3,4-dichloro-phenyl)-ethyl]-N-methyl-4-nitro-benzenesulfonamide. LC/MS [391 (M+H)], 1H NMR (400 MHz, DMSO-d6) δ 9.94 (d, 1H), 9.17 (d, 1H), 9.00 (d, 1H), 8.55 (s, 1H), 8.38 (d, 1H), 8.17 (d, 1H), 7.76 (d, 1H), 7.58 (d, 1H), 7.45 (dd, 1H), 5.46 (s, 1H), 3.13 (dd, 1H), 2.92 (dd, 1H), 2.30 (s, 3H).

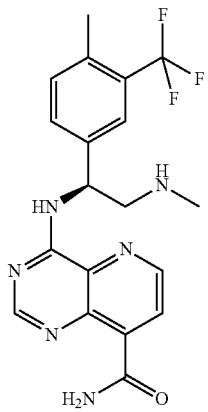 [SMILES: CNC[C@@H](Nc1ncnc2c(C(N)=O)ccnc12)c1ccc(C)c(C(F)(F)F)c1]

4-[(S)-2-Methylamino-1-(4-methyl-3-trifluoromethyl-phenyl)-ethylamino]-pyrido[3,2-d]pyrimidine-8-carboxylic Acid Amide (76)

Compound 76 was prepared following general synthetic scheme 11 wherein 4-hydroxypyrido[3,2-d]pyrimidine-8-carboxamide (G) was reacted with N—[(S)-2-Amino-2-(4-methyl-3-trifluoromethyl-phenyl)-ethyl]-N-methyl-4-nitro-benzenesulfonamide. LC-MS [405 (M+1)]; 1H NMR (400 MHz, DMSO-d6) δ 9.95 (d, J=3.4 Hz, 1H), 9.21 (d, J=8.5 Hz, 1H), 9.00 (d, J=4.6 Hz, 1H), 8.54 (s, 1H), 8.38 (d, J=4.5 Hz, 1H), 8.16 (d, J=3.5 Hz, 1H), 7.80 (s, 1H), 7.63 (d, J=7.9 Hz, 1H), 7.38 (d, J=8.1 Hz, 1H), 5.51 (s, 1H), 3.15 (dd, J=12.4, 8.4 Hz, 1H), 2.92 (dd, J=12.3, 5.5 Hz, 1H), 2.40 (s, 4H), 2.30 (s, 3H).

Example 3: p70S6K Enzyme Assay p70S6K inhibitor compounds were diluted and plated in 96 well plates. A reaction mixture including the following components were then added to the compound plate to initiate the enzyme reaction: p70S6K (3 nM, T412E mutant, Millipore) was mixed with 24 μM ATP in an assay buffer containing 100 mM Hepes (pH 7.5), 5 mM $MgCl_2$, 1 mM DTT, 0.015% Brij and 1 μM of the substrate peptide FITC-AHA-AKRRRLSSLRA-OH (derived from the S6 ribosomal protein sequence, FITC=fluorescein isothiocyanate, AHA=6-aminohexanoic acid). The reaction was incubated for 90 min at 25° C., before the addition of 10 mM EDTA to stop the reaction. The proportion of substrate and product (phosphorylated) peptide was analyzed on a Caliper Life Sciences Lab Chip 3000, using a pressure of −1.4 psi, and upstream and downstream voltages of −3000 and −700, respectively. Product peaks were resolved before substrate peaks on the resulting chromatograms. To assess the inhibitory potential of the compounds, $IC_{50}$ values were determined, as shown above.

Example 4: AKT/PKB Kinase Assay

In order to measure AKT inhibition in the Caliper Life Sciences LC3000, a TTP Mosquito liquid handling instrument was used to place 125 nl of the appropriate concentration of inhibitor in 100% DMSO (for a dose response curve calculation) into each well of a 384-well plate. To this reaction, the following components were added to a final volume of 12.5 μl:

0.1 ng/μl His-AKT (Full Length) (Invitrogen, Part # P2999, Lot #641228C);
160 μM ATP (Fluka, 02055);
1 mM DTT (Sigma, D0632);
1 mM $MgCl_2$ (Sigma, M1028);
1 μM substrate peptide (sequence FITC-AHA-GRPRTSS-FAEG-$NH_2$), synthesized by
Tufts Peptide Synthesis service;
100 mM HEPES pH 7.5 (Calbiochem, 391338); and
0.015% Brij-35 (Sigma, B4184).

The reaction was incubated for 90 min at 25° C., and then stopped by the addition of 70 μl of Stop buffer (100 mM HEPES pH 7.5, 0.015% Brij-35, 10 mM EDTA (Sigma, E7889)). The plate was read on a Caliper LC 3000 in an Off-Chip mobility shift assay format, using the following parameters for a 12-sipper chip: screening pressure −2.3 psi, upstream voltage −500, and downstream voltage −3000. These conditions cause unphosphorylated substrate and phosphorylated product peptide to resolve as separate peaks allowing direct measurement of percentage of conversion of substrate to product. The percent conversion was plotted against concentration of inhibitor to produce a sigmoidal dose response curve, from which an $IC_{50}$ was calculated.

The values for the p70S6K and AKT enzyme inhibition assays for selected compounds set out in the Experimental section are presented in Table 1. The data are presented as follows:

+++++: <25 nM;
++++: 25-100 nM;
+++: 101 nM-500 nM;
++: 501 nM-1000 nM;
+: >1 µM.

TABLE 1 p70S6K Enzyme Inhibition by Compounds Described by Formula (I)

| Compound | IC$_{50}$ p70S6K (nM) | IC$_{50}$ AKT (nM) |
|---|---|---|
| 1 | +++ | + |
| 2 | +++++ | + |
| 3 | + | + |
| 4 | +++++ | + |
| 5 | + | + |
| 6 | ++ | + |
| 7 | + | + |
| 8 | ++++ | + |
| 9 | ++ | + |
| 10 | +++++ | +++ |
| 11 | ++++ | +++ |
| 12 | +++++ | +++++ |
| 13 | +++++ | +++++ |
| 14 | +++++ | +++++ |
| 15 | +++++ | +++++ |
| 16 | +++++ | +++++ |
| 17 | ++++ | +++ |
| 18 | +++++ | +++ |
| 19 | + | + |
| 20 | +++++ | ++++ |
| 21 | +++++ | +++++ |
| 22 | +++++ | +++ |
| 23 | ++++ | +++ |
| 24 | | |
| 25 | +++++ | ++ |
| 26 | +++++ | +++++ |
| 27 | +++++ | +++ |
| 28 | +++++ | +++++ |
| 29 | +++++ | ++++ |
| 30 | +++++ | ++++ |
| 31 | ++++ | + |
| 32 | +++++ | +++ |
| 33 | +++++ | ++++ |
| 34 | ++++ | +++ |
| 35 | +++++ | ++++ |
| 36 | +++++ | +++ |
| 37 | +++++ | ++ |
| 38 | +++++ | ++++ |
| 39 | +++++ | +++ |
| 40 | ++++ | + |
| 41 | +++++ | +++++ |
| 42 | +++++ | +++++ |
| 43 | +++++ | +++++ |
| 44 | +++++ | +++++ |
| 45 | +++++ | ++++ |
| 46 | +++++ | +++++ |
| 47 | +++++ | +++++ |
| 48 | +++++ | +++++ |
| 49 | +++++ | +++++ |
| 50 | +++++ | ++++ |
| 51 | +++++ | +++++ |
| 52 | ++++ | +++ |
| 53 | +++++ | ++++ |
| 54 | ++++ | +++ |
| 55 | +++ | +++ |
| 56 | +++++ | ++++ |
| 57 | +++++ | +++++ |
| 58 | ++++ | +++ |
| 59 | +++++ | +++++ |
| 60 | ++++ | ++++ |
| 61 | +++++ | ++++ |
| 62 | +++++ | +++++ |
| 63 | +++++ | +++++ |
| 64 | +++++ | +++++ |
| 65 | +++++ | +++++ |
| 66 | +++++ | +++++ |
| 67 | +++++ | +++++ |

TABLE 1-continued p70S6K Enzyme Inhibition by Compounds Described by Formula (I)

| Compound | IC$_{50}$ p70S6K (nM) | IC$_{50}$ AKT (nM) |
|---|---|---|
| 68 | +++++ | ++++ |
| 69 | +++++ | ++++ |
| 70 | +++++ | ++++ |
| 71 | ++ | + |
| 72 | +++++ | +++++ |
| 73 | +++++ | ++++ |
| 74 | +++++ | ++++ |
| 75 | +++++ | +++++ |
| 76 | +++++ | +++++ |

Example 5: Pharmaceutical Preparations (A) Injection vials: A solution of 100 g of an active ingredient according to the invention and 5 g of disodium hydrogen phosphate in 3 l of bidistilled water are adjusted to pH 6.5 using 2 N hydrochloric acid, sterile filtered, are transferred into injection vials, are lyophilized under sterile conditions and are sealed under sterile conditions. Each injection vial contains 5 mg of active ingredient.

(B) Suppositories: A mixture of 20 g of an active ingredient according to the invention is melted with 100 g of soy lecithin and 1400 g of cocoa butter, is poured into moulds and is allowed to cool. Each suppository contains 20 mg of active ingredient.

(C) Solution: A solution is prepared from 1 g of an active ingredient according to the invention, 9.38 g of NaH$_2$PO$_4$.2H$_2$O, 28.48 g of Na$_2$HPO$_4$.12H$_2$O and 0.1 g of benzalkonium chloride in 940 ml of bidistilled water. The pH is adjusted to 6.8, and the solution is made up to 1 l and sterilized by irradiation. This solution could be used in the form of eye drops.

(D) Ointment: 500 mg of an active ingredient according to the invention are mixed with 99.5 g of Vaseline under aseptic conditions.

(E) Tablets: A mixture of 1 kg of an active ingredient according to the invention, 4 kg of lactose, 1.2 kg of potato starch, 0.2 kg of talc and 0.1 kg of magnesium stearate is pressed to give tablets in a conventional manner in such a way that each tablet contains 10 mg of active ingredient.

(F) Coated tablets: Tablets are pressed analogously to Example E and are subsequently coated in a conventional manner with a coating of sucrose, potato starch, talc, tragacanth and dye.

(G) Capsules: 2 kg of an active ingredient according to the invention are introduced into hard gelatin capsules in a conventional manner in such a way that each capsule contains 20 mg of the active ingredient.

(H) Ampoules: A solution of 1 kg of an active ingredient according to the invention in 60 l of bidistilled water is sterile filtered, is transferred into ampoules, is lyophilized under sterile conditions and is sealed under sterile conditions. Each ampoule contains 10 mg of active ingredient.

(I) Inhalation spray: 14 g of an active ingredient according to the invention are dissolved in 10 l of isotonic NaCl solution, and the solution is transferred into commercially available spray containers with a pump mechanism. The solution could be sprayed into the mouth or nose. One spray shot (about 0.1 ml) corresponds to a dose of about 0.14 mg.

The invention claimed is:
1. A compound of formula (I):

(I)

wherein:
W¹ is CH;
W² is CH;
W³ is N; and
W⁴ is CH; or
W¹ is CH;
W² is CH;
W³ is CH; and
W⁴ is N;
R¹ is Ar or Het¹;
each of R², R⁴, and R⁵ is independently Y;
R³ is Y or —(CH₂)$_p$—NR⁴R⁵;
or R² and R³ together with the atoms to which each is attached, may form —(CH₂)$_n$—NY—(CH₂)$_p$;
or R⁴ and R⁵ together with the atoms to which each is attached, may form —(CY₂)$_q$—;
each Y is independently H or A;
each A is independently unbranched or branched alkyl having 1-10 C atoms, in which 1-7 H atoms can be replaced independently from one another by Hal;
Ar is an unsaturated or aromatic monocyclic or bicyclic carbocycle having 3-10 C atoms, which can be substituted by at least one substituent selected from the group consisting of Hal, A, OY, CN, COY, COOY, CONYY, NYCOY, NYCONYY, SO₂Y, SO₂NYY, NYSO₂Y, NYY, NO₂, OCN, SCN, SH, phenyl and Het¹, where the phenyl is optionally substituted by Hal, A, OY, CN, COY, COOY, CONYY, NYCOY, NYCONYY, SO₂Y, SO₂NYY, NYSO₂Y, NYY, NO₂, OCN, SCN or SH;
each Het¹ is independently an unsaturated or aromatic monocyclic or bicyclic heterocycle having 2-10 C atoms and 1-4 N, O and/or S atoms, which can be substituted by at least one substituent selected from the group consisting of Hal, A, OY, CN, COY, COOY, CONYY, NYCOY, NYCONYY, SO₂Y, SO₂NYY, NYSO₂Y, NYY, NO₂, OCN, SCN, SH, phenyl and Het², where the phenyl is optionally substituted by Hal, A, OY, CN, COY, COOY, CONYY, NYCOY, NYCONYY, SO₂Y, SO₂NYY, NYSO₂Y, NYY, NO₂, OCN, SCN or SH;
Het² is saturated, unsaturated or aromatic monocyclic 5-6-membered heterocycle having 2-5 C atoms and 1-3 N, O and/or S atoms, which is optionally substituted by Hal, A, OY, CN, COY, COOY, CONYY, NYCOY, NYCONYY, SO₂Y, SO₂NYY, NYSO₂Y, NYY, NO₂, OCN, SCN or SH;
each Hal is independently F, Cl, Br or I;
m is 0 or 1;
each of n and p is independently 0, 1, 2 or 3; and
q is 2, 3, 4, 5 or 6;
and/or a physiologically acceptable salt thereof.

2. The compound according to claim 1, wherein R¹ is phenyl or pyridyl, each of which is optionally substituted.

3. The compound according to claim 2, wherein R¹ is

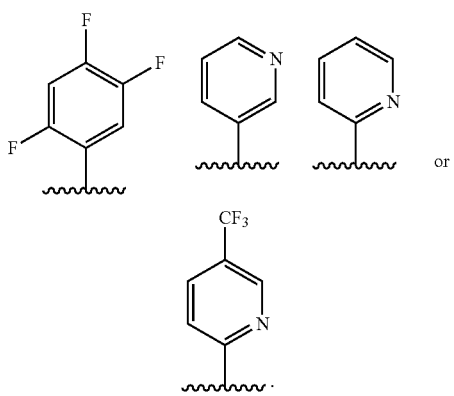

4. The compound according to claim 3, wherein R¹ is

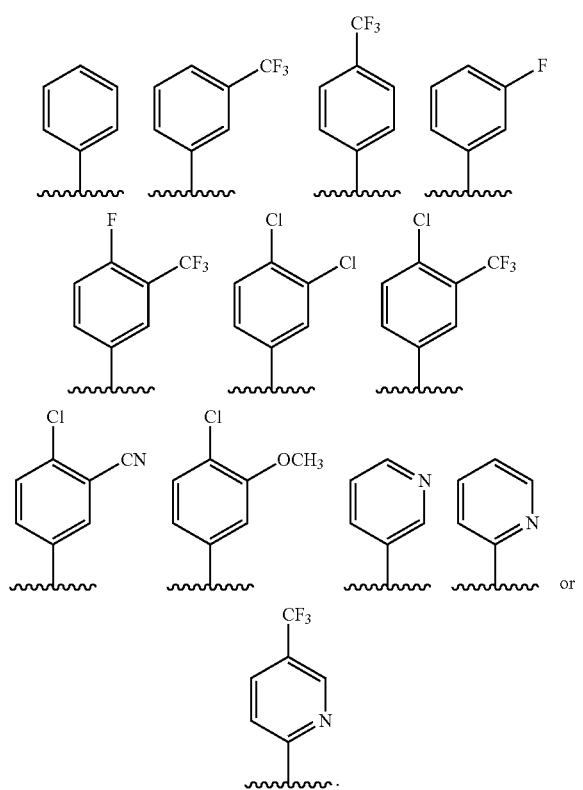

5. The compound according to claim 1, wherein R³ is H or —(CH₂)$_p$—NR⁴R⁵.

6. The compound according to claim 5, wherein R³ is H,

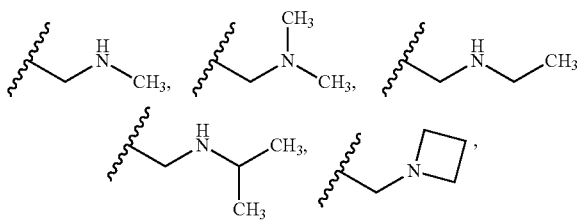

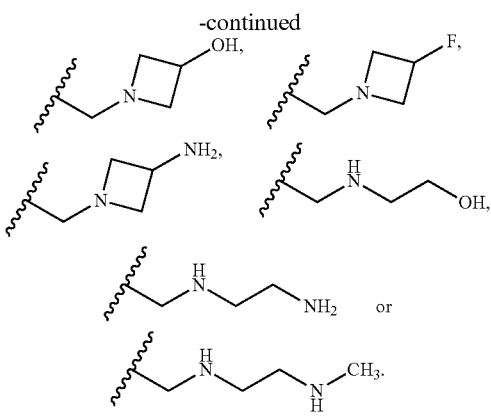

7. The compound according to claim 6, wherein R³ is H,

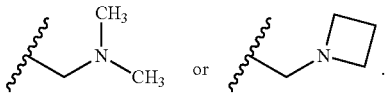

8. The compound according to claim 1, wherein R² and R³ together with the atoms to which each is attached, is

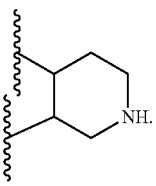 [SMILES: *C1CCNCC1*]

9. The compound according to claim 1, which is selected from the group consisting of:
- (R)-4-((2-(azetidin-1-yl)-1-(4-chloro-3-(trifluoromethyl) phenyl)ethyl)amino)pyrido[4,3-d]pyrimidine-8-carboxamide (19);
- (S)-4-((2-(azetidin-1-yl)-1-(4-chloro-3-(trifluoromethyl) phenyl)ethyl)amino)pyrido[4,3-d]pyrimidine-8-carboxamide (20);
- 4-[(S)-1-(4-Isopropyl-phenyl)-2-methylamino-ethylamino]-pyrido[3,4-d]pyrimidine-8-carboxylic acid amide (40); and
- 4-[(S)-1-(4-Chloro-3-trifluoromethyl-phenyl)-2-methylamino-ethylamino]-pyrido[3,4-d]pyrimidine-8-carboxylic acid amide (42).

10. A pharmaceutical composition comprising as active ingredient at least one compound according to claim 1, and/or a physiologically acceptable salt thereof, together with at least one pharmaceutically tolerable excipient, and optionally in combination with one or more further active ingredients.

11. A method for inhibiting p70S6K in a system expressing p70S6K, wherein the system is contacted with at least one compound according to claim 1, and/or a physiologically acceptable salt thereof.

12. A method for treating breast cancer, bladder cancer, pancreatic cancer, renal cancer, lung cancer or neuroblastoma in a subject, comprising administering to the subject at least one compound according to claim 1, and/or a physiologically acceptable salt thereof.

* * * * *